(12) United States Patent
Mueller et al.

(10) Patent No.: US 8,968,750 B2
(45) Date of Patent: *Mar. 3, 2015

(54) MALARIA VACCINES BASED ON APICOMPLEXAN FERLINS, FERLIN-LIKE PROTEINS AND OTHER C2-DOMAIN CONTAINING PROTEINS

(75) Inventors: Ann-Kristin Mueller, Dossenheim (DE); Eva Morath, Wuerzburg (DE)

(73) Assignee: Ruprecht-Karls-Universität Heidelberg, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/513,059

(22) PCT Filed: Dec. 6, 2010

(86) PCT No.: PCT/EP2010/007399
§ 371 (c)(1),
(2), (4) Date: Aug. 14, 2012

(87) PCT Pub. No.: WO2011/066995
PCT Pub. Date: Jun. 9, 2011

(65) Prior Publication Data
US 2012/0308598 A1     Dec. 6, 2012

Related U.S. Application Data

(60) Provisional application No. 61/267,026, filed on Dec. 5, 2009.

(51) Int. Cl.
*A61K 39/015* (2006.01)
*A61K 39/00* (2006.01)

(52) U.S. Cl.
CPC ....... *A61K 39/015* (2013.01); *A61K 2039/6075* (2013.01)
USPC .................. 424/272.1; 424/191.1; 424/193.1; 424/269.1; 530/300; 530/389.1

(58) Field of Classification Search
CPC ..................................................... A61K 39/015
USPC ........................................................ 424/272.1
See application file for complete search history.

(56) References Cited

U.S. PATENT DOCUMENTS 4,518,528 A * 5/1985 Rasnick ......................... 548/533
5,198,334 A * 3/1993 Leung ................................ 435/2
(Continued)

FOREIGN PATENT DOCUMENTS

EP              1930017     * 6/2008    ............. A61K 35/32
WO         WO 95/26982 A2     10/1995
(Continued)

OTHER PUBLICATIONS

Uniprot Accession No. Q4XJH7, disclosure date Jul. 5, 2005, 86 amino acid peptide sequence that shares 100% identity with amino acid sequence 'LLDPLVVV'.*
(Continued)

*Primary Examiner* — Albert Navarro
*Assistant Examiner* — Ginny Portner
(74) *Attorney, Agent, or Firm* — Saliwanchik, Lloyd & Eisenschenk

(57) ABSTRACT

The present invention relates to peptides comprising at least one antigenic determinant or epitope of an apicomplexan Ferlin, Ferlin-like protein and/or another C2-domain containing protein for use as malaria vaccines. It further relates to compositions comprising said peptides and to the use of such compositions as malaria vaccines.

22 Claims, 15 Drawing Sheets

(56) References Cited

U.S. PATENT DOCUMENTS

| | | | |
|---|---|---|---|
| 7,951,782 B2* | 5/2011 | Murota et al. | 514/21.8 |
| 8,277,812 B2* | 10/2012 | Iannacone et al. | 424/184.1 |
| 8,343,497 B2* | 1/2013 | Shi et al. | 424/184.1 |
| 8,343,498 B2* | 1/2013 | Alexis et al. | 424/184.1 |
| 2003/0077653 A1* | 4/2003 | Baig | 435/7.1 |
| 2006/0275315 A1* | 12/2006 | Telford et al. | 424/190.1 |
| 2007/0110771 A1* | 5/2007 | Good et al. | 424/272.1 |
| 2009/0324628 A1* | 12/2009 | Theander et al. | 424/185.1 |
| 2010/0004182 A1* | 1/2010 | Murota et al. | 514/16 |
| 2010/0292179 A1* | 11/2010 | Denny et al. | 514/28 |
| 2011/0165649 A1* | 7/2011 | Tyler et al. | 435/188 |
| 2013/0005668 A1* | 1/2013 | Raitano et al. | 514/21.2 |
| 2013/0323276 A1* | 12/2013 | Pfeil et al. | 424/191.1 |

FOREIGN PATENT DOCUMENTS

| | | | | |
|---|---|---|---|---|
| WO | WO 2004/037856 A2 | 5/2004 | | |
| WO | WO 2004/078099 A2 | 9/2004 | | |
| WO | 2005063804 | * | 7/2005 | C07K 14/445 |
| WO | WO 2005/063804 A1 | 7/2005 | | |
| WO | WO 2009/082440 A2 | 7/2009 | | |

OTHER PUBLICATIONS

Boslego, John W. et al, Chapter 17, Gonorrhea Vaccines, Vaccines and Immunotherapy, 1991, pp. 211-223.*

LSBio, anti-leucine antibody, one page, Catalog ID LS-C71639, date Oct. 17, 2013.*

Uniprot accession No. Q4Z3H1, pp. 1-4, Ferlin like protein, *Plasmodium berghei*, Jul. 5, 2005.*

Magistrado, Pamela A et al, Malaria Journal, 2008, Oct. 9, 2008, vol. 7(204), pp. 1-10, CD36 selection of 3D7 *Plasmodium falciparum* associated with severe childhood malaria results in reduced VAR4 expression.*

Lec, A et al, BMC Evolutionary Biology, 2010, vol. 10(231), pp. 1-15, Phylogenetic analysis of ferlin gnes reveals ancient eukaryotic origins.*

Patel, Pryank et al, Journal of Molecular Biology, 2008, vol. 379, pp. 981-990, Solution structure of the Inner DysF Domain of Myoferlin and Implicatons for Limb Girdle Muscular Dystrophy Type 2B.*

McColm, A.A et al, Parasite Immunology, 1982, vol. 4, pp. 337-347, a comparisoooon of saponin with other adjuvants for the potentiation of protective immunity by a killed *Plasmodium yoelii* vaccine in the mouse.*

Hoffman, Stephen L et al, Protection of Humans against Malaria by Immunization with Radiation-Attenuated *Plasmodium falciparum* sporozoites, Journal of Infectious Diseases, 2002, vol. 185, pp. 1155-1164.*

Bansal, D. and Campbell, K.P. "Dysferlin and the Plasma Membrane Repair in Muscular Dystrophy," *Trends in Cell Biology*, Apr. 2004, vol. 14, No. 4, pp. 206-213.

Carlton, J.M. et al. "Genome Sequence and Comparative Analysis of the Model Rodent malaria Parasite *Plasmodium yoelii yoelii*," *Nature*, Oct. 3, 2002, vol. 419, pp. 512-519.

Cowman, A.F. et al. "Functional Analysis of *Plasmodium falciparum* Merozoite Antigens: Implications for Erythrocyte Invasion and Vaccine Development" *Phil. Trans. R. Soc. Lond*, 2002, vol. 357, pp. 25-33.

Database EMBL EBI, "A Comprehensive Survey of *Plasmodium* Life Cycle by Genomic, Transcriptomic, and Proteomic Analyses," Accession No. Q4YW56, Jul. 2005, 1 page.

Database EMBL EBI "Genome Sequence of the Human Malaria Parasite *Plasmodium falciparum*," Accession No. Q8IKS2, Mar. 2003, 1 page.

Database EMBL EBI, "Genome Sequence and Comparative Analysis of the Model Rodent malaria Parasite *Plasmodium yoelii yoelii*," Accession No. Q7PDM3, Dec. 2003, 1 page.

Database EMBL EBI, Accession No. B9QB45, Mar. 2009, 1 page.

Database EMBL EBI, "Annotation of *Toxoplasma gondii* ME49" Accession No. B6KA31, Dec. 2008, 1 page.

Faber, B.W. et al. "Malaria Vaccine-Related Benefits of a Single Protein Comprising *Plasmodium falciparum* Apical Membrane Antigen 1 Domains I and II Fused to a Modified Form of the 19-Kilodalton C-Terminal Fragment of Merozoite Surface Protein 1" *Infection and Immunity*, Dec. 2007, vol. 75, No. 12, pp. 5947-5955.

Gardner, M.J. et al. "Genome Sequence of the Human Malaria Parasite *Plasmodium falciparum*" *Nature*, 2002, vol. 419, pp. 498-511.

Hall, N. et al. "A Comprehensive Survey of *Plasmodium* Life Cycle by Genomic, Transcriptomic, and Proteomic Analyses," *Science*, Jan. 7, 2005, vol. 307, pp. 82-86.

Jiménez, J. and Bashir, R. "In Silico Functional and Structural Characterisation of Ferlin Proteins by Mapping Disease-Causing Mutations and Evolutionary Information onto Three-Dimensional Models of their C2 Domans" *Journal of the Neurological Sciences*, 2007, vol. 260, pp. 114-123.

Jobe, Ousman et al. "Liver Stages Induce Sterile Protracted Protection that is Mediated by Mjor Histocompatibility Complex Class I-Dependent Interferon-γ-Producing CD8[+] T Cells" *The Journal of Infectious Diseases*, 2007, vol. 196, pp. 599-607.

Matuschevvski, K. and Mueller, A-K, "Vaccines Against Malaria—An Update"*FEBS Journal*, 2007, vol. 274, pp. 4680-4687.

Mueller, A-K et al. "Genetically Modified *Plasmodium* Parasites as a Protective Experimental Malaria Vaccine" *Nature*, 2005, vol. 433, pp. 164-167 with Corrections & Amendments—*Nature*, 2007, vol. 446, pp. 102.

Mueller, A-K et al. "Genetically Attenuated *Plasmodium berghei* Liver Stages Persist and Elicit Sterile Protection Primarily via CD8 T Cells" *The American Journal of Pathology*, 2007, vol. 171, No. 1, pp. 107-115.

Remarque, E.J. "Apical Membrane Antigen 1: A Malaria Vaccine Candidate in Review" *Trends in Parasitology*, 2007, vol. 24, No. 2, pp. 74-84.

* cited by examiner

MALARIA VACCINES BASED ON APICOMPLEXAN FERLINS, FERLIN-LIKE PROTEINS AND OTHER C2-DOMAIN CONTAINING PROTEINS

CROSS REFERENCE TO A RELATED APPLICATION

This application is a National Stage Application of International Application Number PCT/EP2010/007399, filed Dec. 6, 2010; which claims priority to U.S. Provisional Application No. 61/267,026, filed Dec. 5, 2009; which are incorporated herein by reference in their entirety.

The Sequence Listing for this application is labeled "SeqList-29Aug13_ST25.txt" which was created on Aug. 29, 2013 and is 131 KB. The entire content of the sequence listing is incorporated herein by reference in its entirety.

The present invention relates to peptides comprising at least one antigenic determinant or epitope of an apicomplexan Ferlin, Ferlin-like protein and/or another C2-domain containing protein for use as malaria vaccines. It further relates to compositions comprising said peptides and to the use of such compositions as malaria vaccines.

BACKGROUND OF THE INVENTION

Malaria causes more than 2 million deaths each year, mainly in Africa. However, an effective vaccine, which is necessary for sustainable control of the disease, remains elusive. The feasibility of vaccination against malaria has been amply demonstrated using radiation-attenuated sporozoites (RAS), which protect rodents, non-human primates and humans by targeting the sporozoites (which are inoculated into the skin by biting *Anopheles* mosquitoes) and subsequent liver stages of the parasites. The development of RAS is aborted in the liver and thus these parasites do not progress to disease-inducing blood stage infection (FIG. 1). However, despite the sterilising immunity offered by γ-irradiated parasites, practical issues, including large-scale production and ensuring uniformity of the end product, make it unlikely that this vaccine could be licensed for human use. Nevertheless RAS is a well studied experimental vaccination model in the laboratory. The most dominant immune response in the RAS model is activated by the circumsporozoite surface protein (CSP; FIG. 2). These findings boosted the development of the RTS,S vaccine that is based on the CS protein. To date RTS,S is the most advanced malaria vaccine on the market, it is currently in clinical phase III. Studies with healthy volunteers and African children living in endemic areas showed good tolerance and safety of the vaccine. However, the efficacy of RTS,S, also with different adjuvant systems, is only 40-60%. Additionally observations in CS transgenic mice showed that protection could be observed also in mice that are tolerant to CSP, which indicates the presence of other antigens inducing the immune response of the host. Studying RAS induced immune responses is always limited by the fact that the genetic background of injected sporozoites highly varies between individual sporozoites and also between different batches of sporozoites resulting also in differently expressed antigens. Recent advances in gene targeting technology have facilitated the generation of genetically attenuated parasites (GAP) that harbour defined mutations in genes essential for parasite development. Like RAS, GAP are attenuated in the liver and thereby confer to a stage specific sterile immunity, but GAP are arrested at a specific time point (~24 hours) following initiation of infection and at a very specific stage of differentiation (FIG. 1). In contrast, RAS harbour multiple, heterogeneous mutations and growth arrest occurs at multiple stages. The well-defined genetically attenuated parasites (uis3(−) and/or uis4(−)) are therefore ideal tools for further characterisation of the protective immune responses to liver stage parasites. Studies in knock-out mice showed that Interferon-γ producing T lymphocytes mediate the GAP induced immunity and that B cells are not important. A closer look even revealed CD8+ T cells to be the major player. However, the antigenic specificities and effector mechanisms involved in that immunity are not yet understood.

It was an object of the present invention to provide means for an effective malaria vaccine. More specifically, it was an object of the present invention to identify novel antigens that are critical for immunity.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

According to the present invention, the above object is solved by a peptide comprising at least one antigenic determinant or epitope of an apicomplexan protein selected from
  Ferlin,
  a member of the Ferlin-like protein family, and
  other C2-domain containing proteins
for use as a malaria vaccine.

The term "peptide", as used herein, is meant to refer to a peptide, which is not limited in terms of its length or size. Hence, in one embodiment, the peptide is the apicomplexan protein itself or a (larger) fragment thereof. In another embodiment, the peptide is in the range of 5 to 50 amino acids, more preferably 8 to 25 amino acids, more preferably 8 to 15 amino acids.

The term "apicomplexan protein", as used herein, is meant to refer to a protein from an apicomplexan organism. Apicomplexan organisms (also referred to as apicomplexa or apicomplexia) are a large group of protists, most of which possess a unique organelle called apicoplast and an apical complex structure involved in penetrating a host's cell. They are unicellular, spore-forming parasites of mammals. Preferably, the apicomplexan organism is selected from *Plasmodium falciparum, Plasmodium berghei, Plasmodium yoelii* and *Toxoplasma gondii*. Preferably, the apicomplexan protein is a malarial apicomplexan protein, i.e. it is from an apicomplexan organism which causes malaria in mammals, preferably *Plasmodium falciparum* and *Plasmodium berghei*, most preferably *Plasmodium falciparum*.

A C2-domain is a protein structural domain involved in targeting proteins to cell membranes. It is a beta-sandwich composed of 8 β-strands that co-ordinates two or three calcium ions, which bind in a cavity formed by the first and final loops of the domain, on the membrane binding face. C2-domain containing proteins can be easily identified by a person skilled in the art based on their amino acid sequence.

In one embodiment, the other C2-domain containing proteins are selected from *Plasmodium berghei* C2-domain containing protein (Pb C2CP), its ortholog(s) in *Plasmodium falciparum* and a protein, which is at least 80%, preferably at least 85%, more preferably at least 90%, even more preferably at least 95%, even more preferably at least 96%, even more preferably at least 97%, even more preferably at least 98%, even more preferably at least 99% identical to these proteins.

The malaria vaccine of the present invention is preferably a sub-unit vaccine.

In one embodiment, the apicomplexan protein is selected from
*Plasmodium berghei* Ferlin (Pb FER),
*Plasmodium falciparum* Ferlin (Pf FER),
*Plasmodium yoelii* Ferlin (Py FER),
*Toxoplasma gondii* Ferlin (Tg FER),
*Plasmodium berghei* Ferlin-like protein (Pb FLP),
*Plasmodium falciparum* Ferlin-like protein (Pf FLP),
*Plasmodium yoelii* Ferlin-like protein (Py FLP),
*Toxoplasma gondii* Ferlin-like protein (Tg FLP),
*Plasmodium berghei* C2-domain containing protein (Pb C2CP) and
a protein, which is at least 80%, preferably at least 85%, more preferably at least 90%, even more preferably at least 95%, even more preferably at least 96%, even more preferably at least 97%, even more preferably at least 98%, even more preferably at least 99% identical to any of the above proteins.

Pb FER refers to PBANKA_131930 (SEQ ID NO. 26),
Pf FER refers to PF14_0530 (SEQ ID NO. 27),
Py FER refers to PY05745 (SEQ ID NO. 28),
Tg FER refers to TGVEG_073920 (SEQ ID NO. 29),
Pb FLP refers to PBANKA_122440 (SEQ ID NO. 30),
Pf FLP refers to MAL8P1.134 (SEQ ID NO. 31),
Py FLP refers to PY04695 (SEQ ID NO. 32),
Tg FLP refers to TGVEG_093560 (SEQ ID NO. 33), and
Pb C2CP refers to PB402109.00.0 (SEQ ID NO. 34),
wherein the above accession numbers are PlasmoDB/GeneDB accession numbers As used herein, the term "percent (%) identical" refers to sequence identity between two amino acid sequences. Identity can be determined by comparing a position in both sequences, which may be aligned for the purpose of comparison. When an equivalent position in the compared sequences is occupied by the same amino acid, the molecules are considered to be identical at that position.

Generally, a person skilled in the art is aware of the fact that some amino acid exchanges in the amino acid sequence of a protein or peptide do not have any influence on the (secondary or tertiary) structure, function and activity of the protein or peptide at all. Amino acid sequences with such "neutral" amino acid exchanges as compared to the amino acid sequences disclosed herein fall within the scope of the present invention. Also included are mutations in the original amino acid sequence that allow or facilitate the production of the peptide, in particular the apicomplexan protein itself or a larger fragment thereof, in a non-apicomplexan organism, such as *E. coli*.

In a preferred embodiment, the apicomplexan protein is selected from Pf FER, Pf FLP and a protein, which is at least 80%, preferably at least 85%, more preferably at least 90%, even more preferably at least 95%, even more preferably at least 96%, even more preferably at least 97%, even more preferably at least 98%, even more preferably at least 99% identical to Pf FER or Pf FLP.

In one embodiment, the antigenic determinant or epitope is a CD 8+ T cell epitope, a CD4+ T cell epitope or a B cell epitope, preferably a CD8+ T cell epitope. Preferably, the CD8+ T cell epitope is a *P. falciparum*-specific CD8+ T cell epitope, such as a HLA-A 0201-restricted CD8+ T cell epitope, or a *P. berghei*-specific CD8+ T cell epitope, such as a H2b-restricted CD8+ T cell epitope. A person skilled in the art knows how to identify/predict the above epitopes in a given amino acid sequence, e.g. by epitope prediction programs, such as SYFPEITHI.

In one embodiment, the antigenic determinant or epitope is derived from a domain of the Ferlin, member of the Ferlin-like protein family or other C2-domain containing proteins, wherein the domain is selected from
a C2 domain,
an ATPase domain,
an exo domain.

In one embodiment, the amino acid sequence of the antigenic determinant or epitope has a length of at least 8 amino acids. Preferably, the amino acid sequence of the antigenic determinant or epitope has a length of 8, 9 or 10 amino acids.

In one embodiment, the apicomplexan protein is *Plasmodium berghei* Ferlin (Pb FER) and the amino acid sequence of the antigenic determinant or epitope is selected from

```
                                           [SEQ ID NO. 1]
       (P8L)  P N P N F S Y L,

[SEQ ID NO. 2]
       (V8L)  V P I E Y R P L,
       and

[SEQ ID NO. 3]
       (L8L)  L N T C F L Q L
```

In one embodiment, the apicomplexan protein is *Plasmodium falciparum* Ferlin (Pf FER) and the amino acid sequence of the antigenic determinant or epitope is selected from

```
                                           [SEQ ID NO. 4]
       (N9V)  N L L D P L V V V,

[SEQ ID NO. 5]
       (Y9I)  Y L Y V N I H K I,

[SEQ ID NO. 6]
       (L9L)  L L L E G N F Y L,

[SEQ ID NO. 7]
       (K9L)  K L I P V N Y E L,

[SEQ ID NO. 8]
       (Y9L)  Y L Y E K Q Q E L,
       and

[SEQ ID NO. 9]
       (I9I)  I L I P S L P L I.
```

In one embodiment, the apicomplexan protein is *Plasmodium berghei* Ferlin-like protein (Pb FLP) and the amino acid sequence of the antigenic determinant or epitope is selected from

```
                                          [SEQ ID NO. 10]
       (S8L)  S R Y F F R A L,

[SEQ ID NO. 11]
       (L8V)  L N Y V Y S K V,

[SEQ ID NO. 12]
       (I8M)  I G Y T Y I D M,
       and
```

```
                                        [SEQ ID NO. 13]
         (V8L*)  V G T A Y I T L.
```

In one embodiment, the apicomplexan protein is *Plasmodium falciparum* Ferlin-like protein (Pf FLP) and the amino acid sequence of the antigenic determinant or epitope is selected from

```
                                        [SEQ ID NO. 14]
         (T9L*)  T L N P L L P W L,

[SEQ ID NO. 15]
         (I9L)   I L I K S E A E L,

[SEQ ID NO. 16]
         (N9V*)  N I L E P Y V K V,

[SEQ ID NO. 17]
         (Y9L*)  Y L Y G G R I F L,

[SEQ ID NO. 18]
         (L10V)  L L V A F E L V P V,

[SEQ ID NO. 19]
         (L10L)  L L I G T A Y I T L,

[SEQ ID NO. 20]
         (D10L)  D L M P I E L R S L,
         and

[SEQ ID NO. 21]
         (A10L)  A L I G K C S F G L.
```

In one embodiment, the apicomplexan protein is *Plasmodium berghei* C2-domain containing protein (Pb C2CP) and the amino acid sequence of the antigenic determinant or epitope is selected from

```
                                        [SEQ ID NO. 22]
         (A9I)   A Y I A P H T I I,

[SEQ ID NO. 23]
         (T9L)   T I R S F Y K R L,

[SEQ ID NO. 24]
         (S8V)   S P Y L F N I V,
         and

[SEQ ID NO. 25]
         (A8I)   A I Y R F N A I.
```

In one embodiment, the amino acid sequence of the antigenic determinant or epitope is selected from SEQ ID NOS. 1 to 25, preferably from SEQ ID NOS. 4 to 9 and SEQ ID NOS. 14 to 21.

In one embodiment, the peptide according to the present invention further comprises at least two antigenic determinants or epitopes of an apicomplexan protein as defined above.

In further embodiments, the peptides of the present invention comprise 3, 4, 5 or more such antigenic determinants or epitopes.

In one embodiment, the peptide according to the present invention further comprises at least one antigenic determinant or epitope of an apicomplexan protein different from
Ferlin,
a member of the Ferlin-like protein family, and
other C2-domain containing proteins.

Apicomplexan proteins different from the above-listed proteins may be known potential subunit vaccine candidates e.g. MSP1, CSP (leading vaccine candidate, RTS,S, GSK), or one or multiple candidate peptides derived from a SSH screen of the inventors.

In one embodiment, the peptide comprises further component(s), such as label(s), N- and/or C-terminal modification(s), further drug(s) or agent(s). The skilled artisan will be able to select suitable further components.

The object of the present invention is also solved by a nucleic acid molecule coding for at least one peptide as defined above. It is further solved by a plasmid comprising at least one such nucleic acid molecule.

In one embodiment, the nucleic acid molecule or the plasmid are provided for use as a malaria vaccine.

The object of the present invention is also solved by an antibody against a peptide as defined above.

The object of the present invention is further solved by a composition comprising
(i) at least one peptide as defined above,
(ii) optionally, a carrier,
(iii) optionally, an adjuvant.

In one embodiment, the composition comprises at least two peptides (i). In further embodiments, the compositions of the present invention comprise 3, 4, 5 or more of the peptide(s) as defined above.

In one embodiment, the composition further comprises at least one peptide comprising at least one antigenic determinant or epitope of an apicomplexan protein different from
Ferlin,
a member of the Ferlin-like protein family, and
other C2-domain containing proteins.

Accordingly, In the composition the peptide(s) of the present invention can be combined with other peptide (fragments) from known potential subunit vaccine candidates e.g. MSP1, CSP (leading vaccine candidate, RTS,S, GSK), finally with one or multiple candidate peptides derived from a SSH screen of the inventors.

In one embodiment, the carrier (ii) is fused to the peptide.

In one embodiment, the carrier (ii) is a virus particle or parts thereof, an envelope protein of a viral vector or of a virus particle, a nanocarrier.

In one embodiment, the virus particle is Hepatitis B virus particle or parts thereof.

In such an embodiment, the carrier (ii), e.g. Hepatitis B virus particle or parts thereof, is suitable for liver targeting of the peptide(s) of the present invention.

In one embodiment, the nanocarrier is a cell-targeted nanocarrier, such as the cell-targeted nanocarriers available from Rodos BioTarget GmbH, Hannover (www.biotargeting.org), e.g. the TargoSphere® delivery system. These nanocarriers can be combined with the desired peptide and specifically directed to antigen-presenting immuno cells (like APCs, DCs, Macrophages etc).

In one embodiment, the adjuvant (iii) is triggering CD8 T cell responses in general. Preferably, the adjuvant is a commercially available adjuvant system, e.g. IC31 (Intercell company, Vienna) since that adjuvant system is triggering CD8 T cell responses rather than antibody-mediated immunity.

In one embodiment, the composition(s) as defined above is/are provided for use as a malaria vaccine.

The object of the present invention is also solved by a method of producing a composition as defined above comprising the step of admixing at least two peptides as defined above.

The object of the present invention is also solved by a method of prevention of malaria, comprising the step of administering a peptide as defined above, or a nucleic acid molecule or plasmid as defined above, or a composition as defined above to a person in need thereof.

FIGURES

FIG. 1 shows two vaccination strategies against malaria using radiation-attenuated sporozoites (RAS) or genetically attenuated parasites (GAP), which are both based on an attenuated liver-stage (LS) development. Administration of RAS is still the "gold standard" for vaccination.

FIG. 2 shows the primary structure of circumsporozoite surface protein (CSP) and its cellular localization (surface staining of *Plasmodium* sporozoites) as revealed by immunofluorescence staining. Also shown is the approximate location of its single major histocompatibility complex (MHC) class 1 (H2 Kd)-restricted CD8+ T cell epitope (SYIPSAEKI (SEQ ID NO: 35) for *P. berghei* and SYVPSAEQI (SEQ ID NO:36) for *P. yoelii*).

FIGS. 5 A and B show the primary structures of annotated apicomplexan Ferlins and Ferlin-like proteins (FLP) and *P. berghei* C2-domain containing protein (Pb C2CP). Shown are the *P. falciparum* Ferlin and *P. berghei* Ferlin and FLP paralogs, as well as the *Toxoplasma gondii* orthologs (B). *P. berghei* and *P. falciparum* Ferlin orthologs share approximately 20% amino acid (AA) identity. The characteristic C2 domains are involved in $Ca^{2+}$-sensing and -signaling in other described Ferlin proteins. Beside these domains SMART analysis revealed domains with predicted exonuclease (exo) and ATPase activity in Pb C2CP. Also shown are predicted signal peptides at the N-terminus as well as annotated transmembrane domains (atd) and predicted transmembrane spans (pts) at the C-terminus.

Figure 6:
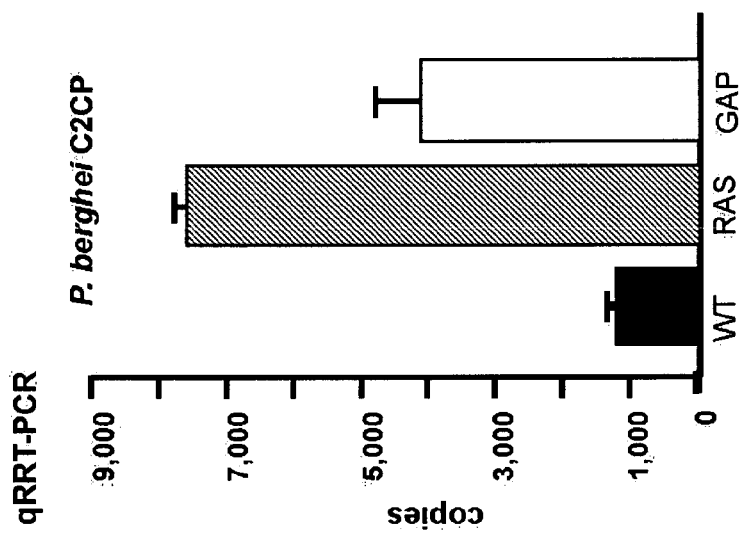

FIG. 6 shows quantitative real-time RT-PCR with total RNA isolated from 20 h *P. berghei* liver stages from either wildtype (WT), radiation-attenuated (RAS) or genetically-attenuated (GAP) parasites as templates using gene-specific oligonucleotide primer pairs. Shown are the transcript levels of *P. berghei* C2CP. Transcript quantity is represented as the number of copies (+/−SD) in comparison with an external standard curve produced with gene-specific plasmids.

Figure 7:
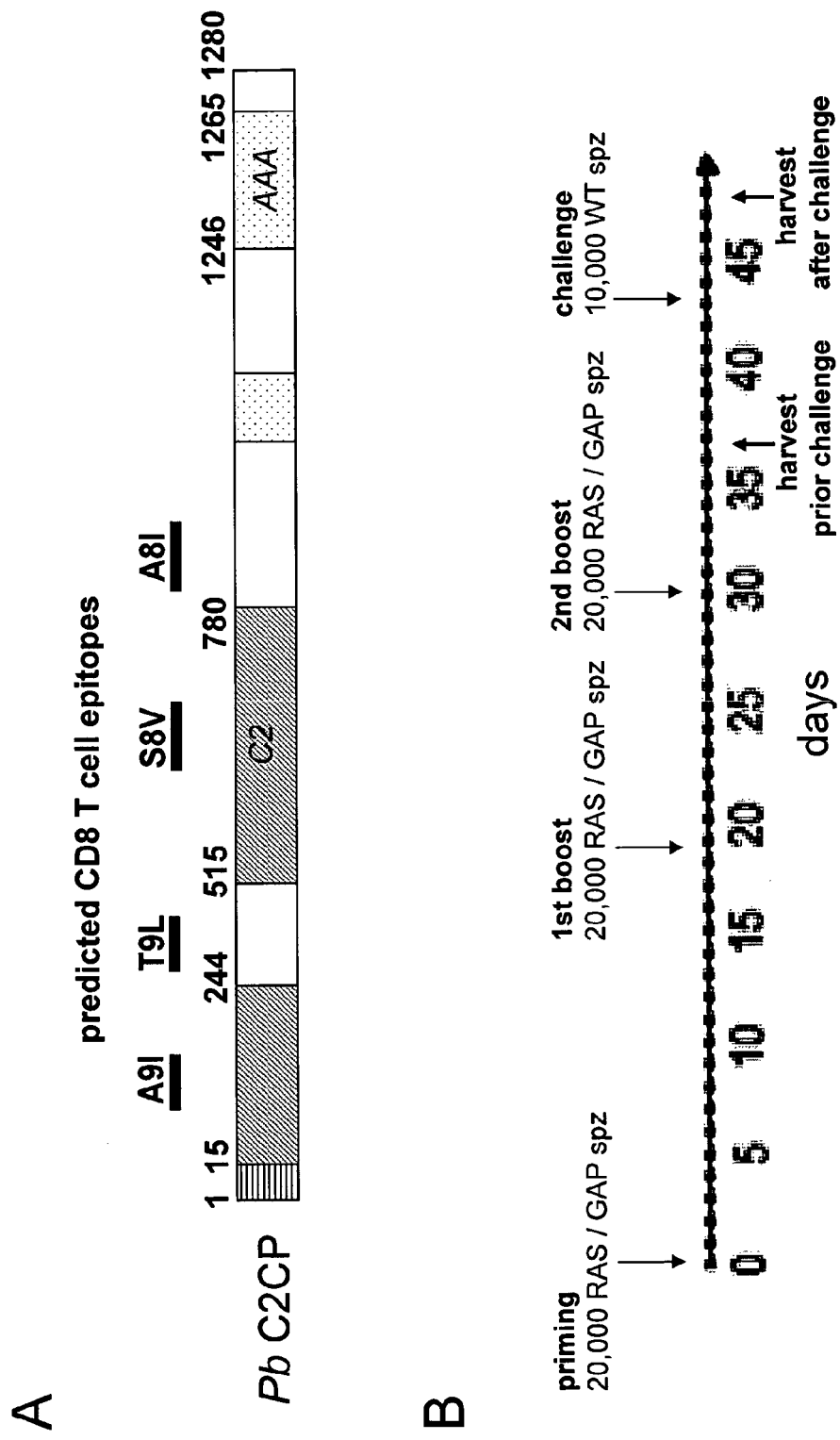

FIG. 7A shows the H-2b restricted CD8+ T cell epitopes of Pb C2CP as predicted by several programs, including the epitope prediction program SYFPEITHI. The bars shown above the primary structure indicate the approximate localisation of the predicted T cell epitopes. FIG. 7 B is a schematic diagram of the prime-two-boost immunisation protocol. C57B1/6 mice were injected i.v. with *P. berghei* RAS or GAP on day 0. The first boost was typically administered 14 days later and the second boost 14 days thereafter. Booster doses were typically lower than the priming dose. 7 days after the final boost animals were either challenged with WT sporozoites (spz) or organs were dissected for immunological studies (harvest prior challenge). The challenged mice were sacrificed 7 days after the WT challenge (harvest after challenge).

Figure 8:
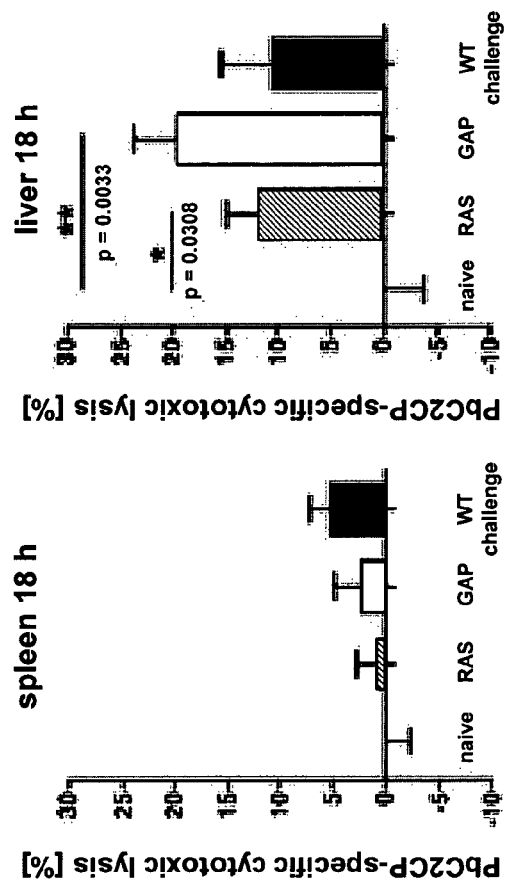

FIG. 8 shows an in vivo cytotoxicity assay based on the lysis of Pb C2CP-pulsed target cells in immunised animals. Naïve splenocytes were loaded with a Pb C2CP-derived epitope pool and labelled with 2 μM CFSE ($CFSE^{high}$) (5-(and-6)-carboxyfluorescein diacetate, succinimidyl ester, Invitrogen). A control-cell population was labelled with 0.2 μM CFSE ($CFSE^{low}$). Cell populations were mixed in equal numbers (1:1) resulting in final CFSE concentrations of 1 μM or 0.1 μM, respectively. $1 \times 10^7$ cells of this mixed population were injected i.v. into tail veins of immunised or naïve control animals 18 hours prior to cell isolation. CFSE-labeled cells were detected by flow cytometry in spleen and liver. The specific lysis was calculated as ratio of $CFSE^{high}$ cells and $CFSE^{low}$ cells and compared to the ratio detected in naïve animals. Shown are the mean percentages of lysed cells in three independent experiments, each with 3-5 mice per group.

Figure 9:
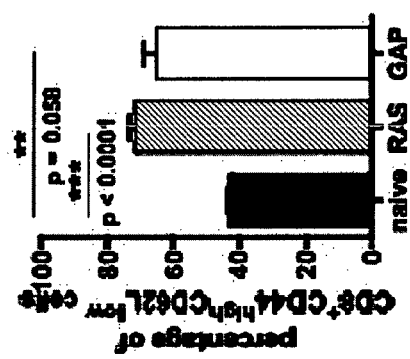

FIG. 9 shows mean percentages of $CD8^+$ $CD44^{high}CD62L^{low}$ cells in the liver after GAP and RAS immunisation of mice (n=5), showing that the effector memory T cell population ($CD8^+CD44^{high}CD62L^{low}$) in the liver increases after GAP and RAS immunisation. Liver lymphocytes were incubated over night with BMDCs and the Pb C2CP-derived peptide T9L. Surface staining was performed with antiCD8a-PacBlue conjugated antibody (1:100, BD biosciences), antiCD44-FITC (1:100, BD biosciences), antiCD62L-PE (1:200, BD biosciences) and antiCD25-Alexa647 (1:50, BD biosciences). Analysis of the stained cells was performed by flow cytometry using the FACSCanto system (BD biosciences). Resulting data were further analysed using the flowjo analysis software (http://www.flowjo.com).

Figure 10:
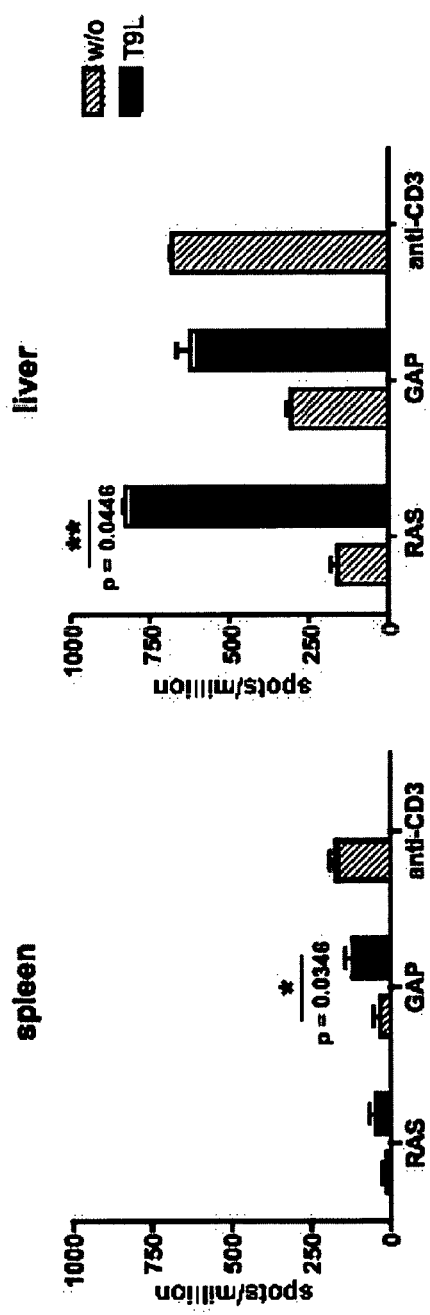

FIG. 10 shows a cytokine-based ELISpot assay measuring interferon-γ (IFN-γ) responses of effector T cells from RAS and GAP immunised mice. Cultured lymphocytes from immunised animals were restimulated over night with 1 μM of the Pb C2CP-derived peptide T9L or incubated without stimulus. Cells were subsequently transferred to MultiScreen filter plates coated with 5 μg/ml IFN-γ antibody. The detected IFN-γ response is shown as counted spots per million cultivated cells. Counts of naive control animals were subtracted. Shown are the means of counted triplets of groups of five animals.

Figure 11:
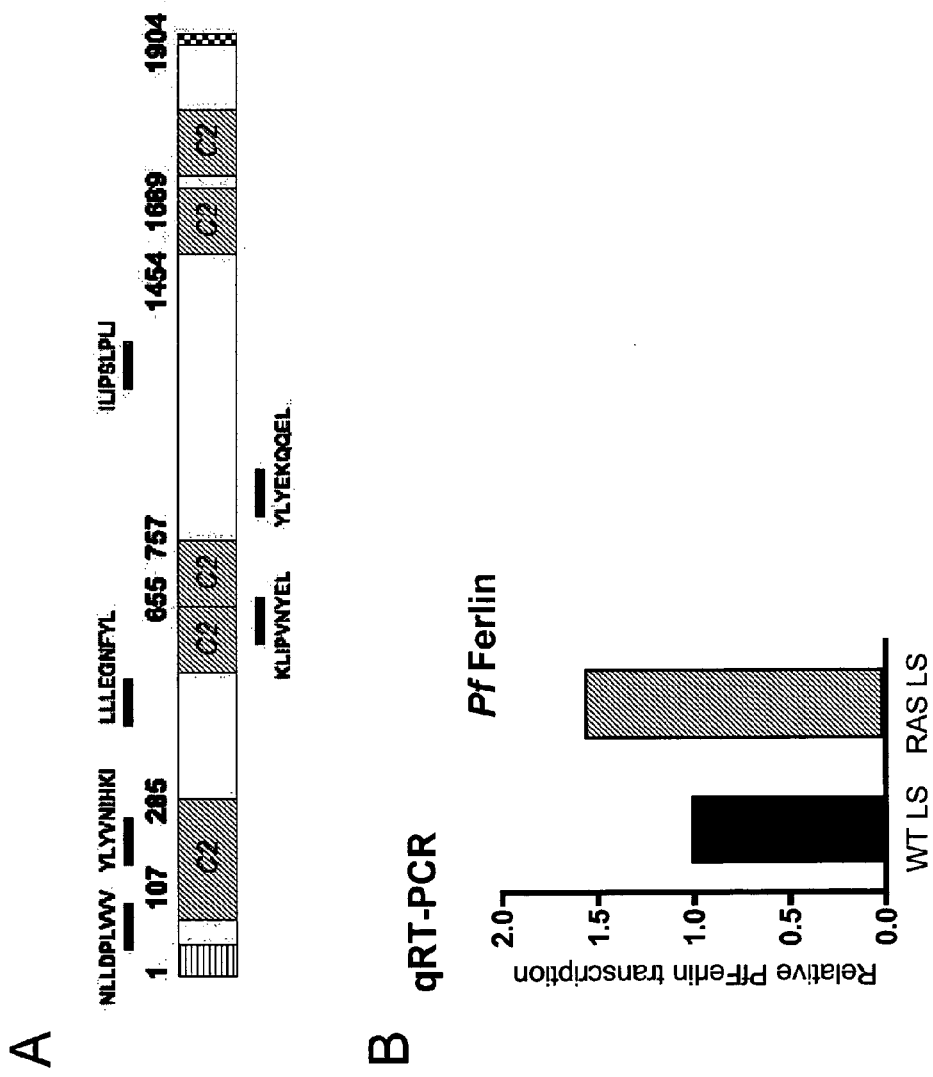

FIG. 11A shows the HLA-A 0201-restricted CD8+ T cell epitopes of Pf FER as predicted by the epitope prediction program SYFPEITHI. The bars shown above the primary structure indicate the approximate localisation of the predicted T cell epitopes. FIG. 11 B shows quantitative real-time RT-PCR with total RNA isolated from *P. falciparum* liver stages from either wildtype (WT) or radiation-attenuated (RAS) parasites as templates using gene-specific oligonucleotide primer pairs. Shown are the relative transcript levels of *P. falciparum* Ferlin (Pf FER).

FIG. 12A shows a cultured ELISpot assay over 10 days for determining the activation of CD8+ T cells after re-stimulation with Pf Ferlin specific epitopes. Each epitope was tested both individually and in pools of epitopes, which is summarised in this figure. Freshly isolated PBMCs from the blood of malaria-exposed and non-exposed (naïve) individuals were stimulated with the Pf Ferlin epitopes. The secretion of IFNγ was analysed by ELISpot. Pf AMA1, a known malarial blood stage antigen, was used as a positive control (FIG. 12B).

Figure 13:
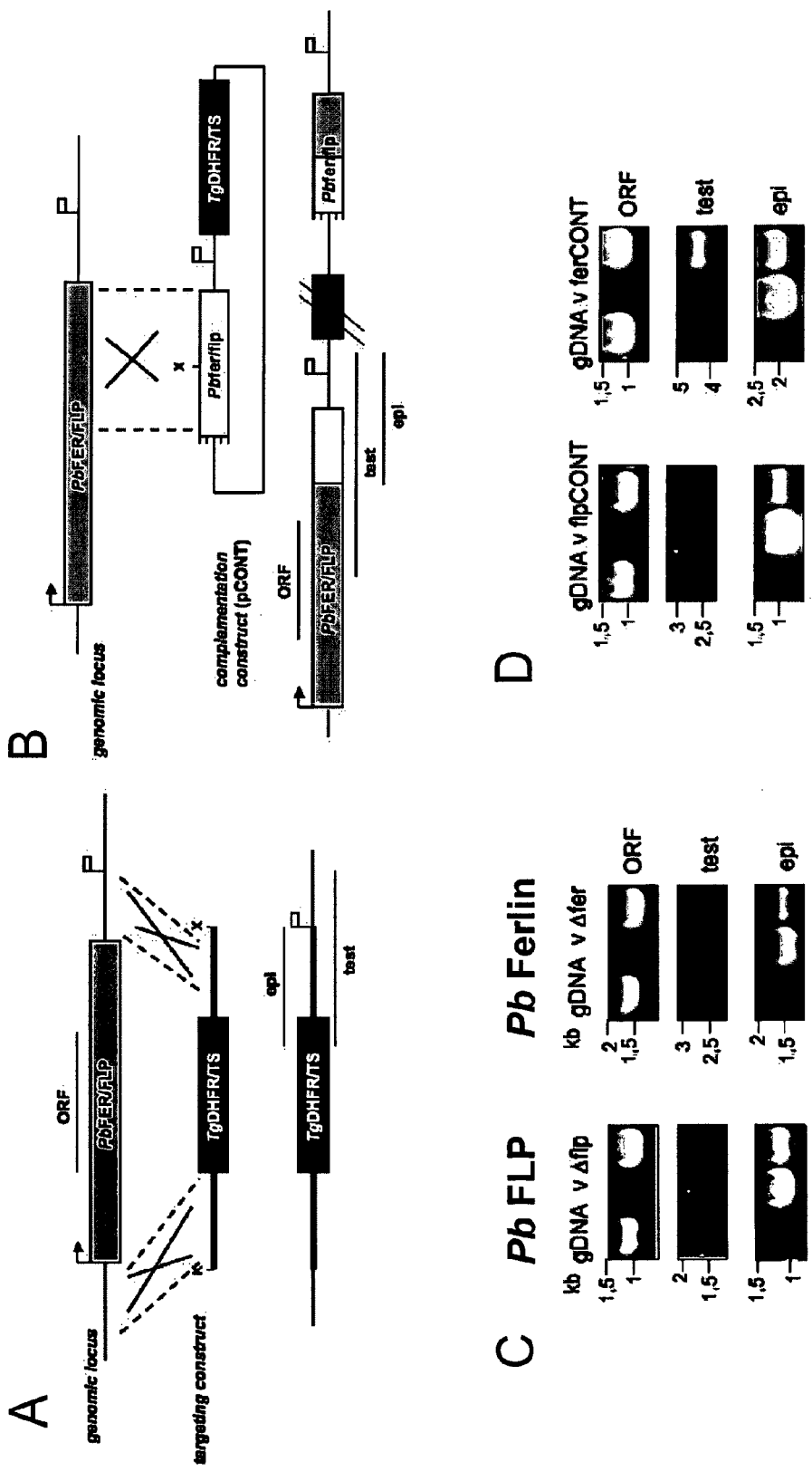

FIG. 13 shows the knock-out (A) and complementation (B) strategy of the *P. berghei* Ferlin (FER) and Ferlin-like protein (FLP). The replacement construct (A) contains the 5' and 3' untranslated regions of the *P. berghei* FER or FLP open reading frames flanking the TgDHFR/TS selectable marker. The wildtype (WT) genomic locus is targeted with the linearised KpnI/XbaI targeting vector. A double crossing-over event replaces the endogenous FER or FLP ORF, respectively, by the selectable marker. The complementation control construct (pCONT) (B) contains a 5' truncated version of the *P. berghei* FER or FLP ORF (fer/flp) and the TgDHFR/Ts selectable marker. A XbaI-linearised plasmid is targeting the FER or FLP WT genomic locus, respectively, and inserts the selection marker and an additional truncated fer or flp copy.

Genotyping PCR of P. berghei Ferlin (FER) and Ferlin-like protein (FLP) knock-out or complementation transfectants are shown in C and D, respectively. Standard PCRs were run with ORF, test and episomal (epi) specific oligonucleotide pairs. As templates served gDNA of the different transfer transfectants (Δflp/Δfer/flpCONT/ferCONT) and P. berghei wild-type gDNA (WT) or respective targeting constructs (v) as PCR controls. Specific DNA fragments were separated by agarose gel electrophoresis.

Figure 14:
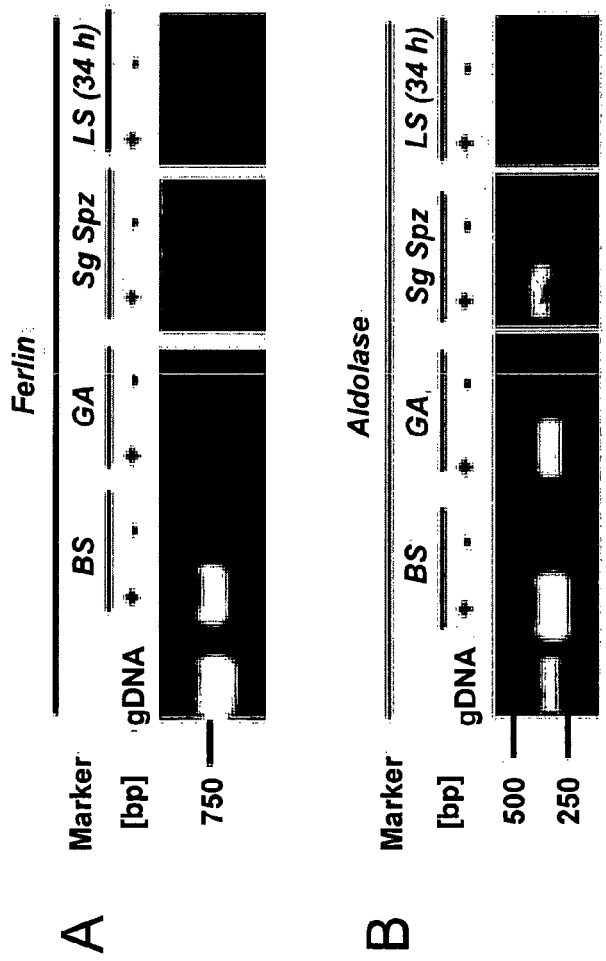

FIG. 14 shows an RT-PCR analysis of the transcriptional profile of P. berghei Ferlin (A) and the control enzyme Aldolase (B) throughout the malaria life cycle (BS=blood stage; GA=gametocytes; Sg Spz=salivary gland sporozoites; LS=liver stage).

The present invention is now further described by reference to the following examples, which are meant to illustrate, but not to limit the present invention.

Comparative Analysis of Early Plasmodium Liver Stages Identifies Potential Targets of Protective Immunity Genetically-attenuated parasites (GAP) arrest during liver stage (LS) development and therefore not all of the genes that are normally expressed during LS development will be expressed. Any genes that are expressed by the LS of wild-type (WT) sporozoites but not by the GAP can be assumed to be non-essential for initiation of a protective immune response. Thus analysing the repertoire of genes expressed by uis3(−) LS will allow to narrow down the antigens that are critical targets of pre-erythrocytic immunity.

Figure 1:
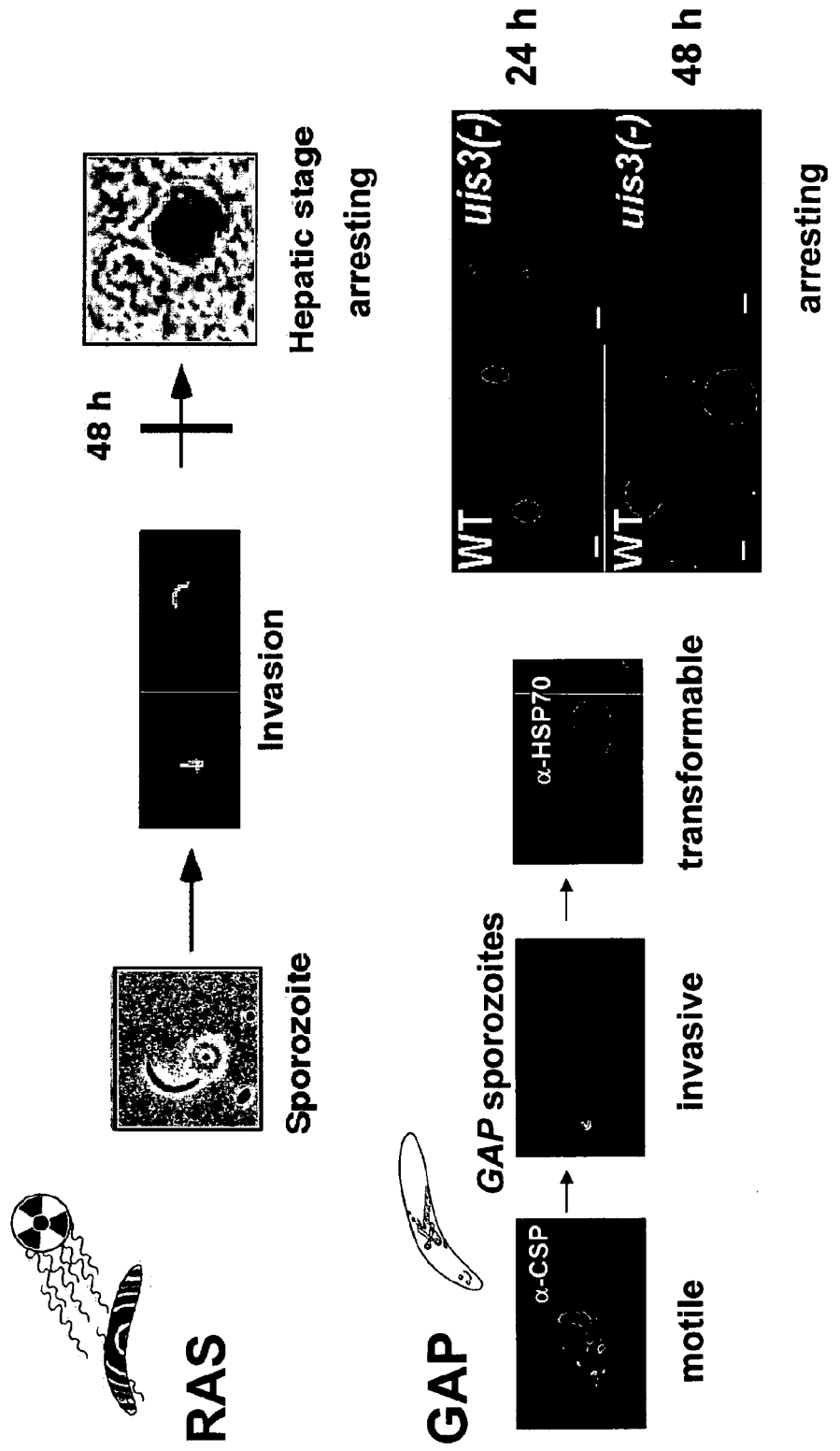
Figure 2:
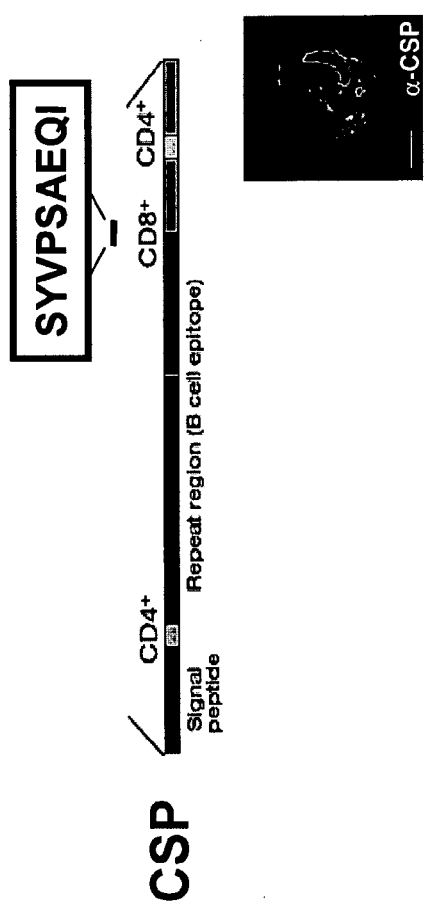
Figure 3:
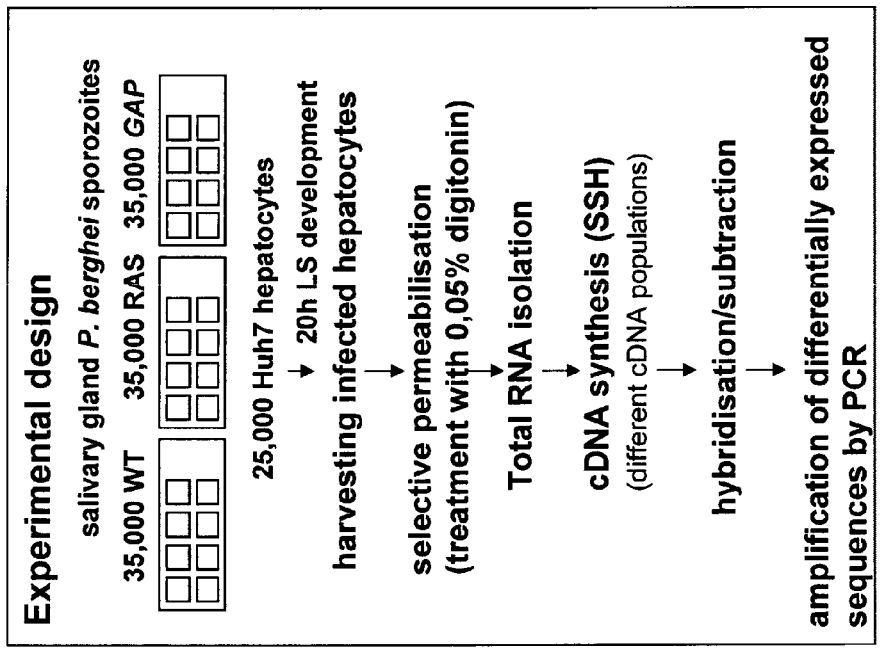
FIG. 3 shows the experimental setup of the modified suppression subtractive hybridisation (SSH) assay for comparing the transcripts of malarial WT, GAP and RAS parasites after 20 hours liver-stage development.

Suppression Subtractive Hybridisation Results in a Set of Specifically Upregulated Transcripts in Attenuated Parasites The inventors utilised suppression subtractive hybridisation (SSH) to compare the transcripts of WT, GAP and RAS parasites after 20 hours LS development (FIG. 3). This highly effective method allows to identify differentially expressed transcripts in two different cDNA populations (Diatchenko, 1996). LS development of Plasmodium parasites was achieved in cultivated hepatocytes. It is described that P. berghei sporozoites enter and transform in human hepatoma cells (Hollingdale, 1983). Therefore, the human hepatoma cell line Huh7 was used as an adequate host for LS development. This in vitro cultivation allowed to enhance the parasite to host cell ratio and therefore to gain sufficient RNA material for the subsequent subtraction. For one cDNA population of either GAP, RAS or WT LS, two to three 8-well chamber slides with 25,000 Huh7 cells and 25,000 to 35,000 sporozoites per well were inoculated and LS development was stopped after 20 h. This time point was chosen as uis3(−) parasites undergo arrested development in the liver after 24 hours and therefore already these early genes expressed during this period must be important for pre-erythrocytic immunity. Collected cells were treated with 0.05% Digitonin, which selectively permeabilized the host cell plasma membrane without affecting the intracellular parasite, and thus reduced contaminations with host cell RNA. Parasite specific RNA was subsequently isolated using the RNeasy Mini Kit (Qiagen). The RNA concentrations obtained reached from around 150 to 250 μg/ml in a volume of 40 μl, meaning final amounts of 6 to 10 μg total RNA. The cDNA synthesis with the applied SMART method (Clontech; SMART™ PCR cDNA Synthesis Kit, Protocol No. PT3041-1) requires 0.05 to 1 μg total RNA and therefore this technique was especially useful for this approach as starting material was limited. Around 0.5 μg total RNA was used for cDNA synthesis with the SMART technology and this cDNA was subsequently used for subtraction. The subtraction procedure was performed according to the manufacture's manual (Clontech; PCR-Select™ cDNA Subtraction Kit, Protocol No. PT1117-1). Resulting cDNA fragments were directly cloned into pGEMT-easy T/A-cloning vector (Promega) and sequenced with conventional methods.

Figure 4:
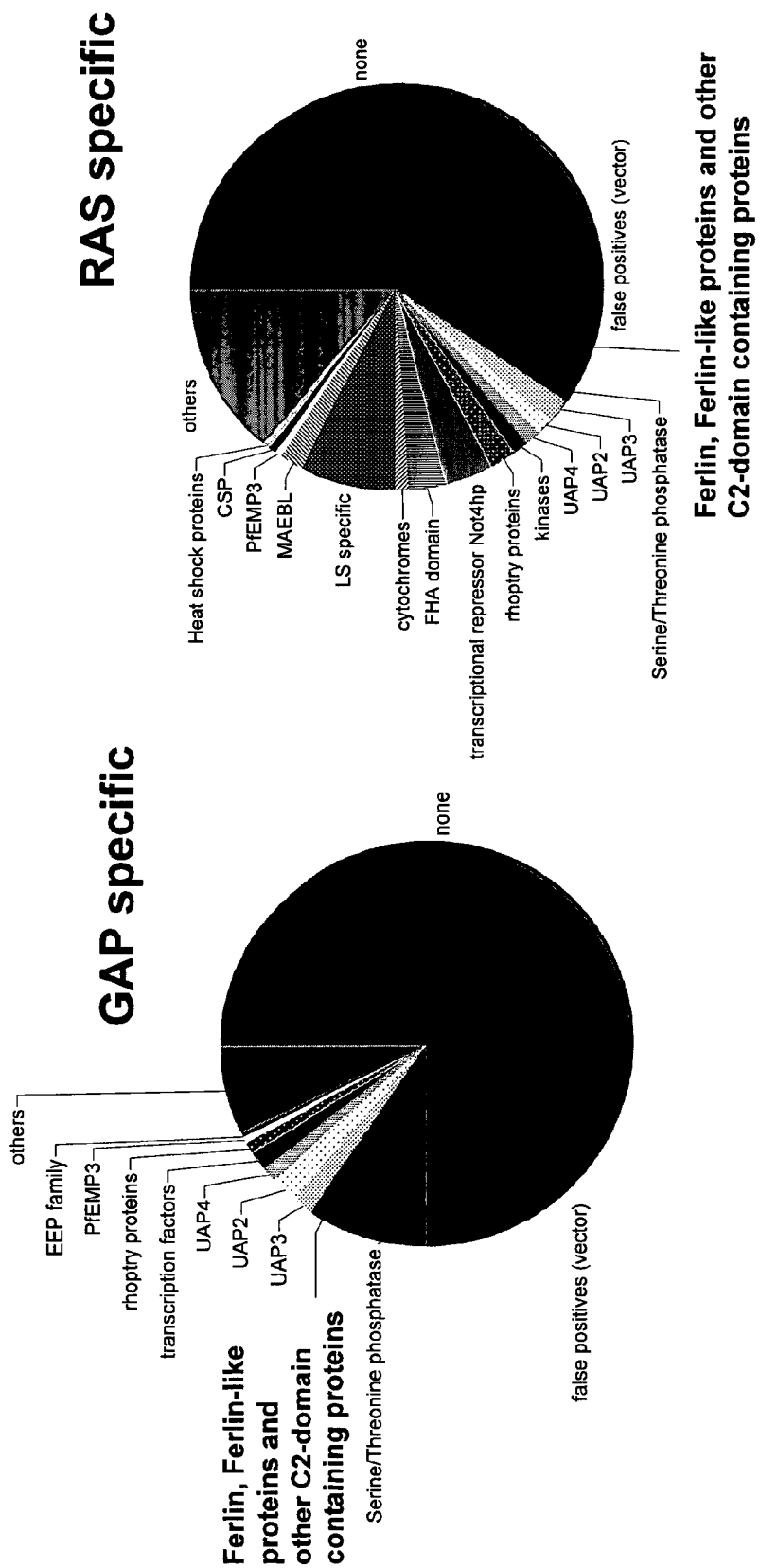
FIG. 4 shows the percentage of certain liver stage transcripts identified in 200 analysed sequences of genetically-attenuated (GAP-specific) or radiation-attenuated (RAS-specific) parasites compared to WT sequences by suppression subtractive hybridisation (SSH). Sequence analysis was performed using the BLAST search on the PlasmoDB and GeneDB homepages.

Sequences resulting from the SSH screen were searched by BLAST using the PlasmoDB database. Most of the prominent upregulated genes were shared between both attenuated parasite lines (FIG. 4). Among the most prominent genes were Ferlins, Ferlin-like proteins and C2-domain containing proteins as identified by the SMART database.

Figure 5A:
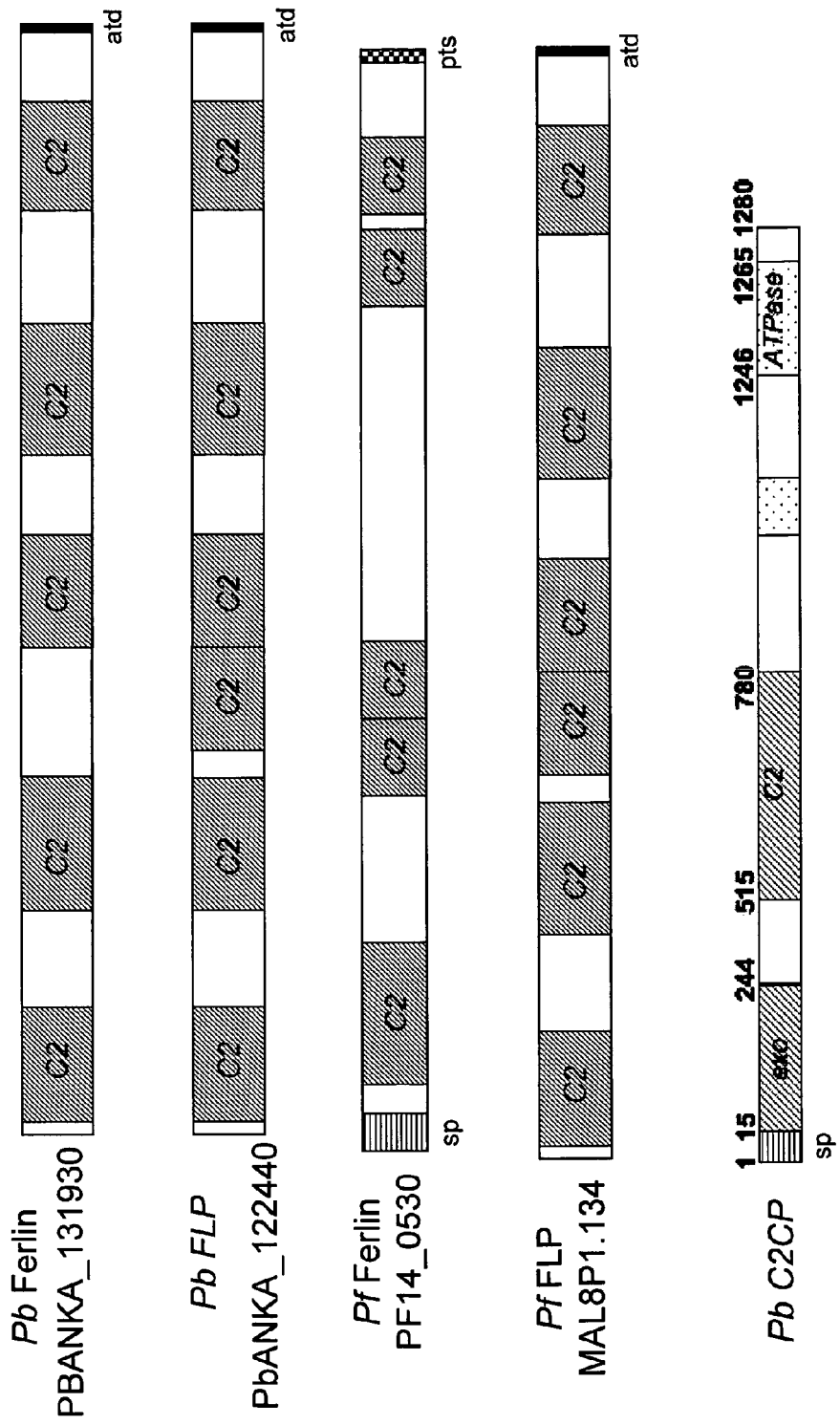
Figure 5B:
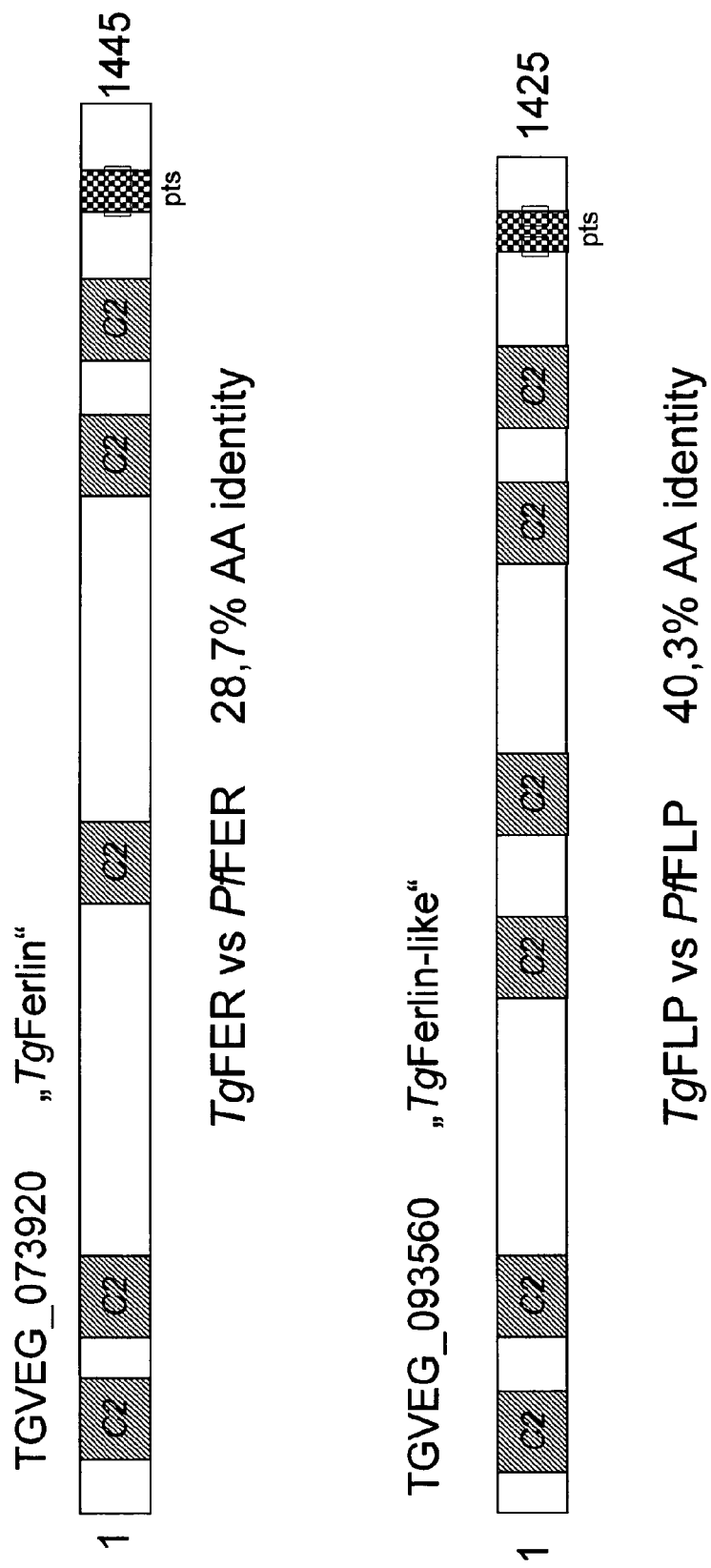

The primary structures of apicomplexan Ferlins, Ferlin-like proteins and Pb C2CP (PB402109.00.0) are shown in FIGS. 5A and B. There is the P. berghei Ferlin-like protein (PbANKA_122440) and one Pb Ferlin paralog (PBANKA_131930). In the P. falciparum genome, there is one Ferlin (PF14_0530) and one Ferlin-like protein (MAL8P1.134) annotated. Several Ferlins are annotated in the P. yoelii genome (not shown). Ferlin and FLP orthologs are also found in the apicomplexan parasite Toxoplasma gondii (FIG. 5B).

Ferlins and Ferlin-like proteins are membrane proteins with characteristic C2 domains in variable numbers. These domains are generally involved in $Ca^{2+}$-dependent lipid processing events. Ferlin family members share a conserved mechanism to regulate cell-type specific membrane fusion events (reviewed in Mc Neil et al., 2005). In Plasmodium the function of this protein family has not yet been characterised. The P. berghei C2-domain containing protein (C2CP) contains, beside one characteristic C2 domain, one domain with predicted exonuclease activity and one predicted ATPase domain. Moreover, all Ferlins and Ferlin-like proteins contain transmembrane domains, and N-terminal signal peptides are found in Pf Ferlin and Pb C2CP.

P. berghei C2CP

Example 1

The upregulation of P. berghei C2-domain containing protein (C2CP) in GAP and RAS liver stages was validated and quantified by quantitative real-time PCR (qRT-PCR) using gene-specific primers. As templates served P. berghei GAP, RAS and WT RNA isolated from liver stages after 20 hours LS development and transcribed in cDNA. FIG. 6 shows the copy numbers of mRNA of Pb C2CP in GAP, RAS and WT LS.

The potential of Pb C2CP as antigen candidate became apparent when four predicted H-2b restricted CD8+ T cell epitopes were detected with the help of several prediction programs, including the epitope prediction program SYFPEITHI (FIG. 7A). The amino acid sequences of the predicted Pb C2CP CD8+ T cell epitopes A9I, T9L, S8V, and A8I are shown in Table 1.

TABLE 1

| Predicted CD8+ T cell epitopes of Pb C2CP. | | |
|---|---|---|
| Sequence | Abbreviation | Position |
| A Y I A P H T I I (SEQ ID NO: 22) | A9I | 141-149 |
| T I R S F Y K R L (SEQ ID NO: 23) | T9L | 417-425 |
| S P Y L F N I V (SEQ ID NO: 24) | S8V | 671-678 |
| A I Y R F N A I (SEQ ID NO: 25) | A8I | 827-834 |

For immunological studies, immunisations of mice with GAP (uis3(−)) and RAS were performed according to the prime-two-boost protocol (FIG. 7B).

An in vivo cytotoxicity assay was performed in order to shed light on the capacity of GAP and RAS immunised animals to recognise and kill cells that carry Pb C2CP-derived epitopes on their surface. A pool of the four predicted CD8+ T cell epitopes A9I, T9L, S8V and A8I was loaded on CFSE-labeled splenocytes and injected into immunised mice together with a control cell population that carried no epitopes and was labeled with a lower concentration of CFSE. Mice were sacrificed 18 hours later and liver lymphocytes and splenocytes were isolated. Some of these cells were directly measured by flow cytometry where the CFSE-labeled cells can be seen in the FL1 channel of the BD FACSCalibur (excitation 488 nm, emission 517 nm). The percentage of specifically lysed cells was calculated with the following mathematical function:

$$\text{specific lysis [\%]} = 100 - \frac{(\text{ratio } CFSE^{high}/CFSE^{low} \text{ sample})}{(\text{mean ratio } CFSE^{high}/CFSE^{low} \text{ naive controls})} * 100$$

The percentages of specifically lysed cells in spleens and livers of RAS and GAP immunised mice 7 days after a subsequent WT challenge is shown in FIG. 8. There was no specific cytotoxic lysis detected in the spleen of immunised animals. In the livers of RAS and GAP immunised mice, however, 11.8% and 19.6% Pb C2CP-specific cells, respectively, get lysed. This is significantly more than in naive control animals were on average less than 0.001% of the fluorescently labeled Pb C2CP-specific cells get lysed. In WT challenged mice also 10.5% of the Pb C2CP-specific are killed. These mice had seen *P. berghei* WT liver stages before but in contrast to immunised mice they had developed a blood stage infection. These results demonstrate that Pb C2CP-specific cells get indeed recognised and killed in immunised or exposed animals. Immune mechanisms directed against the Pb C2CP-derived epitopes could be detected.

To decipher Pb C2CP-specific immune responses in RAS and GAP immunised animals in more detail, the single peptide T9L was used for restimulation in the following experiments. The epitope T9L was chosen because it had the highest predicted binding affinity to H2b. Staining for surface activation marker of restimulated lymphocytes from GAP and RAS immunised mice showed a clearly enhanced effector memory T cell population ($T_{EM}$; CD8+CD44$^{high}$CD62L$^{low}$) in comparison to naive mice (FIG. 9). Mean percentages of $T_{EM}$ cells of 42.4% in livers of naive mice, increased significantly to 71.5% in RAS immunised and to 65.1% in GAP immunised animals (p<0.0001 and p=0.058; unpaired t test). The $T_{EM}$ cell population additionally expressed the surface marker CD25 (not shown). This further indicates that specific effector mechanisms are present against Pb C2CP in RAS and GAP immunised animals.

ELISpot (Enzyme-linked immunosorbent spot), an extremely sensitive assay that allows the detection of cytokines on the single cell level, was applied in order to measure low IFN-γ responses in the livers and spleens of RAS and GAP immunised mice. Purified liver lymphocytes or total splenocytes from immunised mice were restimulated over night with the Pb C2CP-derived peptide T9L. Prior to the transfer of restimulated cells to IFN-γ coated MultiScreen filter plates, the culture medium was replaced with fresh medium to dilute secreted IFN-γ in the culture supernatant and to reduce background. After 24 hours incubation of the stimulated cells on filter plates, spots were detected by a secondary biotinylated anti IFN-γ antibody. Every spot that developed on the membrane represented a single reactive cell. Spots were counted under a dissection microscope. Controls for the stimulated cells from immunised animals were cells incubated without stimulus and cells isolated from naive animals. A positive control, naive lymphocytes activated with an anti-CD3 antibody, was run along to prove that the assay is working.

The IFN-γ responses of restimulated splenocytes after GAP and RAS immunisation where very low (FIG. 10). Unfortunately, the anti-CD3 positive control was also unexpectedly low, with only a mean of 168 spots per million total splenocytes. However, the IFN-γ response increased significantly in spleens of GAP immunised C57Bl/6 mice when restimulated with the Pb C2CP-derived peptide T9L (p=0.0346; unpaired t test). The IFN-γ responses of purified liver lymphocytes where in total higher than those of the splenocytes suggesting more activated T cells in the liver where the parasite infection occurs. When specifically restimulating liver lymphocytes from GAP immunised animals with Pb C2CP-derived peptide T9L, the responses of 622 reactive cells, from RAS immunised animals even 825 responding lymphocytes per million cells were detected. As control, unspecific stimulation of naive cells with anti-CD3 antibody resulted in on average 681 reactive cells per one million liver lymphocytes. Unfortunately, also the unstimulated background was quite high, so that significant increase after restimulation was only detectable in livers from RAS immunised mice (p=0.0446; unpaired t test). These results showed, that T cells from GAP and RAS immunised C57Bl/6 mice can indeed be specifically restimulated with at least one Pb C2CP-derived epitope.

*P. falciparum* Ferlin

Example 2

The upregulation of *P. falciparum* Ferlin (Pf FER) in RAS liver stages was validated and quantified by quantitative real-time PCR (qRT-PCR) using gene-specific primers. FIG. 11B shows the relative transcript levels of *P. falciparum* Ferlin (Pf FER).

Six predicted HLA-A 0201-restricted CD8+ T cell epitopes were detected with the help of several prediction programs, including the epitope prediction program SYFPEITHI (FIG. 11 A).

In order to investigate the presence of Pf Ferlin-specific T cells in malaria-exposed individuals, T-cell responses to Pf Ferlin peptides (NLLDPLVVV (SEQ ID NO:4), YLYVNIHKI (SEQ ID NO:5), LLLEGNFYL (SEQ ID NO:6), KLIPVNYEL (SEQ ID NO:7), YLYEKQQEL (SEQ ID NO:8), ILIPSLPLI (SEQ ID NO:9)) were tested in semi-immune Kenyan adults in collaboration with Dr. Britta urban at the Kenyan Medical Research Institute-Wellcome Trust Research Programme (KEMRI). All adults are resident in Junju District, about 60 km north of Mombasa at the Kenyan coast. The area has two high transmission seasons but low-level transmission occurs all year round (infectious bites per year:23-53) (Mwangi et al., 2005).

Figure 12:
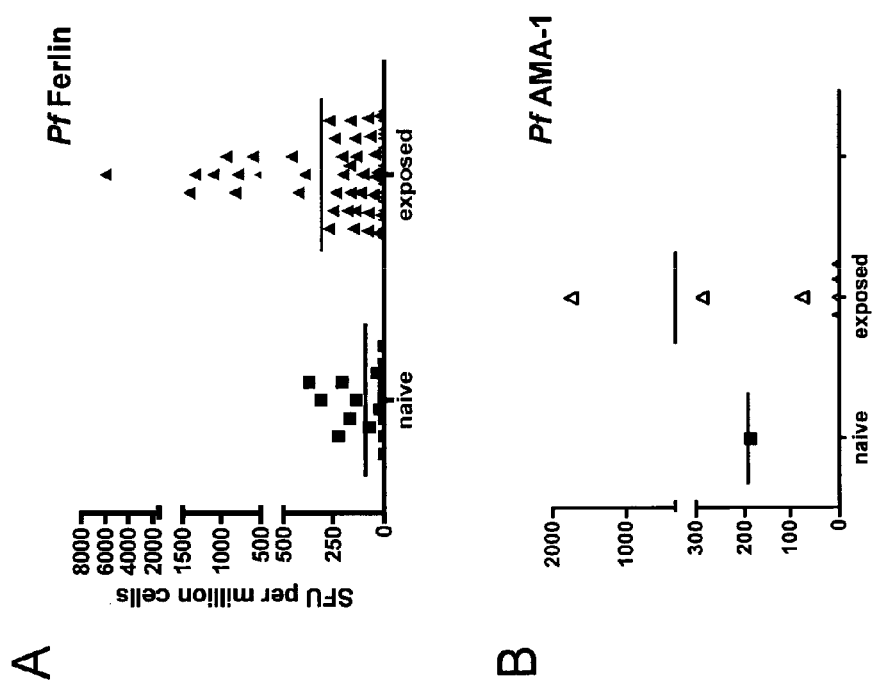

In order to determine the production of antigen-specific IFNγ by activated peripheral blood mononuclear cells (PBMC), cultured ELISpot analysis was carried out over a period of 10 days in malaria-exposed adults and malaria-naïve individuals. Interestingly, activated Ferlin-specific T cells could be detected (FIG. 12). Furthermore, when studying the production of antigen-specific IFN-γ by activated peripheral blood mononuclear cells (PBMC) in 12 malaria-exposed adults and 5 malaria-naive individuals, Pf Ferlin-specific T cells were detected to at least one peptide in 4 out of 12 and to more than one peptide in 3 out of 12 malaria-exposed adults (Table 2).

injected intravenously (i.v.) into NMRI mice. Parasitemia was checked by a giemsa-stained blood smear on day 1 after transfection. Starting parasitemias were quite low with 0.1% to 0.3% for three independent experiments. From day 1 pyrimethamine was provided with the drinking water to select for transfected parasites. On day 2 parasitemias decreased to undetectable levels in giemsa-stained blood smears. Under

TABLE 2

Summary of all tested individuals and their response to individual peptide fragments of Pf Ferlin. An INFγ response above SFC 500 identified the patient as a responder.

| Patient # | Epitope 1 NLLDPLVVV (SEQ ID NO: 4) | Epitope 2 YLYVNIHKI (SEQ ID NO: 5) | Epitope 3 LLLEGNFYL (SEQ ID NO: 6) | Epitope 4 KLIPVNYEL (SEQ ID NO: 7) | Epitope 5 YLYEKQQEL (SEQ ID NO: 8) | Epitope 6 ILIPSLPLI (SEQ ID NO: 9) |
|---|---|---|---|---|---|---|
| JA006 | no | no | no | no | no | N/D |
| JA029 | yes | yes | yes | no | no | no |
| JA046 | no | no | no | no | no | no |
| JA066 | no | no | no | no | N/D | no |
| JA086 | no | no | yes | yes | no | no |
| JA007 | no | N/D | N/D | no | N/D | N/D |
| JA030 | no | no | no | yes | yes | yes |
| JA047 | no | no | no | no | no | no |
| JA067 | no | no | no | no | N/D | no |
| JA087 | no | N/D | N/D | N/D | N/D | N/D |
| Ad | yes | no | no | no | no | no |
| Fr | no | no | no | no | no | no |

Functional Characterisation of Ferlins and Ferlin-Like Proteins

In order to functionally characterise the *P. berghei* Ferlin (FER) and Ferlin-like protein (FLP) a targeted gene depletion was performed, since the resulting depletion phenotypes may suggest potential functions of the protein. Targeted gene depletion in *Plasmodium* is conducted in blood stage parasites. Therefore genes essential during blood stage development cannot be targeted. A failing integration of the targeting construct, however, can also be due to poor accessibility of the genomic locus for homologous recombination. Therefore, a knock-out construct and a complementation construct for Pb FER and Pb FLP were generated, that were transfected separately during the same experiment.

The different genetic strategies are shown in FIGS. 13A and B. For the knock-out targeting construct two fragments from the 5' and 3' untranslated regions (UTR) of the respective gene were amplified with specific oligonucleotides. Expected fragments sizes were confirmed by agarose gel electrophoresis. The Pb FER fragments were 676 bp and 773 bp for the 5' and the 3' UTR fragment, respectively, the Pb FLP fragments had a length of 678 bp and 612 bp, respectively (not shown). The two corresponding fragments were cloned into the targeting vector b3D as described, flanking the TgDHFR/TS selectable marker, resulting in the constructs pΔfer and pΔflp. For the control complementation constructs C-terminal fragments including the stop codon were amplified in two parts to insert a unique restriction site necessary for linearization prior to transfection. The sizes of 952 bp and 744 bp for the Pb FER complementation and of 497 bp and 481 bp for the Pb FLP complementation, respectively, were again confirmed by agarose gel electrophoresis (not shown). Cloning of two corresponding fragments one after another into the cloning vector b3D+ resulted in the complementation constructs pferCONT and pflpCONT.

The *P. berghei* ANKA GFPcon strain (Franke-Fayard, 2004) was transfected with the KpnI/XbaI digested Δfer and Δflp constructs, as well as with the XbaI-linearised constructs ferCONT and flpCONT according to the described AMAXA transfection protocol. Transfected merozoites were directly continuous drug selection resistant parasites first appeared from day 7 to 9 in the blood. Resistant parasites transfected with the knock-out constructs took on average 9 days for Δflp and 8.5 days for Δfer until detectable in thin blood smears. Parasites transfected with the complementation constructs, ferCONT and flpCONT, were slightly faster and respective mice got blood stage positive on average 7.5 days after transfection. As soon as parasite levels in the blood increased to 0.5% to 1%, mice were sacrificed. Infected blood was saved as cryo stock and isolated parasites were kept as parental populations for genomic DNA (gDNA). Around 50 to 100 µl infected blood was transferred intraperitonealy (i.p.) into naive NMRI mice and parasitemia was again monitored under drug pressure. Upcoming parasites were again collected from infected blood and kept as transfer population. Transfectants were checked by specific PCRs for integration of the targeting constructs (FIGS. 13C and D).

Specific oligonucleotide pairs ORF I and ORF II amplified different parts of the Pb FER or Pb FLP open-reading frames. For the knock-out genotyping PCR, the DNA fragments amplified with ORF I oligonucleotides were expected to be 978 bp for Pb FLP and 1696 bp for Pb FER. Respective bands could be seen on a agarose gel when using WT gDNA or Δflp/Δfer gDNA as PCR templates (FIG. 13C). As expected there was no ORF I specific DNA fragment amplified when the targeting knock-out constructs were used as a template. The episomal specific oligonucleotide pairs epi I and epi II amplify vector specific fragments. Therefore epi I specific DNA bands, with the expected sizes of 1165 bp and 1326 bp for Pb FLP and Pb FER, respectively, could be detected on a agarose gel when using respective targeting constructs, pΔflp and pΔfer, as a template as well as the gDNA of resistant transfectants, Δflp and Δfer, that carry the plasmids. Test oligonucleotide pairs test I and II proved integration of the targeting constructs into the parasite genome and could therefore only be amplified from gDNA of positive transfectants. The expected test I specific DNA fragments with sizes of 1301 bp and 1557 bp could not be amplified from the transfectants gDNA indicating no integration of the targeting constructs, pΔflp and pΔfer, and therefore no depletion of the respective genes, Pb FLP and Pb FER. That looked differently for the control complementation genotyping PCR (FIG. 13D). ORF II specific DNA fragments having a size of 978 bp or 1068 bp could be visualised on a agarose gel when using WT gDNA or gDNA of the transfectants flpCONT and fer-CONT as templates and not be amplified from the CONT complemenation constructs. Epi II specific DNA bands could be detected on a agarose gel with a size of 1478 bp and 2196 bp, respectively, for transfectants' gDNA and vector control only. The test II specific DNA fragments with sizes of 2879 bp for flpCONT and 4304 bp for ferCONT demonstrated a successful integration of the control complementation constructs, pflpCONT and pferCONT. By that the accessibility of both genomic loci could be proven. Same genotyping results were achieved from three independent transfection experiments.

These results showing that *P. berghei* Ferlin and Ferlin-like protein are essential during blood stage development were also confirmed by RT-PCR analysis of the transcriptional profile of *P. berghei* Ferlin throughout the malaria life cycle (FIG. 14).

The features disclosed in the foregoing description, in the claims and/or in the accompanying drawings may, both separately and in any combination thereof, be material for realising the invention in diverse forms thereof.

REFERENCES

Diatchenko L, Lau Y F, Campbell A P, Chenchik A, Moqadam F, Huang B, Lukyanov S, Lukyanov K, Gurskaya N, Sverdlov E D, Siebert P D (1996). Suppression subtractive hybridization: a method for generating differentially regulated or tissue-specific cDNA probes and libraries. Proc Natl Acad Sci USA. 93(12):6025-30.

Franke-Fayard B, Trueman H, Ramesar J, Mendoza J, van der Keur M, van der Linden R, Sinden R E, Waters A P, Janse C J (2004). A *Plasmodium berghei* reference line that constitutively expresses GFP at a high level throughout the complete life cycle. Mol Biochem Parasitol. 137(1):23-33.

Hollingdale M R, Leland P, Schwartz A L (1983). In vitro cultivation of the exoerythrocytic stage of *Plasmodium berghei* in a hepatoma cell line. Am J Trop Med Hyg. 32(4):682-4.

McNeil, P. L., Kirchhausen, T (2005). An emergency response team for membrane repair. Nat Rev Mol Cell Biol 6:499-505.

Mwangi, T. W., Ross, A., Snow, R. W., Marsh, K (2005). Case definitions of clinical malaria under different transmission conditions in Kilifi District, Kenya. J Infect Dis 191:1932-9.

The invention claimed is:

1. A composition comprising
   (i) at least one isolated peptide comprising at least one antigenic determinant or epitope of an apicomplexan protein selected from Ferlin and members of the Ferlin-like protein family,
      wherein the antigenic determinant or epitope is at least 8 amino acids in length, and
   (ii) an adjuvant, and
   (iii) optionally, a carrier.

2. The composition according to claim 1, comprising at least two peptides.

3. The composition according to claim 1, comprising a carrier wherein the carrier is a virus particle or a part thereof, an envelope protein of a viral vector or of a virus particle, or a nanocarrier.

4. The composition according to claim 3, wherein the virus particle is a Hepatitis B virus particle.

5. The composition according to claim 3, wherein the nanocarrier is a cell-targeted nanocarrier.

6. The composition according to claim 1, wherein the adjuvant triggers a CD8 T cell response.

7. A composition comprising:
   at least two antigenic determinants or epitopes, wherein each of said antigenic determinants or epitopes is an isolated antigenic determinant or epitope of *Plasmodium falciparum* Ferlin (Pf FER) or a *Plasmodium falciparum* Ferlin-like protein (Pf FLP), wherein the composition further comprises an adjuvant.

8. The composition according to claim 7, wherein the amino acid sequences of said at least two antigenic determinants or epitopes are selected from:

```
(N9V)    N L L D P L V V V,        [SEQ ID NO. 4]
(Y9I)    Y L Y V N I H K I,        [SEQ ID NO. 5]
(L9L)    L L L E G N F Y L,        [SEQ ID NO. 6]
(K9L)    K L I P V N Y E L,        [SEQ ID NO. 7]
(Y9L)    Y L Y E K Q Q E L,        [SEQ ID NO. 8]
(I9I)    I L I P S L P L I,        [SEQ ID NO. 9]
(T9L)    T L N P L L P W L,        [SEQ ID NO. 14]
(I9L)    I L I K S E A E L,        [SEQ ID NO. 15]
(N9V)    N I L E P Y V K V,        [SEQ ID NO. 16]
(Y9L)    Y L Y G G R I F L,        [SEQ ID NO. 17]
(L10V)   L L V A F E L V P V,      [SEQ ID NO. 18]
(L10L)   L L I G T A Y I T L,      [SEQ ID NO. 19]
(D10L)   D L M P I E L R S L,      [SEQ ID NO. 20]
  and
(A10L)   A L I G K C S F G L.      [SEQ ID NO. 21]
```

9. The composition according to claim 7, comprising a peptide that comprises both a first antigenic determinant or epitope and a second antigenic determinant or epitope.

10. The composition according to claim 7, comprising a first peptide that comprises the first antigenic determinant or epitope and a second peptide that comprises the second antigenic determinant or epitope.

11. The composition according to claim 7, comprising at least two peptides each comprising one of said antigenic determinants or epitopes.

12. The composition according to claim 7, wherein at least one of the proteins is selected from
*Plasmodium berghei* Ferlin (Pb FER) (SEQ ID NO:26, 
*Plasmodium falciparum* Ferlin (Pf FER) (SEQ ID NO:27, 
*Plasmodium yoelii* Ferlin (Py FER) (SEQ ID NO:28, 
*Toxoplasma gondii* Ferlin (Tg FER) (SEQ ID NO:29,

*Plasmodium berghei* Ferlin-like protein (Pb FLP) (SEQ ID NO:30,
*Plasmodium falciparum* Ferlin-like protein (Pf FLP) (SEQ ID NO:31,
*Plasmodium yoelii* Ferlin-like protein (Py FLP) (SEQ ID NO:32,
*Toxoplasma gondii* Ferlin-like protein (Tg FLP) (SEQ ID NO:33,
*Plasmodium berghei* C2-domain containing protein (Pb C2CP) (SEQ ID NO:34, and variants of the above proteins that are at least 95% identical to one of the above proteins.

13. The composition according to claim 7, wherein at least one of the antigenic determinants or epitopes is a CD8+ T cell epitope, a CD4+ T cell epitope or a B cell epitope.

14. The composition according to claim 7, wherein the amino acid sequence of one of the antigenic determinants or epitopes is selected from

```
                                         [SEQ ID NO. 1]
    (P8L)  P N P N F S Y L,

[SEQ ID NO. 2]
    (V8L)  V P I E Y R P L,
    and
                                         [SEQ ID NO. 3]
    (L8L)  L N T C F L Q L.
```

15. The composition according to claim 7, wherein the amino acid sequence of one of the antigenic determinants or epitopes is selected from

```
                                         [SEQ ID NO. 4]
    (N9V)  N L L D P L V V V,

[SEQ ID NO. 5]
    (Y9I)  Y L Y V N I H K I,

[SEQ ID NO. 6]
    (L9L)  L L L E G N F Y L,

[SEQ ID NO. 7]
    (K9L)  K L I P V N Y E L,

[SEQ ID NO. 8]
    (Y9L)  Y L Y E K Q Q E L,
    and
                                         [SEQ ID NO. 9]
    (I9I)  I L I P S L P L I.
```

16. The composition according to claim 7, wherein the amino acid sequence of one of the antigenic determinants or epitopes is selected from

```
                                         [SEQ ID NO. 10]
    (S8L)  S R Y F F R A L,

[SEQ ID NO. 11]
    (L8V)  L N Y V Y S K V,

[SEQ ID NO. 12]
    (I8M)  I G Y T Y I D M,
``` and

```
                                         [SEQ ID NO. 13]
    (V8L)  V G T A Y I T L.
```

17. The composition according to claim 7, wherein the amino acid sequence of one of the antigenic determinants or epitopes is selected from

```
                                         [SEQ ID NO. 14]
    (T9L)  T L N P L L P W L,

[SEQ ID NO. 15]
    (I9L)  I L I K S E A E L,

[SEQ ID NO. 16]
    (N9V*) N I L E P Y V K V,

[SEQ ID NO. 17]
    (Y9L)  Y L Y G G R I F L,

[SEQ ID NO. 18]
    (L10V) L L V A F E L V P V,

[SEQ ID NO. 19]
    (L10L) L L I G T A Y I T L,

[SEQ ID NO. 20]
    (D10L) D L M P I E L R S L,
    and
                                         [SEQ ID NO. 21]
    (A10L) A L I G K C S F G L.
```

18. The composition according to claim 7, wherein the amino acid sequence of one of the antigenic determinants or epitopes is selected from

```
                                         [SEQ ID NO. 22]
    (A9I)  A Y I A P H T I I,

[SEQ ID NO. 23]
    (T9L)  T I R S F Y K R L,

[SEQ ID NO. 24]
    (S8V)  S P Y L F N I V,
    and
                                         [SEQ ID NO. 25]
    (A8I)  A I Y R F N A I.
```

19. The composition according to claim 7, wherein the peptide further comprises at least one antigenic determinant or epitope of an apicomplexan protein different from Ferlin and members of the Ferlin-like protein family.

20. The composition according to claim 7, wherein each of said isolated antigenic determinants or epitopes is 8 to 25 amino acids in length.

21. The composition according to claim 20, wherein each of said isolated antigenic determinants or epitopes is 8 to 15 amino acids in length.

22. A method for raising an immune response against malaria, wherein said method comprises administering, to a subject in need of such immune response, a composition of claim 7.

* * * * *

UNITED STATES PATENT AND TRADEMARK OFFICE
CERTIFICATE OF CORRECTION

PATENT NO.        : 8,968,750 B2                                   Page 1 of 1
APPLICATION NO.   : 13/513059
DATED             : March 3, 2015
INVENTOR(S)       : Ann-Kristin Müller It is certified that error appears in the above-identified patent and that said Letters Patent is hereby corrected as shown below:

In the Specification

Column 3,
Line 66, "CD 8+ T cell epitope" should read --CD8+ T cell epitope--.

Column 7,
Line 9, "(H2 Kd)" should read --(H2Kd)--.

Column 12,
Line 56, "Dr. Britta urban" should read --Dr. Britta Urban--.

In the Claims

Column 100,
Line 16, Claim 17 "(N9V*)" should read --(N9V)--.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 36

<210> SEQ ID NO 1
<211> LENGTH: 8
<212> TYPE: PRT
<213> ORGANISM: Plasmodium berghei

<400> SEQUENCE: 1

Pro Asn Pro Asn Phe Ser Tyr Leu
1               5

<210> SEQ ID NO 2
<211> LENGTH: 8
<212> TYPE: PRT
<213> ORGANISM: Plasmodium berghei

<400> SEQUENCE: 2

Val Pro Ile Glu Tyr Arg Pro Leu
1               5

<210> SEQ ID NO 3
<211> LENGTH: 8
<212> TYPE: PRT
<213> ORGANISM: Plasmodium berghei

<400> SEQUENCE: 3

Leu Asn Thr Cys Phe Leu Gln Leu
1               5

<210> SEQ ID NO 4
<211> LENGTH: 9
<212> TYPE: PRT
<213> ORGANISM: Plasmodium falciparum

<400> SEQUENCE: 4

Asn Leu Leu Asp Pro Leu Val Val Val
1               5
```

-continued

```
<210> SEQ ID NO 5
<211> LENGTH: 9
<212> TYPE: PRT
<213> ORGANISM: Plasmodium falciparum

<400> SEQUENCE: 5

Tyr Leu Tyr Val Asn Ile His Lys Ile
1               5

<210> SEQ ID NO 6
<211> LENGTH: 9
<212> TYPE: PRT
<213> ORGANISM: Plasmodium falciparum

<400> SEQUENCE: 6

Leu Leu Leu Glu Gly Asn Phe Tyr Leu
1               5

<210> SEQ ID NO 7
<211> LENGTH: 9
<212> TYPE: PRT
<213> ORGANISM: Plasmodium falciparum

<400> SEQUENCE: 7

Lys Leu Ile Pro Val Asn Tyr Glu Leu
1               5

<210> SEQ ID NO 8
<211> LENGTH: 9
<212> TYPE: PRT
<213> ORGANISM: Plasmodium falciparum

<400> SEQUENCE: 8

Tyr Leu Tyr Glu Lys Gln Gln Glu Leu
1               5

<210> SEQ ID NO 9
<211> LENGTH: 9
<212> TYPE: PRT
<213> ORGANISM: Plasmodium falciparum

<400> SEQUENCE: 9

Ile Leu Ile Pro Ser Leu Pro Leu Ile
1               5

<210> SEQ ID NO 10
<211> LENGTH: 8
<212> TYPE: PRT
<213> ORGANISM: Plasmodium berghei

<400> SEQUENCE: 10

Ser Arg Tyr Phe Phe Arg Ala Leu
1               5

<210> SEQ ID NO 11
<211> LENGTH: 8
<212> TYPE: PRT
<213> ORGANISM: Plasmodium berghei

<400> SEQUENCE: 11

Leu Asn Tyr Val Tyr Ser Lys Val
1               5

<210> SEQ ID NO 12
<211> LENGTH: 8
```

```
<212> TYPE: PRT
<213> ORGANISM: Plasmodium berghei

<400> SEQUENCE: 12

Ile Gly Tyr Thr Tyr Ile Asp Met
1               5

<210> SEQ ID NO 13
<211> LENGTH: 8
<212> TYPE: PRT
<213> ORGANISM: Plasmodium berghei

<400> SEQUENCE: 13

Val Gly Thr Ala Tyr Ile Thr Leu
1               5

<210> SEQ ID NO 14
<211> LENGTH: 9
<212> TYPE: PRT
<213> ORGANISM: Plasmodium falciparum

<400> SEQUENCE: 14

Thr Leu Asn Pro Leu Leu Pro Trp Leu
1               5

<210> SEQ ID NO 15
<211> LENGTH: 9
<212> TYPE: PRT
<213> ORGANISM: Plasmodium falciparum

<400> SEQUENCE: 15

Ile Leu Ile Lys Ser Glu Ala Glu Leu
1               5

<210> SEQ ID NO 16
<211> LENGTH: 9
<212> TYPE: PRT
<213> ORGANISM: Plasmodium falciparum

<400> SEQUENCE: 16

Asn Ile Leu Glu Pro Tyr Val Lys Val
1               5

<210> SEQ ID NO 17
<211> LENGTH: 9
<212> TYPE: PRT
<213> ORGANISM: Plasmodium falciparum

<400> SEQUENCE: 17

Tyr Leu Tyr Gly Gly Arg Ile Phe Leu
1               5

<210> SEQ ID NO 18
<211> LENGTH: 10
<212> TYPE: PRT
<213> ORGANISM: Plasmodium falciparum

<400> SEQUENCE: 18

Leu Leu Val Ala Phe Glu Leu Val Pro Val
1               5                   10

<210> SEQ ID NO 19
<211> LENGTH: 10
<212> TYPE: PRT
<213> ORGANISM: Plasmodium falciparum
```

<400> SEQUENCE: 19

Leu Leu Ile Gly Thr Ala Tyr Ile Thr Leu
1               5                   10

<210> SEQ ID NO 20
<211> LENGTH: 10
<212> TYPE: PRT
<213> ORGANISM: Plasmodium falciparum

<400> SEQUENCE: 20

Asp Leu Met Pro Ile Glu Leu Arg Ser Leu
1               5                   10

<210> SEQ ID NO 21
<211> LENGTH: 10
<212> TYPE: PRT
<213> ORGANISM: Plasmodium falciparum

<400> SEQUENCE: 21

Ala Leu Ile Gly Lys Cys Ser Phe Gly Leu
1               5                   10

<210> SEQ ID NO 22
<211> LENGTH: 9
<212> TYPE: PRT
<213> ORGANISM: Plasmodium berghei

<400> SEQUENCE: 22

Ala Tyr Ile Ala Pro His Thr Ile Ile
1               5

<210> SEQ ID NO 23
<211> LENGTH: 9
<212> TYPE: PRT
<213> ORGANISM: Plasmodium berghei

<400> SEQUENCE: 23

Thr Ile Arg Ser Phe Tyr Lys Arg Leu
1               5

<210> SEQ ID NO 24
<211> LENGTH: 8
<212> TYPE: PRT
<213> ORGANISM: Plasmodium berghei

<400> SEQUENCE: 24

Ser Pro Tyr Leu Phe Asn Ile Val
1               5

<210> SEQ ID NO 25
<211> LENGTH: 8
<212> TYPE: PRT
<213> ORGANISM: Plasmodium berghei

<400> SEQUENCE: 25

Ala Ile Tyr Arg Phe Asn Ala Ile
1               5

<210> SEQ ID NO 26
<211> LENGTH: 1897
<212> TYPE: PRT
<213> ORGANISM: Plasmodium berghei

<400> SEQUENCE: 26

```
Met Arg Val Ile Ser Val Gly Phe Ile Ile Tyr Glu Ala Gln Asn Leu
1               5                   10                  15

Lys Val Glu Asp Lys Glu Leu Leu Asp Pro Leu Val Val Arg Cys
            20                  25                  30

Cys Asn Asn Glu Tyr Ile Thr Lys Lys Lys Lys Tyr Asn Ala
            35                  40                  45

Val Asn Trp Glu Glu Ser His Val Trp Asn Arg Ile Val Leu Ser Glu
    50                  55                  60

Ile Glu Trp Asn Val Ala Lys Ile Glu Phe Glu Val Gln Ser Ala Asn
65                  70                  75                  80

Thr Phe Trp Arg Asn Asp Val Ile Gly Val Ile Ser Phe Glu Leu Lys
                85                  90                  95

Leu Ile Arg Asn Lys Lys Asn His Gln Ile Tyr Gly Thr Tyr Pro Ile
                100                 105                 110

Leu Tyr Lys Asn Arg Thr Glu Ile Gln Gly Gln Leu Arg Leu Lys Val
        115                 120                 125

Ile Val Cys Asn Glu Asn Asp Tyr Thr Ser Ser Glu Ile Tyr Ser
        130                 135                 140

Ser Leu Ala Gln Tyr Asn Asn Thr Asn Asn Asn Asp Asn Asn
145                 150                 155                 160

Asn Ser Asp Asn Glu Asn Phe Tyr Glu Asp Leu Thr Lys Ala Val Val
                165                 170                 175

Glu Glu Asn Thr Ile Ala Leu Arg Asp Val Asn Ser Arg Phe Tyr Tyr
                180                 185                 190

Leu Tyr Ile Asn Ile His Lys Ile Glu Asp Val Tyr Ile Asp Ile Ser
        195                 200                 205

Lys Lys Lys Ser Arg Asp Leu Tyr Ile Thr Cys Glu Phe Asn Gly Cys
210                 215                 220

His Leu Lys Ser Ser Gln Gly Asn Asn Cys Thr Lys Tyr Thr Phe Asn
225                 230                 235                 240

Glu Cys Phe Lys Ile Pro Ile Asn Thr Pro Ile Leu Glu Asp Thr Ile
                245                 250                 255

Ile Ile Lys Ile Trp Asp Trp Asn Phe Leu Ser Asn Asp Glu Leu Leu
                260                 265                 270

Ala Ile Gly Val Leu Ser Phe Asn Gln Ile Lys Asn Lys Ser Ile Asn
                275                 280                 285

Pro Thr Trp Leu Asn Leu Tyr Gly Phe His Lys Asp Glu Leu Asn Leu
            290                 295                 300

Glu Asn Tyr Tyr Asn Asn Gly Ser Asn Asp Ile Gly Leu Ile Arg Pro
305                 310                 315                 320

Asn Asp Phe Asn Leu Ala Leu Glu Gly Asn Val Tyr Leu Gly Arg Ile
                325                 330                 335

Cys Ile Ser Ala Tyr Val Glu Arg Leu Ser Asn Tyr Asp Ser Leu Ser
            340                 345                 350

Ile Pro Ile Ile Gln Ser Cys Leu Val Tyr Asp Pro Leu Tyr Val
            355                 360                 365

Ser Ile Thr Leu Leu Cys Asp Val Tyr Val Thr Gly Leu Leu Ala
        370                 375                 380

Glu Asn Ile Tyr Val Gln Leu Thr Cys Gly Pro His Lys Lys Lys Thr
385                 390                 395                 400

Asp Cys Val Ser Ala Asn Glu Ile Gly Trp Asp Asp Gln Asn Asn
                405                 410                 415
```

```
Ala Met Gly Val Asn Arg Lys Lys Met Arg Lys Asn Asn Ser Asp
            420                 425                 430

Glu Asn Ile Thr Asp Asn Gly Glu Phe Phe Asp Phe Leu Asn Phe Asn
            435                 440                 445

Gly Ile Leu Asn Ile Asp Asn Phe Phe Asn Thr Leu Thr Glu Lys Gln
            450                 455                 460

Gln Ile Leu Asp Asn Ser Gly Ser Thr Glu Phe Tyr Phe Ser Ser Arg
465                 470                 475                 480

Lys Gly Lys Ile Asp Asn Met Lys Leu Cys Ser Val Glu Asp Glu Leu
                485                 490                 495

Gln Gln Trp Asp Val Ile Ile Asn Val Tyr Glu Lys Glu Lys Lys Ile
            500                 505                 510

Asn Asn Asp Gly Ser Ile Phe Asn Asn Phe Met Tyr Ser Gly Gly Asn
            515                 520                 525

Asn Met Ile Ile Asp Lys Tyr Asn Tyr Tyr Asp Lys Gln Asn Lys Glu
            530                 535                 540

Ser Lys Leu Thr Asp Tyr Gln Lys Tyr Lys Ile Lys Lys Arg Glu Glu
545                 550                 555                 560

Asn Tyr Asp His Arg Lys Tyr Glu Asp Glu Asn Glu Ile Gly Val
                565                 570                 575

Lys Gln Asn Asn Asp Arg Arg Ile Ala Tyr Tyr Arg Met Pro Leu Lys
            580                 585                 590

Asn Val Leu Leu His Asn Glu Lys Ile Ser Arg Cys Pro Ile Trp Leu
            595                 600                 605

Pro Leu Lys Asn Ile Ser Lys Asn Val Asp Asn Gly Phe Asn Cys Met
            610                 615                 620

Tyr Asn Ile Phe Gln Asn Gly Ser Ile Leu Val Asn Leu Glu Lys Ser
625                 630                 635                 640

Tyr Asp Leu Gln Leu Gly Leu Asn Arg Arg Lys Lys Leu Val Pro Val
                645                 650                 655

Asn Tyr Glu Leu Arg Cys Tyr Ile Tyr Ala Cys Arg Asn Ile Ile Ser
                660                 665                 670

Asn Phe Asn Asp Ser Pro Asn Thr Phe Val His Ile Ser Cys Ser Gly
            675                 680                 685

Lys Met Lys Ile Thr Ser Leu Val Leu Asn Asn Ser Asn Pro Val Phe
            690                 695                 700

Leu Gln Cys Leu Lys Leu Asn Ile Thr Ile Leu Thr Asp Tyr Ser Val
705                 710                 715                 720

Gly Leu Pro Thr Ile Pro Phe Ile Val Val Thr Leu Tyr Glu Phe His
                725                 730                 735

Asn Asn Thr Phe Tyr Phe Ile Gly Arg Cys Phe Cys Asn Tyr Asp Ile
            740                 745                 750

Tyr Leu Lys Asp Asn His Lys Lys Cys Asn Phe Ala Asn Lys Ser Ser
            755                 760                 765

Lys Tyr Asn Met Val Glu Gln Ile Gln Pro Arg Trp Ile Lys Leu Lys
            770                 775                 780

Gly Asn Lys His Ala Lys Ala Met Tyr Pro Asn Ile Leu Trp Gln Gln
785                 790                 795                 800

Ser Gly Ser Tyr Lys Arg Ile Met Gln Glu Tyr Met Phe Glu Lys Gln
                805                 810                 815

Lys Asp Phe Tyr Thr Ser Asn Ala Asn Ile Gly Gly Asp Ile Thr Asn
            820                 825                 830

Gly Asn Asn Ser Thr Asn Arg Ile Asn Ser Gln Val Arg Gln Pro His
```

```
                835                 840                 845
Asn Asp Phe Leu His Gly Glu Arg Val Gly Asp Ile Leu Leu Tyr Phe
    850                 855                 860
Glu Leu Val Lys Glu Lys Asp Ala Met Lys Ile Pro Ile Tyr Pro Met
865                 870                 875                 880
Ile Thr Glu Ile Lys Lys Cys Thr Leu Ser Phe Phe Cys Met Ser Leu
                885                 890                 895
Glu Asn Leu Val Leu Met Lys Ile Pro Ser Lys Asn Glu His Ile
        900                 905                 910
Ile Pro Asn Gly Tyr Ile Lys Asn Asn Ile Thr Tyr Pro Ile Ile Val
            915                 920                 925
Leu Ser Ile Thr Ser Tyr Ser Ser Tyr Gly Lys Lys Asn Glu Leu
    930                 935                 940
Leu Ile Lys Tyr Ala Lys Ser Leu Lys Thr Asn Lys Arg Thr Gln Leu
945                 950                 955                 960
Lys Asn Trp Lys Asn Ala Phe Asn Gln Gln Ser Phe Glu Met Phe Ala
                965                 970                 975
Ile Glu Asn Phe Asp Ile Asp Val Pro Leu Asp Pro Ile Phe Asp Pro
            980                 985                 990
Thr Leu Asn Ile Lys Val Tyr Asn Lys Lys Val Lys Asp Lys Tyr Phe
                995                 1000                1005
Ile Gly Glu Thr Asn Ile Ser Leu Ile Pro Tyr Ile Pro Trp Ile
    1010                1015                1020
Glu Asn Leu Asp Asp Ala Leu Tyr Tyr Leu Gln Ala Tyr Glu Asp
    1025                1030                1035
Tyr Ser Glu Thr Ile Asn Ile Lys Asn Ile Asp Asn Ala Tyr Asn
    1040                1045                1050
Ile Tyr Lys Asn Lys Asn Ala Ala Leu Val Val Thr Ala Ile Ser
    1055                1060                1065
Leu Ala Asp Tyr Glu His Thr Ile Ser Leu Lys Glu Glu Leu Lys
    1070                1075                1080
Arg Tyr Glu Asn Asp Asp Gln Asp Asp Trp Asn Asn Ile
    1085                1090                1095
Pro Leu Phe Arg Gly Thr Phe Asn Ala Lys Phe Thr Gly Lys Ala
    1100                1105                1110
Ala Gly Met Ile Gly Gly Met Ala Gly Gly Met Ala Gly Gly Met
    1115                1120                1125
Ala Asp Gly Met Ala Gly Gly Met Ala Gly Gly Met Ala Gly Gly
    1130                1135                1140
Met Ala Gly Gly Met Ala Gly Gly Met Ala Gly Gly Met Ala Gly
    1145                1150                1155
Gly Met Ala Gly Gly Met Ala Gly Gly Met Ala Ala Asp Met Ala
    1160                1165                1170
Asn Gly Met His Leu Gly Leu His Ser Asn Phe Ile Gly Tyr Glu
    1175                1180                1185
Tyr Asp Pro Arg Asn Asp His Leu Ile Asn Asn Thr Thr Met Asn
    1190                1195                1200
Asn Phe Gln Met Asn Met Met Tyr Asn Arg Glu Asn Phe Ser Ser
    1205                1210                1215
Gly Asn Tyr Lys Ala Asn Cys Ile Ala Glu Phe Gly Glu Lys Gly
    1220                1225                1230
Ser Lys Ile Gly Asn Gly Phe Asn Asn Glu Gly Tyr Ile Thr Asn
    1235                1240                1245
```

```
Thr Arg His Tyr Phe Ser Cys Tyr Tyr Asn Lys Lys Asn Gln Arg
    1250            1255            1260

Asn Ile Tyr Asn Val Met Tyr Asn Glu Ser Val Tyr Lys Leu His
    1265            1270            1275

Asp Asp Gly Val Pro Glu Ile Ile Lys Ala Ser Tyr Asn Val Lys
    1280            1285            1290

Asn Tyr Pro Tyr Ile Lys Ile Leu Arg Asn Lys Phe Ile Leu Asn
    1295            1300            1305

Val Tyr Ile Pro Pro Arg Phe Ile Leu Tyr Val Glu Gly Asp Lys
    1310            1315            1320

Ile Asn Leu Glu Lys Phe Val Lys Asn Thr His Arg Val Ser Val
    1325            1330            1335

Asp Gly Ile Leu Glu Asn Tyr Leu Asp Asp Ile Leu Ile Pro Ser
    1340            1345            1350

Ile Pro Leu Lys Lys Lys Tyr Asn Asn Asn Ile Phe Leu Asn Cys
    1355            1360            1365

Gly Tyr Asn Gly Asn Ile Gly Asn Phe Asp Gly Asn Asp Gln Asn
    1370            1375            1380

Lys Ile Val Lys Glu Gly Ile Ser Phe Gly Cys Phe Glu Asn Ser
    1385            1390            1395

Pro Phe Val Glu Leu Val Gly Gly Gln Ile Lys Cys Phe Thr Lys
    1400            1405            1410

Ile Lys Tyr Arg Asp Ile Ile Ser Glu His Ile Pro Leu Lys Leu
    1415            1420            1425

Lys Asp Ile Asn Asn Gln Asn Thr Phe Arg Asn Lys Phe Arg Gly
    1430            1435            1440

Ser Asn Lys Ile Pro Leu Tyr Leu Lys Ile Arg Val Tyr Val Ile
    1445            1450            1455

Arg Gly Ile Gly Ile Asn Gly Val Asn Ser Glu Cys Ser Cys Asn
    1460            1465            1470

Pro Tyr Leu Thr Phe Ser Leu Gly Glu Lys Thr Thr Asn Leu Arg
    1475            1480            1485

Asn Ser Tyr Lys Glu Asp Asn Pro Asn Pro Asn Phe Ser Tyr Leu
    1490            1495            1500

Trp Glu Ser Glu Ala Ile Phe Pro Glu Asp Glu Ile Leu Thr Ile
    1505            1510            1515

Ser Val Tyr Ser Ala Glu Ser Asn Tyr Asp Lys Gln Ile Asn Asp
    1520            1525            1530

Ile Tyr Ile Gly Ser Thr Glu Ile Asn Leu Phe Asp Arg Trp Met
    1535            1540            1545

Ser Lys Glu Trp Arg His Met Met Lys Lys Asn Lys Val Pro Ile
    1550            1555            1560

Glu Tyr Arg Pro Leu Tyr Asn Asn Tyr Phe Lys Asn Gln Asn Leu
    1565            1570            1575

Ile Lys Asn Ser Ile Asn Gly Gly Gly Asn Met Tyr Asn Lys Leu
    1580            1585            1590

Asn Thr Trp Asn Asn Ile Phe Ser Phe Phe Asp Ile Phe Thr Asn
    1595            1600            1605

Leu Val Asn Phe Asn Ile Met Asn Gly His Ser Asn Asn Gln Tyr
    1610            1615            1620

Tyr Asn Gly Asn Ser Phe Ser Ser Cys Gly Ile Asn Asn Tyr Lys
    1625            1630            1635
```

Ser Ile Ser Asn Asn Gly Leu Leu Glu Met Trp Val Glu Ile Met
    1640                1645                1650

Gly Tyr Glu Glu Ala Ala Lys Ile Pro Ile His Lys Met Glu Pro
    1655                1660                1665

Pro Lys Thr Ser Glu Val Glu Ile Arg Ile Ile Ile Trp Arg Cys
    1670                1675                1680

Ser Ile Leu Leu Asn Gly Glu Asn Pro Asn Lys Thr Phe Asp Leu
    1685                1690                1695

Val Val Ala Ser Glu Leu Asp Cys Val Asn Tyr Asn Gly Lys Asn
    1700                1705                1710

Pro Ile Thr Gln Thr Thr Asp Val His Tyr Asn Cys Lys Thr Gly
    1715                1720                1725

Asp Ala Ile Phe Asn Trp Arg Met Val Tyr Pro Asn Ile Thr His
    1730                1735                1740

Pro Leu Asn Thr Cys Phe Leu Gln Leu Ala Ala Tyr Asn Asn Ser
    1745                1750                1755

Asn Val Gly Thr Ser Gln Phe Leu Gly Glu Val Asn Leu Glu Leu
    1760                1765                1770

Ser Lys Tyr Ile His Lys Val Leu Gln Ile Val Asn Lys Phe Glu
    1775                1780                1785

Leu Asp Ala Glu Leu Lys Leu Arg Lys Lys Asn Phe Gly Asp Asn
    1790                1795                1800

Thr Asn Gly Asp Asn Asn Cys Ser Gly Thr Ile Gln Val Thr Val
    1805                1810                1815

Gln Phe Ile Pro Gln Ser Lys Ala Asn Ile Lys Pro Ser Gly Leu
    1820                1825                1830

Gly Arg Ser Glu Pro Asn Arg Asn Pro Tyr Leu Arg Thr Pro Lys
    1835                1840                1845

Asn Gly Arg Asp Trp Asn Asp Phe Ala Tyr Ser Ile Gly Phe Asn
    1850                1855                1860

Asp Ile Tyr Lys Pro Phe Trp Ser Gly Leu Arg Val Phe Phe Ile
    1865                1870                1875

Phe Ser Leu Ala Val Trp Val Phe Phe Leu Ser Phe Ile Tyr Pro
    1880                1885                1890

Ala Met Leu Leu
    1895

<210> SEQ ID NO 27
<211> LENGTH: 1904
<212> TYPE: PRT
<213> ORGANISM: Plasmodium falciparum

<400> SEQUENCE: 27

Met Arg Ser Ile Ser Val Gly Phe Thr Ile Tyr Glu Ala Gln Asn Leu
1               5                   10                  15

Glu Val Asp Asp Lys Asn Leu Leu Asp Pro Leu Val Val Val Arg Cys
                20                  25                  30

Cys Asn Asn Glu Tyr Ile Thr Lys Lys Lys Lys Lys Tyr Asn Ala
        35                  40                  45

Val Asn Trp Glu Glu Ser His Ile Trp Asp Arg Ile Ile Leu Ser Glu
    50                  55                  60

Ile Glu Trp Asn Val Ser Lys Ile Glu Phe Glu Val Gln Ser Ala Asn
65                  70                  75                  80

Ile Leu Trp Arg Asn Asp Ile Ile Gly Val Ile Ser Phe Glu Leu Lys
                85                  90                  95

```
Leu Ile Lys Asn Lys Arg Asn His Gln Ile Gln Gly Ile Tyr Pro Ile
                100                 105                 110

Leu Cys Lys Asn Gly Thr Glu Ile Arg Gly Gln Leu Arg Leu Lys Val
            115                 120                 125

Met Val Cys Asp Glu Asn Asp Tyr Ile Ser Asn Asn Ile Phe Asn
    130                 135                 140

Asp Leu Thr Glu Asn Asn Asn Glu Asn Arg Ile Glu Asp Asn Glu Glu
145                 150                 155                 160

Ile Tyr Asn Asp Leu Thr Lys Ala Val Val Glu Glu Asn Leu Val Thr
                165                 170                 175

Leu Arg Asp Glu Lys Ser Arg Phe Tyr Tyr Leu Tyr Val Asn Ile His
            180                 185                 190

Lys Ile Glu Asp Ile Tyr Thr Asp Ile Ser Lys Lys Glu Tyr Arg Asp
            195                 200                 205

Leu Tyr Ile Thr Cys Asp Phe Asn Gly Cys His Leu Lys Ser Ser Gln
            210                 215                 220

Ala Arg Asn Cys Ile Asn Tyr Thr Phe Asn Glu Cys Phe Lys Ile Pro
225                 230                 235                 240

Ile Ala Thr Pro Ile Leu Asp Asp Ser Ile Ile Leu Lys Ile Trp Asp
                245                 250                 255

Trp Asn Tyr Leu Ser Asn Asp Glu Leu Ile Ala Ile Gly Val Leu Ser
            260                 265                 270

Phe Asn Gln Ile Lys Asn Glu Cys Leu Asn Pro Thr Trp Leu Asn Leu
            275                 280                 285

Tyr Gly Phe His Lys Lys Glu Phe Asp Leu Glu Lys Ile Thr Asn Asn
            290                 295                 300

Tyr Thr Asn Lys Asn Asn Ser Asn Asn Tyr Tyr Asp Ile Cys Asn Asp
305                 310                 315                 320

Tyr Asn Leu Leu Leu Glu Gly Asn Phe Tyr Leu Gly Arg Ile Cys Ile
                325                 330                 335

Ser Ser Tyr Val Glu Arg Ile Asn Asn Phe Asp Asn Leu Asn Ile Ala
            340                 345                 350

Ile Thr Gln Ser Cys Leu Ala Tyr Asp Asp Pro Leu Tyr Ile Pro Ile
            355                 360                 365

Thr Leu Leu Cys Asp Val Tyr Leu Val Thr Gly Ile Leu Ser Lys Asn
            370                 375                 380

Ile Tyr Val Glu Leu Thr Cys Gly Pro His Arg Lys Lys Thr Gln Cys
385                 390                 395                 400

Val Ser Val Asn Glu Met Leu Gln Asp Val Met Gly Lys Gln Thr Asn
                405                 410                 415

Gln Lys Lys Lys Thr Lys Lys Lys Ile Ile Lys Gly Ile His Asn
            420                 425                 430

Ser Tyr Ile Asp Asn Glu Ile Val Asn Asn Tyr Asp Asn Thr Ile
            435                 440                 445

Tyr Thr Tyr Asn Gln Lys Thr Asn Pro Leu Phe Thr Phe Asp Glu Ile
            450                 455                 460

Leu Asn Leu Asp Asn Val Phe Asn Lys Val Thr Glu Lys Gln Gln Ile
465                 470                 475                 480

Ile Glu Asn Asn Glu His Thr Glu Phe Tyr Phe Ser Ala Asn Lys Gly
                485                 490                 495

Lys Ile Glu Asn Met Lys Leu Cys Val Val Gln Glu Gly Tyr Gln Gln
            500                 505                 510
```

```
Trp Asp Ile Ile Ile Asn Val Tyr Glu Lys Val Tyr Asn Asn Ser Tyr
            515                 520                 525
His Glu Asn Asn Phe Leu Pro Ser Leu Leu Tyr Asn Asn Glu Glu Thr
        530                 535                 540
Lys Asn Asp Asp Tyr Ser Lys Leu Thr Glu Tyr Gln Lys Tyr Gln Lys
545                 550                 555                 560
Lys Lys Glu Glu Ile Asp Gln Tyr Glu Gln Asn Ile Pro Asn His Ile
                565                 570                 575
Asp Arg Arg Ile Ala Tyr Tyr Arg Met Pro Leu Lys Asn Val Leu Leu
            580                 585                 590
Tyr Asn Glu Lys Ile Ser Arg Cys Pro Ile Trp Ile Pro Leu Lys Asn
        595                 600                 605
Ile Pro Lys Asn Val Gln Gly Asp Phe Asn Cys Met Tyr Asn Ile Phe
    610                 615                 620
Gln Asn Gly Ser Ile Leu Leu Asn Leu Glu Lys Ser Phe Asp Val Gln
625                 630                 635                 640
Leu Gly Ile Asn Arg Arg Lys Lys Leu Ile Pro Val Asn Tyr Glu Leu
                645                 650                 655
Arg Cys Tyr Ile Tyr Ala Cys Arg Asn Val Ile Ser His Phe Asn Asp
            660                 665                 670
Ser Pro Asn Thr Phe Val His Ile Ser Cys Ala Gly Lys Met Lys Ile
        675                 680                 685
Thr Ser Leu Ser Leu Asn Ser Cys Asn Pro Val Tyr Leu Gln Cys Leu
    690                 695                 700
Lys Leu Asn Ile Asn Ile Leu Thr Asp Tyr Ser Ile Gly Leu Pro Thr
705                 710                 715                 720
Ile Pro Leu Ile Ile Val Thr Leu Tyr Glu Phe His Asn Asp Thr Phe
                725                 730                 735
Tyr Tyr Ile Gly Arg Cys Tyr Cys Asn Tyr Asp Ile Tyr Leu Lys Gln
            740                 745                 750
Ser Gly Asn Lys Tyr Asn Phe Thr Glu Lys Gly Ser Lys Tyr Asn Val
        755                 760                 765
Val Glu Gln Ile Lys Pro Lys Trp Ile Lys Leu Lys Gly Ser Lys Tyr
    770                 775                 780
Thr Lys Ala Met Tyr Ala Asn Asn Leu Trp Gln His Asn Gly Asn Asp
785                 790                 795                 800
Lys Arg Ile Met Gln Glu Tyr Leu Tyr Glu Lys Gln Gln Glu Leu Ile
                805                 810                 815
Asn Asn Ser Thr Ile Asn Lys Asn Asn Asn Asn Asn Lys Lys Asp
            820                 825                 830
Asn Asn Asn Lys Lys Asp Asn Asn Lys Lys Asp Asn Asn Asn Asn
        835                 840                 845
Asn Asn Asn Asn Tyr Tyr Tyr Asn Ser Ser Asn Val Tyr Gln Tyr Asn
    850                 855                 860
Asp Leu Leu Tyr Gly Glu Arg Val Gly Asp Ile Leu Leu Tyr Phe Glu
865                 870                 875                 880
Leu Val Gln Ser Lys Asp Ala Met Lys Phe Pro Ile Tyr Pro Met Ile
                885                 890                 895
Thr Glu Ile Lys Lys Cys Thr Leu Ser Phe Phe Cys Met Ser Leu Glu
            900                 905                 910
Asn Leu Ile Leu Met Lys Lys Ala Asn Phe Leu Lys Thr Leu Ser Phe
        915                 920                 925
Glu Arg Asn Asn Lys Tyr Gln Ile Ser Thr Pro Ile Ile Leu Leu Ser
```

-continued

```
            930             935             940
Ile Thr Ser Tyr Ser Ser Tyr Gly Lys Lys Asn Glu Leu Met Ile
945             950             955             960
Lys Tyr Glu Lys Thr Leu Lys Ala Asn Thr Arg Ile Gln Leu Lys Asn
            965             970             975
Trp Lys Asn Ser Phe Asn Gln Gln Ser Phe Glu Met Phe Ser Ile Glu
            980             985             990
Asn Met Asn Ile Asp Ile Pro Leu Asp Pro Ile Phe Asp Pro Ile Leu
            995             1000            1005
Asn Ile Lys Val Tyr Asn Lys Val Lys Ser Lys Tyr Phe Ile
    1010            1015            1020
Gly Glu Thr Asn Ile Ser Leu Val Pro Tyr Leu Pro Trp Ile Lys
    1025            1030            1035
Asn Ile Asp Glu Val Leu Tyr Tyr Leu Gln Ala His Asp Asp Tyr
    1040            1045            1050
Ser Glu Thr Ile Asn Met Lys Asn Ile Asp Asn Thr Phe Asn Ile
    1055            1060            1065
Tyr Lys Asn Lys Asn Ala Ala Leu Val Ile Ser Ala Ile Ser Leu
    1070            1075            1080
Ala Asp Cys Glu Asp Thr Leu Ser Leu Lys Glu Glu Ile Asn Lys
    1085            1090            1095
Tyr Glu Asn Asp Asp Glu Ala Trp Lys Glu Ile Pro Leu Phe
    1100            1105            1110
Asn Leu Asp Gln Glu Asn Gln Lys Glu Asp Asn Lys Asn Thr Ser
    1115            1120            1125
Ser Gln His Gly Asn Val Thr Asn Asn Tyr Asp Gly Tyr Asn Asn
    1130            1135            1140
Gly Ala Tyr Glu Met Gly Met Tyr Asn Met Glu Thr Tyr Asn Ile
    1145            1150            1155
Lys Asn Asn Asp Asn Asn Asn Asn Tyr Asn Asn Tyr Asn
    1160            1165            1170
Asn Asn Ser Tyr Asn Asn Asn Tyr Tyr Asn Asn Tyr Ala
    1175            1180            1185
Ala Pro Tyr Thr Ser Tyr Asn Asn Asn Val Leu Gln Asn Asp Thr
    1190            1195            1200
Arg Asn Asn Val Arg Tyr Asn His Ser Asn Asn Met Met Ile Asn
    1205            1210            1215
Asn Met Tyr Lys Asn Asn Ile Tyr Asn Ala Ser Gln Phe Gly Val
    1220            1225            1230
Ile Asn Tyr Asn Asn Tyr Asn Tyr Tyr Asp Lys Gly Asn Thr
    1235            1240            1245
Leu Asn Phe Asn Asn Asn Asn Ile His His Phe Asn Lys Leu Ser
    1250            1255            1260
Asn Asn Lys Phe Asp Ser Tyr Leu Ser Arg Ile Gln Lys Asp Thr
    1265            1270            1275
Tyr Asn Ile Lys Tyr Asn Asn Ser Ile Tyr Lys Leu Phe Asp Asp
    1280            1285            1290
Gly Ile Pro Glu Ile Ile Lys Leu Ser Tyr Asn Val Lys Asn Tyr
    1295            1300            1305
Pro Tyr Ile Lys Ile Leu Thr Ser Lys Tyr Ile Leu Asn Val His
    1310            1315            1320
Ile Pro Pro Arg Phe Ile Leu Tyr Val Glu Gly Asp Lys Leu Asn
    1325            1330            1335
```

Ile Glu Lys Phe Ile Lys Asn Ile Asn Arg Val Ser Val Asp Gly
1340                1345                1350

Ile Leu Glu Asn Tyr Leu Asp Asp Ile Leu Ile Pro Ser Leu Pro
1355                1360                1365

Leu Ile Lys Lys Cys Asn Asp Ile Ser Cys Asp Asn Asn Tyr Asn
1370                1375                1380

Glu Asn Lys Ile Glu Lys Gln Gly Ile Lys Phe Gly Cys Phe Glu
1385                1390                1395

Gln Phe Pro Phe Val Glu Ile Ile Gly Gly Gln Ile Lys Cys Phe
1400                1405                1410

Thr Lys Ile Lys Tyr Arg Asn Leu Glu Ser Glu Asn Met Pro Leu
1415                1420                1425

Ser Leu Lys Asp Ile Thr Asn Gln Asn Ile Phe Arg Asn Lys Phe
1430                1435                1440

Arg Gly Lys Asn Lys Ile Pro Leu Tyr Leu Lys Ile Arg Val Tyr
1445                1450                1455

Val Leu Arg Gly Ile Gly Leu Tyr Gly Ile Asn Asn Glu Tyr Thr
1460                1465                1470

Ala Asn Pro Tyr Leu Ile Phe Ser Leu Gly Glu Lys Thr Ser Asn
1475                1480                1485

Leu Arg Asn Ala Phe Lys Arg Ser Asn Ile Asn Pro Glu Phe Gly
1490                1495                1500

Cys Leu Trp Glu Ser Glu Ala Ile Phe Pro Glu Asp Glu Ile Leu
1505                1510                1515

Thr Ile Ser Val Tyr Ser Ala Glu Asp Asn Tyr Asp Lys Gln Ile
1520                1525                1530

Asn Asp Ile Tyr Ile Gly Ser Thr Glu Ile Asn Leu Phe Asp Arg
1535                1540                1545

Trp Met Ser Lys Glu Trp Arg His Met Met Lys Lys Asn Lys Ile
1550                1555                1560

Pro Val Glu Tyr Arg Pro Leu Tyr Ser Asn Tyr Ile Lys His Pro
1565                1570                1575

Lys Met Val Ser Ser Asn Asn Tyr Asn Thr Met Asn Ser Trp Asn
1580                1585                1590

Asn Ile Phe Ser Phe Phe Asp Ile Phe Asn Tyr Leu Met Thr Tyr
1595                1600                1605

Thr Ser Pro Thr Lys Gly Asn Asn Asn Asn Asn Asp Asn Asn
1610                1615                1620

Asn Asn Asn Ser Asn Ile Tyr Gly Asn His Ser Leu Lys Asp Thr
1625                1630                1635

His Ser Asn Ile Ser Phe Gly Asn Ser Gln Lys Arg Asn Asn Gly
1640                1645                1650

Ile Leu Glu Met Trp Val Glu Ile Met Asp Tyr Glu Gln Ser Lys
1655                1660                1665

Lys Ile Pro Ile His Lys Met Val Pro Pro Lys Lys Thr Glu Ile
1670                1675                1680

Glu Ile Arg Ile Ile Ile Trp Arg Cys Thr Met Leu Thr Asn Lys
1685                1690                1695

Asp Asn Ile Asn Lys Thr Met Asp Leu Thr Val Thr Ser Glu Leu
1700                1705                1710

Asp Cys Ile Thr Tyr Asn Gly Lys Asn Pro Thr Met Gln Ser Thr
1715                1720                1725

-continued

```
Asp Val His Tyr Asn Cys Lys Thr Gly Thr Ala Ile Phe Asn Trp
    1730                1735                1740

Arg Ile Val Tyr Pro Asn Ile Thr His Pro Leu Asn Thr Cys Phe
    1745                1750                1755

Leu Gln Leu Ala Ala Tyr Asn Asn Asn Val Gly Val Ser Glu
    1760                1765                1770

Phe Leu Gly Glu Val Asn Leu Glu Leu Ser Lys Tyr Ile Gln Lys
    1775                1780                1785

Ala Ser Gln Ile Leu Asn Lys Phe Glu Leu Asp Ala Glu Leu Lys
    1790                1795                1800

Leu Arg Lys Lys Thr Asp Thr Asp His Asn Lys Asn Thr Tyr Asn
    1805                1810                1815

Gly Tyr Ile Gln Val Thr Val Gln Phe Ile Pro Gln Asn Lys Ala
    1820                1825                1830

Asn Ile Lys Pro Val Gly Leu Gly Arg Asp Glu Pro Asn Arg Asn
    1835                1840                1845

Pro Tyr Leu Lys Thr Pro Asp Ser Gly Arg Glu Trp Asn Asp Phe
    1850                1855                1860

Met Tyr Ser Ile Gly Phe Asn Asp Ile Tyr Lys Pro Phe Trp Asn
    1865                1870                1875

Ser Leu Lys Leu Ala Phe Ile Cys Leu Leu Val Ile Trp Val Phe
    1880                1885                1890

Val Leu Ser Phe Val Tyr Pro Ser Leu Leu Arg
    1895                1900

<210> SEQ ID NO 28
<211> LENGTH: 1943
<212> TYPE: PRT
<213> ORGANISM: Plasmodium yoelii
<220> FEATURE:
<221> NAME/KEY: misc_feature
<222> LOCATION: (39)..(39)
<223> OTHER INFORMATION: Xaa can be any naturally occurring amino acid

<400> SEQUENCE: 28

Met Arg Val Ile Ser Val Gly Phe Ile Ile Tyr Glu Ala Gln Asn Leu
1               5                   10                  15

Lys Val Glu Asp Lys Glu Leu Leu Asp Pro Leu Val Val Arg Cys
                20                  25                  30

Cys Asn Asn Glu Tyr Ile Xaa Lys Lys Lys Lys Lys Tyr Asn Ala
            35                  40                  45

Val Asn Trp Glu Glu Thr His Val Trp Asn Arg Ile Val Leu Ser Glu
    50                  55                  60

Ile Glu Trp Asn Val Ala Lys Ile Glu Phe Glu Val Gln Ser Ala Asn
65                  70                  75                  80

Thr Phe Trp Arg Asn Asp Val Ile Gly Val Ile Ser Phe Glu Leu Lys
                85                  90                  95

Leu Ile Arg Asn Lys Lys Asn His Gln Ile Tyr Gly Tyr Pro Ile
            100                 105                 110

Leu Tyr Lys Asn Arg Thr Glu Ile Gln Gly Gln Leu Arg Leu Lys Val
        115                 120                 125

Ile Val Cys Asn Glu Asn Asp Tyr Thr Ser Ser Glu Ile Tyr Ser
    130                 135                 140

Ser Leu Thr Gln Tyr Asn Asn Asn Thr Asn Asp Asn Asn Gly Asn Asn
145                 150                 155                 160

Thr Ser Asp Asn Glu Asn Phe Tyr Glu Asp Leu Thr Lys Ala Val Val
```

```
                165                 170                 175
Glu Glu Asn Thr Ile Ala Leu Arg Asp Ala Asn Ser Arg Phe Tyr Tyr
            180                 185                 190
Leu Tyr Ile Asn Ile His Lys Ile Glu Asp Val Tyr Ile Asp Ile Ser
            195                 200                 205
Lys Lys Lys Ser Arg Asp Leu Tyr Ile Thr Cys Glu Phe Asn Gly Cys
            210                 215                 220
His Leu Lys Ser Ser Gln Gly Asn Asn Cys Thr Lys Tyr Thr Phe Asn
225                 230                 235                 240
Glu Cys Phe Lys Ile Pro Ile Asn Thr Pro Ile Leu Glu Asp Thr Ile
            245                 250                 255
Ile Ile Lys Ile Trp Asp Trp Asn Phe Leu Ser Thr Asp Glu Leu Leu
            260                 265                 270
Ala Ile Gly Val Leu Ser Phe Asn Gln Ile Lys Asn Lys Ser Ile Asn
            275                 280                 285
Pro Thr Trp Leu Asn Leu Tyr Gly Phe His Lys Asp Glu Leu Asn Leu
            290                 295                 300
Glu Asn Tyr Tyr Asn Asn Gly Ser Asn Asp Thr Ser Leu Ile Arg Pro
305                 310                 315                 320
Ser Asp Phe Asn Leu Ala Leu Glu Gly Asn Val Tyr Leu Gly Arg Ile
            325                 330                 335
Cys Ile Ser Ala Tyr Val Glu Arg Leu Ser Asn Tyr Asp Ser Leu Ser
            340                 345                 350
Ile Pro Ile Ile Gln Ser Cys Leu Val Tyr Asp Asp Pro Leu Tyr Val
            355                 360                 365
Pro Ile Thr Leu Leu Cys Asp Val Tyr Val Thr Gly Leu Leu Ala
            370                 375                 380
Glu Asn Ile Tyr Val Gln Leu Thr Cys Gly Pro His Lys Lys Lys Thr
385                 390                 395                 400
Asp Cys Val Ser Ala Asn Glu Ile Gly Trp Asp Asp Gln Asn Asn
            405                 410                 415
Ala Ile Gly Val Asn Arg Lys Lys Lys Met Arg Lys Lys Asn Ser Asp
            420                 425                 430
Glu Asn Ile Thr Asp Asn Val Glu Phe Phe Asp Phe Leu Asn Phe Asn
            435                 440                 445
Gly Ile Leu Asn Thr Asp Asn Phe Phe Asn Thr Leu Thr Glu Lys Gln
            450                 455                 460
Gln Ile Leu Glu Asn Ser Gly Ser Thr Glu Phe Tyr Phe Ser Ser Arg
465                 470                 475                 480
Lys Gly Lys Ile Asp Asn Met Lys Leu Cys Ser Val Glu Asp Glu Leu
            485                 490                 495
Gln Gln Trp Asp Ile Ile Asn Val Tyr Glu Lys Glu Lys Lys Thr
            500                 505                 510
Asn Asn Asp Gly Asn Ile Phe Asn Asn Phe Ile Tyr Ser Gly Gly Asn
            515                 520                 525
Asn Met Ile Thr Asp Lys Tyr Asn Tyr Tyr Lys Gln Asn Lys Glu
            530                 535                 540
Ser Lys Leu Thr Asp Tyr Gln Lys Tyr Lys Leu Lys Lys Arg Glu Glu
545                 550                 555                 560
Asn Tyr Asp His Arg Lys Tyr Glu Glu Asp Glu Glu Asn Glu Ile Gly
            565                 570                 575
Val Lys Gln Asn Asn Asp Arg Arg Ile Ala Tyr Tyr Arg Met Pro Leu
            580                 585                 590
```

```
Lys Asn Val Leu Leu His Asn Glu Lys Ile Ser Arg Cys Pro Ile Trp
        595                 600                 605

Leu Pro Leu Lys Asn Ile Ser Lys Asn Val Asp Ser Gly Phe Asn Cys
        610                 615                 620

Met Tyr Asn Ile Phe Gln Asn Gly Ser Ile Leu Val Asn Leu Glu Lys
625                 630                 635                 640

Ser Tyr Asp Leu Gln Leu Gly Leu Asn Arg Arg Lys Lys Leu Val Pro
                645                 650                 655

Val Asn Tyr Glu Leu Arg Cys Tyr Ile Tyr Ala Cys Arg Asn Ile Ile
                660                 665                 670

Ser Asn Phe Asn Asp Ser Pro Asn Thr Phe Val His Ile Ser Cys Ser
        675                 680                 685

Gly Lys Met Lys Ile Thr Ser Leu Val Leu Asn Asn Ser Asn Pro Val
        690                 695                 700

Phe Leu Gln Cys Leu Lys Leu Asn Ile Thr Ile Leu Thr Asp Tyr Ser
705                 710                 715                 720

Val Gly Leu Pro Thr Ile Pro Phe Ile Val Val Thr Leu Tyr Glu Phe
                725                 730                 735

His Asn Asn Thr Phe Tyr Phe Ile Gly Arg Cys Phe Cys Asn Tyr Asp
                740                 745                 750

Ile Tyr Leu Lys Asp Asn His Lys Lys Cys Asn Phe Ala Asn Lys Ser
        755                 760                 765

Ser Lys Tyr Asn Met Val Glu Gln Ile Gln Pro Arg Trp Ile Lys Leu
        770                 775                 780

Lys Gly Asn Lys His Ala Lys Ala Met Tyr Pro Asn Met Leu Trp Gln
785                 790                 795                 800

Gln Ser Gly Ser Tyr Lys Arg Met Met Gln Glu Tyr Met Phe Glu Lys
                805                 810                 815

Gln Lys Asp Phe Tyr Thr Ser Asn Ala Asn Ile Gly Gly Asp Met Ala
                820                 825                 830

Asn Asp Asn Ser Ser Thr Asn Arg Ile Asn Ser Gln Arg Arg Gln Pro
        835                 840                 845

His Asn Asp Phe Leu His Gly Glu Arg Val Gly Asp Ile Leu Leu Tyr
        850                 855                 860

Phe Glu Leu Val Lys Glu Lys Asp Ala Met Lys Ile Pro Ile Tyr Pro
865                 870                 875                 880

Met Ile Thr Glu Ile Lys Lys Cys Thr Leu Ser Phe Phe Cys Met Ser
                885                 890                 895

Leu Glu Asn Leu Val Leu Met Lys Ile Pro Ser Lys Lys Asn Glu His
                900                 905                 910

Ile Ile Pro Asn Asp Tyr Arg Lys Asn Ile Thr His Pro Ile Ile
        915                 920                 925

Val Leu Ser Ile Thr Ser Tyr Ser Ser Tyr Gly Lys Lys Lys Asn Glu
        930                 935                 940

Leu Leu Ile Lys Tyr Ala Lys Ser Leu Lys Ser Asn Thr Arg Thr Gln
945                 950                 955                 960

Leu Lys Asn Trp Lys Asn Ala Phe Asn Gln Gln Ser Phe Glu Met Phe
                965                 970                 975

Ala Ile Glu Asn Phe Asp Ile Asp Val Pro Leu Asp Pro Ile Phe Asp
                980                 985                 990

Pro Thr Leu Asn Ile Lys Val Tyr  Asn Lys Lys Val Lys  Asp Lys Tyr
        995                 1000                 1005
```

```
Phe Ile Gly Glu Thr Asn Ile Ser Leu Ile Pro Tyr Ile Pro Trp
1010                1015                1020

Ile Glu Asn Leu Asp Asp Ala Leu Tyr Tyr Leu Gln Ala Tyr Glu
    1025                1030                1035

Asp Tyr Ser Glu Thr Ile Asn Ile Lys Asn Ile Asp Asn Ala Phe
    1040                1045                1050

Asn Ile Tyr Lys Asn Lys Asn Ala Ala Leu Val Val Thr Ala Ile
    1055                1060                1065

Ser Leu Ala Asp Tyr Glu His Thr Ile Ser Leu Lys Glu Glu Leu
    1070                1075                1080

Lys Lys Tyr Glu Asn Asp Asp Gln Asp Asp Trp Asn Asn Ile
    1085                1090                1095

Pro Leu Phe Arg Val Asn Ser Asn Ala Lys Phe Thr Gly Lys Val
    1100                1105                1110

Ser Gly Met Ile Gly Asp Ile Ala Gly Gly Met Ser Gly Gly Met
    1115                1120                1125

Ile Ala Asp Met Pro Asn Gly Met Ile Gly Asp Ile Pro Asn Gly
    1130                1135                1140

Met Gly Gly Gly Ile Pro Asn Gly Met Gly Gly Met Pro Asn
    1145                1150                1155

Gly Met Gly Gly Gly Met Pro Asn Gly Met Val Gly Gly Met Pro
    1160                1165                1170

Asn Gly Met Ile Gly Asp Ile Pro Asn Gly Met Gly Gly Gly Met
    1175                1180                1185

Pro Asn Gly Met Gly Gly Gly Met Pro Asn Gly Met Gly Gly Gly
    1190                1195                1200

Met Pro Asn Gly Met Gly Gly Asp Ile Pro Asn Gly Ile Gly Gly
    1205                1210                1215

Gly Ile Pro Asn Gly Met Gly Gly Gly Pro His Pro Asn Phe Val
    1220                1225                1230

Gly His Glu Tyr Asp Pro Arg Asn Asp His Leu Ile Asn Asn Thr
    1235                1240                1245

Met Met Asn Asn Phe Gln Met Asn Met Met His Asn Arg Glu Asn
    1250                1255                1260

Tyr Pro Ser Gly Asn Tyr Lys Val Asn Cys Ile Ala Glu Phe Gly
    1265                1270                1275

Lys Lys Gly Ser Lys Ile Gly Asn Gly Phe Asn Asn Glu Gly Tyr
    1280                1285                1290

Thr Thr Asn Met Asn His Tyr Phe Ser Cys Tyr Tyr Asn Lys Lys
    1295                1300                1305

Asn Gln Arg Asn Ile Tyr Asn Val Met Tyr Asn Glu Ser Val Tyr
    1310                1315                1320

Lys Leu His Asp Asp Gly Val Pro Glu Ile Ile Lys Ala Ser Tyr
    1325                1330                1335

Asn Val Lys Asn Tyr Pro Tyr Ile Lys Ile Leu Arg Asn Lys Phe
    1340                1345                1350

Ile Leu Asn Val Tyr Ile Pro Pro Arg Phe Ile Leu Tyr Val Glu
    1355                1360                1365

Gly Asp Lys Ile Asn Leu Glu Lys Phe Val Lys Asn Thr His Arg
    1370                1375                1380

Val Ser Val Asp Gly Ile Leu Glu Asn Tyr Leu Asp Asp Ile Leu
    1385                1390                1395

Ile Pro Ser Ile Pro Leu Lys Lys Lys Tyr Asn Asn Lys Ile Phe
```

```
                1400                1405                1410

Leu Asn Cys Gly Tyr Asn Gly Asp Ile Gly Asn Phe Asp Glu Asn
    1415                1420                1425

Asp Gln Asn Lys Ile Val Lys Glu Gly Ile Ser Phe Gly Cys Phe
    1430                1435                1440

Glu Asn Ser Pro Phe Val Glu Leu Val Gly Gly Gln Ile Lys Cys
    1445                1450                1455

Phe Thr Lys Ile Lys Tyr Arg Asp Ile Ile Ser Glu His Ile Pro
    1460                1465                1470

Leu Lys Leu Lys Asp Ile Asn Asn Gln Asn Thr Phe Arg Asn Lys
    1475                1480                1485

Phe Arg Gly Ala Asn Lys Ile Pro Leu Tyr Leu Lys Ile Arg Val
    1490                1495                1500

Tyr Val Ile Arg Gly Ile Gly Ile Asn Gly Val Asn Ser Glu Cys
    1505                1510                1515

Ser Cys Asn Pro Tyr Leu Thr Phe Ser Leu Gly Glu Lys Thr Thr
    1520                1525                1530

Asn Leu Arg Asn Ser Tyr Lys Glu Asp Asn Pro Asn Pro Asn Phe
    1535                1540                1545

Ser Tyr Leu Trp Glu Ser Glu Ala Ile Phe Pro Glu Asp Glu Ile
    1550                1555                1560

Leu Thr Ile Ser Val Tyr Ser Ala Glu Ser Asn Tyr Asp Lys Gln
    1565                1570                1575

Ile Asn Asp Ile Tyr Ile Gly Ser Thr Glu Ile Asn Leu Phe Asp
    1580                1585                1590

Arg Trp Met Ser Lys Glu Trp Arg His Met Met Lys Lys Asn Lys
    1595                1600                1605

Val Pro Ile Glu Tyr Arg Pro Leu Tyr Asn Asn Tyr Phe Lys Asn
    1610                1615                1620

Gln Asn Leu Ile Lys Asn Ser Ile Asn Gly Gly Ser Asn Met Tyr
    1625                1630                1635

Asn Lys Leu Asn Thr Trp Asn Asn Ile Phe Ser Phe Phe Asp Ile
    1640                1645                1650

Phe Thr Asn Leu Val Asn Phe Asn Ile Met Asn Gly Tyr Ser Asn
    1655                1660                1665

Asn Gln Tyr Tyr Asn Gly Asn Asn Phe Ser Ser Tyr Gly Ile Asn
    1670                1675                1680

Asn Ser Lys Ser Ile Ser Asn Asn Gly Leu Leu Glu Met Trp Val
    1685                1690                1695

Glu Ile Met Ser Tyr Glu Glu Ala Ala Lys Ile Pro Ile His Lys
    1700                1705                1710

Met Glu Pro Pro Lys Ile Ser Glu Val Glu Ile Arg Ile Ile Ile
    1715                1720                1725

Trp Arg Cys Asn Ile Leu Leu Asn Gly Glu Asn Thr Asn Lys Thr
    1730                1735                1740

Phe Asp Leu Val Val Thr Ser Glu Leu Asp Cys Val Asn Tyr Asn
    1745                1750                1755

Gly Lys Asn Pro Ile Thr Gln Thr Thr Asp Val His Tyr Asn Cys
    1760                1765                1770

Lys Thr Gly Asp Ala Ile Phe Asn Trp Arg Met Val Tyr Pro Asn
    1775                1780                1785

Ile Thr His Pro Leu Asn Thr Cys Phe Leu Gln Leu Ala Val Tyr
    1790                1795                1800
```

```
Asn Asn Ser Asn Val Gly Thr Ser Gln Phe Leu Gly Glu Val Asn
    1805                1810                1815

Leu Glu Leu Ser Lys Tyr Ile His Lys Val Leu Gln Val Val Asn
    1820                1825                1830

Lys Phe Glu Leu Asp Ala Glu Leu Lys Leu Arg Lys Lys Asn Phe
    1835                1840                1845

Gly Asp Asn Thr Asn Gly Asp Asn Asn Cys Ser Gly Thr Ile Gln
    1850                1855                1860

Val Thr Val Gln Phe Ile Pro Gln Ser Lys Ala Asn Ile Lys Pro
    1865                1870                1875

Ser Gly Leu Gly Arg Ser Glu Pro Asn Arg Asn Pro Tyr Leu Arg
    1880                1885                1890

Thr Pro Lys Asn Gly Arg Asp Trp Asn Asp Phe Ala Tyr Ser Ile
    1895                1900                1905

Gly Phe Asn Asp Ile Tyr Lys Pro Phe Trp Gly Gly Leu Arg Cys
    1910                1915                1920

Ile Leu Ser Tyr Lys Leu Thr Phe Phe Lys Phe Gln Phe Phe Ala
    1925                1930                1935

Pro His Pro Leu Lys
    1940

<210> SEQ ID NO 29
<211> LENGTH: 1445
<212> TYPE: PRT
<213> ORGANISM: Toxoplasma gondii

<400> SEQUENCE: 29

Met Gly Lys Thr Lys Ile Tyr Ser Val Gly Phe Thr Val His Glu Ala
1               5                   10                  15

Gln Thr Leu Val Thr Glu Lys Gly Gln Pro Val Asp Pro Leu Val Val
                20                  25                  30

Val Arg Cys Cys Gly Arg Glu Tyr Arg Thr Glu Ile Lys Tyr Ala Lys
            35                  40                  45

Ser Asn Val Val Ser Trp Asp Glu Ser His Thr Trp Thr Asp Leu Cys
        50                  55                  60

Leu Thr Asp Glu Glu Trp Glu Thr Ala Tyr Ile Thr Phe Glu Val Gln
65                  70                  75                  80

Ala Ala Asn Ala Phe Trp Arg Asn Thr Leu Leu Gly Leu Val Ser Val
                85                  90                  95

Gln Leu Arg Leu Ile Gln Leu Arg Lys Thr His Gln Ile Arg Lys Ala
                100                 105                 110

Leu Pro Leu Gln His Pro Asp Asp Thr Asp Val His Gly Ser Leu Arg
            115                 120                 125

Val Thr Val Phe Ala Cys Ala Pro Gly Glu Ala Pro Pro Ser Pro Gly
        130                 135                 140

Glu Glu Glu Val Leu Glu Glu Asp His Asn Asp Tyr Asp Asp Leu
145                 150                 155                 160

Arg Lys Ala Val Ile Asp Thr Asn Gln Val Val Glu Arg Glu Ala Gly
                165                 170                 175

Ser Arg Leu Tyr His Val Tyr Val Thr Ala Tyr Arg Val Glu Asp Leu
                180                 185                 190

Pro Arg Ser Ser Lys Gly Ala Arg Asp Pro Phe Val Thr Cys Glu Phe
            195                 200                 205

Ala Gly Cys Lys Leu Lys Ser Thr Gln Ala Arg Gly Cys Cys Ser His
```

-continued

```
                210                 215                 220
Thr Phe Asn Glu Cys Phe Arg Phe Pro Val Val Thr Pro Leu Pro Glu
225                 230                 235                 240

Asp Ala Ile Leu Ile Lys Ile Trp Asp Trp Asn Phe Met Lys Ala Asp
                245                 250                 255

Glu Leu Ile Ala Val Val Gln Phe Cys Arg Gly Ser Ser Val Ile Arg
                260                 265                 270

Thr Arg Gln Thr Leu Lys Ser Arg Trp Gly Tyr Gln Met Asp Ser Cys
                275                 280                 285

Cys Thr Asn Glu Ala Glu Tyr Trp Trp Phe Asn Leu Tyr Gly Phe Asp
        290                 295                 300

Asp Glu Glu Val Ala Gln Ala Thr Lys Val Ala Gly Gln Gly Gly Arg
305                 310                 315                 320

Leu Val Ala Asn Cys Tyr Leu Gly Arg Ile Leu Leu Gly Ala Arg Ala
                325                 330                 335

Glu Arg Leu Thr Lys Glu Asp Asp Leu Met Pro Ala His Thr Val Ala
                340                 345                 350

Ala Arg Pro Tyr Glu Thr Pro Pro Val Ile Pro Leu Ala Val Leu Ala
                355                 360                 365

Asp Val Tyr Glu Val Gln Gly Ala Pro Gly Glu Lys Val Ser Val Glu
                370                 375                 380

Ile Trp Cys Gly Pro Ala Arg Ala Arg Thr Lys Trp Val Thr Gly Leu
385                 390                 395                 400

Glu Thr Lys Ala Ala Gln Arg Ala Gly Val Ala Pro Gln Ala Phe Asn
                405                 410                 415

Arg Ala Met Glu Gly Ala Leu Gly Val Ala Ser Tyr Leu Arg Gly Asp
                420                 425                 430

Ile Pro Glu Gly Glu Asp Arg Phe Pro Phe Asp Asn Thr Glu Gly Arg
                435                 440                 445

Val Glu Asp Leu Arg Leu Val Val Pro Glu Asp Thr Lys Gln Gln Trp
                450                 455                 460

Asp Ile Ile Ile Ser Leu Tyr Val Arg Gly Thr Thr Lys Gly Phe Met
465                 470                 475                 480

Gly Asp Thr Arg Ile Ala Phe Gln Arg Leu Lys Met Ser Lys Ile Pro
                485                 490                 495

Gly His Val His Asn Asn Pro Arg Ala Pro Ile Trp Val Pro Leu Ile
                500                 505                 510

Ser Thr Pro Pro Phe Glu Ser Val Lys Pro Ala Pro Ala Ile Leu Met
                515                 520                 525

Val Ile Glu Lys Ser Lys Val Glu Ala Phe Ala Arg Ser Lys Arg Lys
                530                 535                 540

His Val Thr Ala Val Gly Tyr Gln Leu Arg Ala Tyr Val Tyr Ala Ala
545                 550                 555                 560

Arg Asn Leu Leu Ser Pro Ser Gly Ala Leu Pro Asn Pro Phe Val Gln
                565                 570                 575

Val Ala Cys Ala Gly Thr Ser Arg Glu Thr Glu Val Phe Glu Gln Thr
                580                 585                 590

Ser Ser Pro Val Phe Met Asp Cys Leu Leu Asp Ile Thr Met Met
                595                 600                 605

Thr Asp Pro Val Ser Arg Leu Pro Thr Val Ala Pro Ile Val Val Thr
        610                 615                 620

Leu Phe Glu Gln Arg Ser Trp Gly Ile Gln Phe Leu Gly Arg Ala Thr
625                 630                 635                 640
```

-continued

```
Cys His Tyr Asp Arg Leu Arg Gly Arg Leu Lys Pro Gly Glu Ser Pro
            645                 650                 655

Thr Val Ala Glu Pro Arg Trp Ile Lys Leu Arg Gly Gly Lys Tyr Ala
            660                 665                 670

Asn Arg His Leu Gly Asp Val Leu Leu Leu Leu Glu Leu Ile Arg Lys
            675                 680                 685

Arg Asp Ala Glu Ile Ile Pro Ala Phe Pro Met Arg Pro Val Val Asn
690                 695                 700

Met Cys Asn Leu Thr Phe Ser Cys Leu Gly Val Arg Ser Leu Tyr Met
705                 710                 715                 720

Thr Gln Arg Ala Lys Arg Leu Asp Tyr Val Ser Ile Arg Lys Gly Gln
            725                 730                 735

Asp Lys Lys Thr Glu Leu Arg Arg Ile Arg Gly Pro Leu Leu Arg Ile
            740                 745                 750

Ser Val Ser Ser Tyr Ala Ser Ala Gly Arg Gly Asn Asn Glu Ala Ile
            755                 760                 765

Leu Arg Tyr Glu Arg Asn Leu Pro Glu Asp Pro Thr Thr Val Asn Lys
            770                 775                 780

Leu Trp Thr Thr Val Thr Lys Ala Ala Asn Ala Asp Ile Phe Lys Val
785                 790                 795                 800

Val Asn Met Glu Ile Asp Val Pro Val Asp Pro Ile Tyr Asp Pro Arg
            805                 810                 815

Leu Val Val Gln Val Tyr Asp Arg Lys Gln Lys Pro Lys Tyr Phe Ile
            820                 825                 830

Gly Glu Tyr Ser Met Ser Leu Val Pro Leu Ile Pro Trp Val Leu Asp
            835                 840                 845

Gln Gln Ser Ala Ile Glu Ala Val Ser Pro Val Asn Asp Phe Thr Asp
850                 855                 860

Thr Val Asp Leu Lys His Leu Gly Gly Leu Leu Arg Gly Phe His Gly
865                 870                 875                 880

Asn Ser Lys Asn Arg Gly Thr Gly Gln Ile Gly Leu Glu Ala Leu Ser
            885                 890                 895

Ala Ala Asp Arg Glu Thr Ala Asp Ala His Lys Glu Lys Thr Leu Ala
            900                 905                 910

Gln Ser Arg Phe Ala Thr Tyr Asp Pro Asp Asn Lys Thr Phe Ser Asp
            915                 920                 925

Ser Trp Leu Leu Pro Ser Gly Leu Pro Lys Ile Leu Val Ser Ser Tyr
930                 935                 940

Ala Val Pro Gly Phe Arg Cys Asp Val Ile Tyr Thr Asn Met Phe Thr
945                 950                 955                 960

Leu Asn Val Tyr Ile Pro Ala Lys Phe Val Leu Phe Ala Glu Gly Lys
            965                 970                 975

Arg Ala Ala Asp Lys Lys Thr Lys Glu Gln Tyr Ala Arg Pro Ser Val
            980                 985                 990

Asp Ser Thr Leu Glu Gln Phe Leu Asp Asp Val Ile Phe Pro Ser Asp
            995                 1000                1005

Ser Leu Lys Lys Ser Val Met Gly Asp Ile Asp Val Thr Gly Phe
            1010                1015                1020

Val Lys Phe Phe Val Asn Leu Thr His His Glu Glu Pro Asn Pro
            1025                1030                1035

His Val Asp Ser Ser Ala Ala Glu Trp Ala Ser Ser Glu Asp Arg
            1040                1045                1050
```

-continued

```
Met Arg Arg His Leu Arg Gly Glu Asp Ala Tyr Pro Lys Leu Leu
    1055                1060                1065

Lys Ile Arg Val Tyr Val Ile Arg Ala Ile Ser Leu Tyr Val Gly
    1070                1075                1080

Asp Asp Arg Ile Leu Pro Asn Pro Tyr Leu Leu Phe Asn Leu Gly
    1085                1090                1095

Asp Lys Ser Asp Thr Leu Arg Ala Glu Ala Lys Pro Asn Thr His
    1100                1105                1110

Asn Pro Glu Phe Phe Thr Val Trp Glu Lys Asp Val Met Phe Pro
    1115                1120                1125

Asp Asp Ser Gln Phe Glu Leu Gln Val Trp Ser Ala His Glu Gly
    1130                1135                1140

Thr Ser Gly Gly Leu Asp Asp Ile Phe Ile Gly Ser Thr Cys Ile
    1145                1150                1155

Asp Leu Glu Glu Arg Trp Phe Ser Lys Glu Trp Gln Lys Ser Met
    1160                1165                1170

Ser Lys Asn Gln Val Pro Met Glu Tyr Arg Pro Leu Lys Gln Met
    1175                1180                1185

Pro Ser Gly Ser Phe Lys Gly Thr Val Glu Met Trp Val Glu Leu
    1190                1195                1200

Met Asp Phe Gln Lys Ala Gly Glu Val Pro Lys Phe Asp Leu Gln
    1205                1210                1215

Ser Pro Ala Ala Thr Glu Val Glu Ile Arg Val Ile Val Trp Gly
    1220                1225                1230

Ala Arg Asn Leu Asn Phe Lys Ala Leu Gly Lys Asp Phe Val Asp
    1235                1240                1245

Ala Met Ile Arg Cys Asn Leu Asp Cys Thr Gly Tyr Arg Gly Ser
    1250                1255                1260

Gln Pro Ile Ala Gln Gln Thr Asp Val His Tyr Tyr Ser Lys Thr
    1265                1270                1275

Gly Ala Ala Ile Phe Asn Trp Arg Met Val Tyr Ser Arg Val Val
    1280                1285                1290

Met Pro Val Ser Thr Cys Val Leu Gln Ile Ala Ala Tyr Asp Asn
    1295                1300                1305

Arg Asn Met Gly Glu Ser Pro Phe Ile Gly Glu Val Asn Leu Glu
    1310                1315                1320

Leu Arg Arg Tyr Leu Glu Arg Val Ala Ser Thr Leu Asn Ser Ile
    1325                1330                1335

Asp Val Asp Ala Glu Leu Lys Leu Ile Asn Arg Ser Arg Glu Ser
    1340                1345                1350

Ala Asp Val Ser Ser Phe Gly Phe Val Gln Val Ser Leu Gln Phe
    1355                1360                1365

Ile Ser Gln Ser Glu Ala Thr Ser Lys Pro Val Gly Leu Gly Arg
    1370                1375                1380

Glu Pro Pro Asn Arg Asp Pro Arg Leu Thr Thr Pro Gln Glu Gly
    1385                1390                1395

Arg Lys Trp Glu Asp Val Leu Gly Ser Ala Gly Leu Arg Val Asp
    1400                1405                1410

Tyr Arg Pro Leu Trp Tyr Trp Val Arg Val Ala Ala Val Val Phe
    1415                1420                1425

Leu Ser Ile Trp Ile Phe Val Val Ala Phe Leu Tyr Pro Ser Leu
    1430                1435                1440

Leu Gly
```

-continued

```
        1445

<210> SEQ ID NO 30
<211> LENGTH: 1641
<212> TYPE: PRT
<213> ORGANISM: Plasmodium berghei

<400> SEQUENCE: 30

Met Ser Ile Gly Lys Lys Thr Gln Tyr Asn Ile Lys Val Asp Ile His
1               5                   10                  15

Glu Val Lys Asp Leu Ser Phe Arg Glu Ser Thr Asn Glu Lys Glu Ile
            20                  25                  30

Ile Pro Asn Pro Tyr Ile Glu Ile Arg Val Asn Asp Glu Thr Lys Cys
        35                  40                  45

Thr Ala Lys Lys Asn Gln Ala Val Asn Val Val Tyr Asn Thr Ser Phe
    50                  55                  60

Asn Phe Ser Met Asp Leu Thr Asp Tyr Asp Phe Gln Arg Thr Ser Val
65                  70                  75                  80

Glu Val Cys Val Leu His Lys Tyr Thr Ile Gln Ser Ala Leu Ile Gly
                85                  90                  95

Lys Cys Ser Phe Ser Leu Asn Tyr Val Tyr Ser Lys Val Gln His Trp
            100                 105                 110

Ile Tyr Arg Ile Trp Val Lys Leu Arg Asn Pro Asp Leu Pro Leu Asp
        115                 120                 125

Asp Val Gly Tyr Leu Leu Ile Ser Val Gly Val Tyr Gly Pro Gly Asp
    130                 135                 140

Ser Ile Pro Ile Ile Asn Asp Ser Ile Lys Thr Asn Met His Glu His
145                 150                 155                 160

Glu Ile Cys Ala Asn Asn Lys Gly Ile Asp Met His Ile Thr His Tyr
                165                 170                 175

Asp Leu Cys Ile Asn Ile Phe Arg Gly Gln Asp Ile Glu Phe Ile Asn
            180                 185                 190

Asn Ala Asn Ser Leu Phe Gln Asn Asn Leu Glu Pro Tyr Val Arg Val
        195                 200                 205

Ile His Asn Gly Phe Glu Glu Lys Thr Lys Ile Ile Arg Asn Asp Pro
    210                 215                 220

Asn Pro Val Trp Asn Leu Ser Val His Leu Pro Thr Cys Thr Pro Cys
225                 230                 235                 240

Tyr Asp Lys Asn Ile Ile Ile Glu Leu Ile Asn Gly Glu Thr Asn Gly
                245                 250                 255

Val Val Ile Phe Ser Ile Leu Leu Asp Phe Phe Glu Ile Leu Lys Arg
            260                 265                 270

Glu Ile Val Pro Arg Trp Phe Asn Ile Tyr Tyr Asn Pro Gln Asn Tyr
        275                 280                 285

Ile Phe Pro Arg Ser Ser Ile Tyr Ser Gln Asn Val Asn Gln Asn Ser
    290                 295                 300

Thr Asn Pro His Ala Phe Gly Asn Asn Gln Thr Ser Asn Asn Asn Gln
305                 310                 315                 320

Ser Val Ala Gly Ile Gly Asn Thr Ile Asn Asn Val Ser Thr Phe Gly
                325                 330                 335

Asn Tyr Leu Phe Ser Gly Thr Thr Ala Glu Lys Leu Phe Lys Asn Ala
            340                 345                 350

Ala Gln Gly Ile Asn Ile Asn Asp Ile Leu Gly Ile Thr Lys Val Gln
        355                 360                 365
```

-continued

```
Asn Ile Phe Thr Asn Asp Ile Leu Lys Glu Phe Tyr Leu Tyr Gly Gly
    370                 375                 380

Arg Ile Phe Leu Gly Val Asn Ile Thr Lys Thr His Ala Pro Gly Pro
385                 390                 395                 400

Ile Cys Ile Lys Ser Ala Lys Ile Glu His Asp Pro Pro Asn Lys Glu
                405                 410                 415

Tyr Ile Phe Cys Ala Asp Ile Tyr Glu Ile Leu Gly Val Glu Gly Asn
                420                 425                 430

Asn Lys Gln Gly Glu Tyr Glu Thr Asn Asn Leu Asn Ile Asn Asn Asp
            435                 440                 445

Gly Asn Val Leu Asn Glu Lys Asn Asn Phe Asn Asn Gly Asp Ser
450                 455                 460

Ile Ile Cys Val Cys Gly Leu Gly Pro His Lys Leu Lys Thr Pro Pro
465                 470                 475                 480

Leu Leu Pro Asn Glu Val Gly Ser Tyr Val Leu Asn Glu Ser Ala Gly
                485                 490                 495

Arg Ile Asn Glu Phe Arg Ile Phe Leu Pro Gln Asn Asn Asn Glu Gln
                500                 505                 510

Ile Tyr Asp Ile Phe Leu Tyr Ile Tyr Val Lys Ser Asn Ile Ser Val
            515                 520                 525

Thr Asp Trp Ile Thr Asn Arg Arg Asn Ile Tyr Asn Ser Ile Leu Asn
    530                 535                 540

Thr Glu Tyr Glu Asp Gly Asp Ile Asn Lys Ile Gln Lys Ile Asn Lys
545                 550                 555                 560

Met Ser Ser Ile Asn Gln Ile Ser Asp Asp Met Val Asn Asn Asn Ser
                565                 570                 575

Glu Ile Leu Asn Asn Tyr Lys Leu Lys Ser Phe Val Arg Ile Pro Phe
                580                 585                 590

Lys Tyr Leu Leu Leu Asn Glu Asn Lys Pro Lys Trp Phe Ser Met Lys
            595                 600                 605

Asn Val Glu Thr Asp Ala His Asp Tyr Asn Ile Ser Phe Phe Ala Asn
    610                 615                 620

Leu Ile Pro Cys Asn Leu Tyr Lys Lys Arg Pro Lys Arg Leu Glu Tyr
625                 630                 635                 640

Lys Leu Ser Arg Tyr Phe Phe Arg Ala Leu Ile Tyr Glu Gly Leu His
                645                 650                 655

Phe Pro Ala Lys Gly Tyr Asn Ala Phe Pro Asp Pro Tyr Ile Lys Ile
                660                 665                 670

Glu Ile Ala Gly Gln Thr Ile Lys Thr Ser Thr Ile Leu His Thr Leu
            675                 680                 685

Asn Pro Asn Tyr Tyr Glu Ala Tyr Glu Val Glu Val Ile Leu Pro Thr
    690                 695                 700

Asn Leu Asn Leu Ala Pro Asp Ile Ser Ile Glu Ala Phe Ser Val Asn
705                 710                 715                 720

Lys Ser Phe Leu Tyr Asn Asp Asp Ile Leu Leu Gly Ser Cys Thr Tyr
                725                 730                 735

Pro Ile Met Lys Val Pro Met Glu Trp Lys Arg Ser Pro Ile Trp Ile
                740                 745                 750

Asn Leu Lys Ser Ser Gln Tyr Lys Lys Cys Lys Ala Lys Leu Leu Val
            755                 760                 765

Ala Phe Glu Leu Val Pro Tyr Glu Lys Val Val Asn Asp Asp Gln Tyr
    770                 775                 780

Pro Phe Tyr Asp Asp Ile Arg Pro Ser Thr Leu Pro Gly His Val Ser
```

```
                       785                 790                 795                 800
Leu Phe Leu Val Gly Ile Arg Met Phe Lys Pro Leu Lys Asp Pro Ser
                   805                 810                 815

Val Thr Val Cys Phe Gly Arg Asp Ile Asp Asp Thr Ser Gln Phe Leu
                   820                 825                 830

Trp Tyr Glu Thr Thr Asn Lys Val Ile Ser Gly Lys Glu Gly Asn Trp
                   835                 840                 845

Asn Phe Leu Lys Tyr Phe Ser Leu Asp Val Ala Leu Pro Lys Arg Met
                   850                 855                 860

Gln His His Ser Phe Leu Glu Val Arg Val Glu Asp Arg Gly Ser Asn
865                 870                 875                 880

Thr Gly Phe Ser Gly Gly Thr Ser Asn Gly Tyr Asn Ser Ile Asn Ala
                   885                 890                 895

Ile Asn Asn Asp Asn Leu Val Gly Thr Ala Tyr Ile Thr Leu Asn Pro
                   900                 905                 910

Leu Leu Pro Trp Leu Tyr Glu Tyr Glu Gln Arg Glu Cys Ile Glu Leu
                   915                 920                 925

Phe Lys Leu His Leu Leu Glu Glu Val Leu Ile Glu Asp Ala Glu Lys
                   930                 935                 940

Ala Arg Lys Thr Tyr Asn Ser Ala Leu Ile Tyr Lys Lys Ser Ser Ile
945                 950                 955                 960

Phe Ser Lys Lys Met Ser Asn Asp Ile Phe Glu Ile Gln Gly Thr Asp
                   965                 970                 975

Glu Glu Arg Asp Gly Tyr Gly Asn Asn Asn Val Phe His Ala Leu Ser
                   980                 985                 990

Leu Asn Met Leu Glu Glu Asn Pro Phe Leu Glu Tyr Gly Asp Glu Asp
                   995                 1000                1005

Val Glu Glu Pro Asp Glu Gly Glu Asn Gly Leu Lys Asn Val Met
                   1010                1015                1020

His Lys Ile Lys Asp Asp Ile Asn Lys Glu Asp Arg Ala Glu Asn
                   1025                1030                1035

Lys Asn Ser Val Thr Glu Leu Glu Lys Lys Ile Asn Ser Asn Gly
                   1040                1045                1050

Ile Leu Ser Pro Ile Glu Thr Asn Gly Met Arg Ala Val Asn Glu
                   1055                1060                1065

Phe Glu Glu Ile Pro Asn Glu Asn Asn Gln Lys Lys Glu Ile Lys
                   1070                1075                1080

Lys Lys Lys Lys Ser Arg Lys Asn Ile Asn Asn Glu Tyr Leu Pro
                   1085                1090                1095

Tyr Asn Asp Pro Asp Phe Ala Asn Val Arg Ile Glu Asp Pro Leu
                   1100                1105                1110

Glu His Val Cys Phe Thr Gln Lys Thr Gly Gly Ile Asp Asn Asp
                   1115                1120                1125

Ile Asp Val Thr Gly Tyr Ser Asn Asn Asn Lys Ser Ile Ser Asn
                   1130                1135                1140

Ile Asn Asp Asn His Val Asn Lys Gln Tyr Thr Ser Ala Asn Thr
                   1145                1150                1155

Leu Asp Asn Ala Glu Asn Cys Gly Lys Gly Ile Tyr Gly Phe Ser
                   1160                1165                1170

Glu Asp Met Leu Asn Phe Gln Leu Ser Leu Ala Tyr Asp Asp Asp
                   1175                1180                1185

His Asp Glu Leu Gln Arg Glu Glu Met Leu Tyr Glu Tyr Glu Val
                   1190                1195                1200
```

```
Asp Met Asp Ile Asn Asp Leu Pro Tyr Leu Arg Ala Thr Ile Phe
    1205                1210                1215

Arg Cys Thr Asp Ser Gly Ile Pro Glu Ala Val Gly Tyr Leu Lys
    1220                1225                1230

Tyr Ile Cys Asn Val Tyr Asp Glu Lys Thr Met His Lys Lys Lys
    1235                1240                1245

Glu Met Val Lys Ala Cys Asp Asn Leu Val Arg Glu Tyr Lys Leu
    1250                1255                1260

Thr Arg Asn Leu Val Val Arg Ala Tyr Ile Ile Gln Ala Arg Gly
    1265                1270                1275

Leu Asn Pro Pro Ser Gly Ala Thr Asp Ile Thr Thr Tyr Ile Trp
    1280                1285                1290

Ile Lys Asn Ser Asp Glu Ile Thr Asn Ile Pro Gly Gly Leu Ser
    1295                1300                1305

His Asn Ile Lys Asp Thr Gly His Thr Lys Lys Gln Gly Tyr Lys
    1310                1315                1320

Pro Glu Phe Asn Arg Cys Tyr Gln Leu Leu Cys Ser Phe Pro Asp
    1325                1330                1335

Glu Ser Ile Ile Gln Val Cys Val Met Asn Gln Gly Ser Ile Ser
    1340                1345                1350

Asp Glu Val Ile Gly Tyr Thr Tyr Ile Asp Met Glu Asp Arg Tyr
    1355                1360                1365

Phe Asn Lys Lys Ile Lys Gln Leu Met Leu Asp Asp Ile Met Pro
    1370                1375                1380

Ile Glu Leu Arg Ser Leu Lys Leu Glu Asn Ser Thr Ile Ser His
    1385                1390                1395

Gly Ser Leu Arg Cys Trp Phe Glu Ile Phe Thr Glu Glu Phe Ala
    1400                1405                1410

Gln Leu Asn Pro Val Lys Ile Leu Cys Ser Asn Glu Pro Asp Asp
    1415                1420                1425

Tyr Gln Leu Arg Leu Val Val Trp Lys Val Leu Asn Val Ala Met
    1430                1435                1440

Asp Asn Asn Ser Thr Val Ser Leu Phe Val Arg Cys Ile Tyr Ala
    1445                1450                1455

Asp Asp Asp Ser Glu Asp Ile Arg Asp Thr Asp Ile His Tyr Asn
    1460                1465                1470

Ser Lys Asn Gly Lys Gly Ile Phe Asn Trp Arg Phe Val Tyr Asn
    1475                1480                1485

Val Lys Ile Pro Thr Asn Ser Thr Thr Ile Lys Val Gln Ile His
    1490                1495                1500

Asn Tyr Ala Leu Leu Ser Ser Asn Glu Pro Ile Gly Glu Ser Ser
    1505                1510                1515

Leu Asp Leu Ser Ala His Phe Tyr Arg Ala Arg Lys Lys Lys Gly
    1520                1525                1530

Phe Tyr His Ile Pro Arg Phe Ser Ile Ser Cys Lys His Pro Ala
    1535                1540                1545

His Lys Asn Lys Ile Arg Gly Asn Ile Glu Val Glu Ala Cys Ile
    1550                1555                1560

Leu Pro Lys Asn Glu Ala Asp Ile Asp Pro Val Gly Asn Gly Arg
    1565                1570                1575

Asp Glu Pro Asn Lys Asp Pro Phe Leu Pro Pro Ile Thr Glu Asn
    1580                1585                1590
```

```
Arg Thr Tyr Val Asp Trp Val Thr Ile Asn Glu Lys Leu Gly Asp
    1595                1600                1605

Ala Thr Ala Ser Ile Met Gln Gly Leu Lys Trp Thr Gly Val Trp
    1610                1615                1620

Val Met Val Ala Phe Ile Val Ile Gly Ile Leu Phe Ile Met Phe
    1625                1630                1635

Leu Leu Lys
    1640

<210> SEQ ID NO 31
<211> LENGTH: 1704
<212> TYPE: PRT
<213> ORGANISM: Plasmodium falciparum

<400> SEQUENCE: 31

Met Ser Ser Ile Ala Lys Lys Thr Gln Tyr Asn Ile Lys Val Asp Ile
1               5                   10                  15

His Glu Val Lys Asp Leu Ser Phe Arg Glu Ser Ala Asn Glu Lys Glu
            20                  25                  30

Ile Ile Pro Asn Pro Tyr Ile Glu Val Thr Val Asn Asn Glu Lys Lys
        35                  40                  45

Ser Thr Thr Lys Lys Asn Gln Ala Val Asn Val Val Tyr Asn Thr Ser
    50                  55                  60

Phe Asn Phe Ser Gln Asp Leu Thr Asp Tyr Lys Phe Glu Arg Thr Ser
65                  70                  75                  80

Val Asp Val Cys Val Leu His Lys Tyr Thr Ile Gln Ser Ala Leu Ile
                85                  90                  95

Gly Lys Cys Ser Phe Gly Leu Asn Phe Val Tyr Ser Lys Val Gln His
            100                 105                 110

Trp Leu Tyr Arg Ile Trp Val Lys Leu Arg Asn Pro Asp Leu Pro Leu
        115                 120                 125

Asp Asp Val Gly Phe Leu Leu Ile Ser Val Gly Val Tyr Gly Pro Gly
    130                 135                 140

Asp Ser Ile Pro Ile Val Asn Asp Ser Val Lys Thr Asp Ile His Glu
145                 150                 155                 160

Asp Val Phe Ser Asn Lys Gly Leu Asp Ile His Ile Thr His Tyr Asp
                165                 170                 175

Leu Cys Leu Asn Ile Phe Arg Gly Gln Asp Ile Glu Leu Ile Gly Asn
            180                 185                 190

Ser Thr Leu Phe Ser Asn Ile Leu Glu Pro Tyr Val Lys Val Ser His
        195                 200                 205

Asn Gly Phe Glu Glu Cys Thr Lys Val Ile Arg Asn Asp Pro Asn Pro
    210                 215                 220

Val Trp Asn Leu Ser Ile His Ile Pro Thr Cys Thr Pro Cys Tyr Asp
225                 230                 235                 240

Lys Asn Ile Leu Val Glu Leu Ile Asn Gly Glu His Asn Gly Ile Val
                245                 250                 255

Ile Tyr Ser Ile Leu Leu Asp Phe Phe Glu Ile Leu Lys Arg Glu Leu
            260                 265                 270

Ala Pro Arg Trp Phe Asn Ile Tyr Tyr Asn Pro Gln Asn Gln Ile Met
        275                 280                 285

Pro Arg Tyr Ser Glu Tyr Met Gln Asn Gly Ser Ile Gln Ile Asn Leu
    290                 295                 300

Asn Ser Thr Thr Thr Asn Asn Asn Asn Asn Ser Thr Ala Ile Asn
305                 310                 315                 320
```

```
Pro Leu Gly Asn Tyr Leu Phe Ser Gly Ala Glu Lys Ile Phe Lys
                325                 330                 335

Asn Ala Thr Gln Ala Ile Asn Ile Asn Asp Ile Leu Gly Val Thr Lys
            340                 345                 350

Val Gln Asn Met Phe Thr Asp Asp Thr Leu Lys Glu Phe Tyr Leu Tyr
            355                 360                 365

Gly Gly Arg Ile Phe Leu Ser Ala Asn Ala Thr Lys Thr His Ser Pro
        370                 375                 380

Gly Pro Ile Cys Ile Lys Ser Ala Lys Val Glu Val Asp Ala Pro Asn
385                 390                 395                 400

Lys Glu Tyr Ile Phe Cys Ala Asp Ile Tyr Glu Ile Leu Ser Val Arg
                405                 410                 415

Asn Asn Lys Met Gly Asn Tyr Asp Asp Tyr Asp Gly Gly Tyr Thr Thr
            420                 425                 430

Thr Asn Asn Asn Asn Lys Asn Lys Asn Asn Asn Asn Glu Asn Asn Asn
        435                 440                 445

Asn Asp Asn Asn Asp Asn Ile Tyr Asn Ser Asn Asn Ile Tyr Asn Ser
    450                 455                 460

Ala Ser Glu Lys Arg Arg Ser Arg Tyr Asn Asn Asn Tyr Asp Ala Ser
465                 470                 475                 480

Gly Glu Ser Ile Ile Cys Val Cys Ala Leu Gly Pro His Lys Leu Lys
                485                 490                 495

Thr Ile Pro Leu Leu Pro Asn Glu Val Gly Ser Tyr Val Leu Asn Glu
            500                 505                 510

Asn Val Gly Arg Ile Asp Glu Phe Arg Ile Phe Leu Pro Gln Asn Asn
            515                 520                 525

Asn Glu Gln Ile Tyr Asp Ile Phe Leu Tyr Ile Tyr Ile Lys Ser Asn
        530                 535                 540

Leu Ala Val Thr Asn Trp Ile Asn Asn Arg Arg Ser Ile Tyr Asn Ser
545                 550                 555                 560

Val Leu Leu Asn Asn Glu Tyr Glu Ser Gly Asp Arg Asn Lys Lys Gln
                565                 570                 575

Gly Leu His Lys Met Gly Ser Ile Asn Asn Ile Ser Glu Asp Ile Met
            580                 585                 590

Gln Asp Ser Asp Phe Leu Asn Asn Tyr Lys Leu Thr Ser Tyr Val Arg
        595                 600                 605

Ile Pro Tyr Lys Tyr Leu Leu Leu Asn Glu Asn Lys Pro Lys Trp Phe
    610                 615                 620

Ser Met Lys Asn Ile Glu Thr Asn Val His Glu Tyr Asn Ile Ser Phe
625                 630                 635                 640

Phe Ala Asn Leu Ile Pro Tyr His Ala Tyr Lys Lys Arg Pro Lys Arg
                645                 650                 655

Leu Glu Tyr Lys Leu Ser Arg Tyr Phe Phe Arg Ala Leu Ile Tyr Glu
            660                 665                 670

Gly Leu His Phe Pro Ala Lys Gly Tyr Asn Ala Phe Pro Asp Pro Tyr
        675                 680                 685

Ile Lys Ile Glu Leu Ala Gly Gln Val Ile Lys Thr Ser Thr Ile Leu
    690                 695                 700

His Thr Leu Asn Pro Asn Tyr Tyr Glu Ala Tyr Glu Val Gln Val Ile
705                 710                 715                 720

Leu Pro Thr Asn Leu Asn Leu Ala Pro Asp Ile Ser Ile Glu Ala Leu
                725                 730                 735
```

```
Ser Val Asn Lys Ser Phe Leu Tyr Asn Asp Asp Ile Leu Leu Gly Ser
            740                 745                 750

Cys Thr Phe Pro Ile Met Lys Val Pro Thr Glu Trp Lys Lys Ser Pro
        755                 760                 765

Ile Trp Ile Pro Leu Lys Ser Ser Gln Tyr Lys Lys Cys Lys Ala Lys
    770                 775                 780

Leu Leu Val Ala Phe Glu Leu Pro Val Glu Lys Val Leu Asp Asp
785                 790                 795                 800

Thr Tyr Pro Phe Tyr Asp Asp Ile Arg Pro Ser Thr Leu Pro Gly His
                805                 810                 815

Val Ser Leu Phe Leu Ile Gly Ile Arg Met Phe Lys Pro Leu Lys Asp
                820                 825                 830

Pro Ser Val Thr Val Cys Phe Gly Arg Asp Val Asp Asp Thr Ser Gln
            835                 840                 845

Phe Leu Trp His Glu Thr Thr Asn Lys Val Ile Ser Gly Lys Glu Gly
        850                 855                 860

Asn Trp Asn Phe Leu Lys Tyr Phe Ser Leu Asp Val Met Leu Pro Lys
865                 870                 875                 880

Arg Met Gln His His Ser Phe Leu Glu Val Arg Ile Glu Asp Arg Ile
                885                 890                 895

Leu Asn Ser Gly Phe Thr Gly Thr Ala Ser Ser Asn Met His Ala Val
            900                 905                 910

Asn Ala Thr Asn Asn Asn Leu Leu Ile Gly Thr Ala Tyr Ile Thr Leu
                915                 920                 925

Asn Pro Leu Leu Pro Trp Leu Asp Asn Tyr Glu Lys Asn Glu Cys Val
            930                 935                 940

Glu Leu Phe Lys Leu His Leu Leu Glu Glu Val Leu Ile Glu Asp Ala
945                 950                 955                 960

Glu Met Asp Arg Lys Ser Tyr Asn Ser Ala Leu Ile Tyr Lys Lys Ser
                965                 970                 975

Ser Ile Met Ser Arg Lys Leu Ser Asn Asp Asn Phe Glu Thr Gln Gln
            980                 985                 990

Met Gly Glu Glu Asn Gly Ile Phe Asn Asp Ile Pro Met Asn Thr Leu
        995                 1000                1005

Glu Glu Asn Val Thr Ile Lys Gly Asp Asp Ser Asp Asp Glu
1010                1015                1020

Lys Asp Asn Ser Tyr Asp Asp Glu Lys Asp Asn Ser Tyr Asp Asp
    1025                1030                1035

Glu Lys Asp Asn Ser Tyr Asp Glu Lys Asp Asn Ser Tyr Asp
    1040                1045                1050

Gly Asp Asp Lys Ser Gly His Tyr Tyr His Thr Trp Glu Asp Asn
    1055                1060                1065

Asn Asn Asn Asn Asn Asn Val Thr Ser Asp His Thr Cys Lys
    1070                1075                1080

His Lys Asn Glu His Asn Asn Lys Lys Glu Asp Glu Lys Arg
    1085                1090                1095

Lys Arg Glu Lys Lys Asn Thr Tyr Thr Thr Asn His Asp Lys Arg
    1100                1105                1110

Glu Asn Asn Asn Thr His Ile Asn Asn Asn Tyr Lys His Val Ile
    1115                1120                1125

Asp Ile Lys Lys Lys Lys Arg Lys Lys Asn Ile Lys Lys Tyr Ile
    1130                1135                1140

Asn Asn Glu Tyr Val Pro Tyr Asn Asp Pro Asp Phe Ser Asn Val
```

-continued

|  | 1145 |  |  |  | 1150 |  |  |  | 1155 |  |
| --- | --- | --- | --- | --- | --- | --- | --- | --- | --- | --- |

Arg Ile Glu Glu Thr Leu Glu His Val Cys Phe Lys Ile Asn Asp
    1160                 1165                 1170

Leu Thr Lys Lys Glu Asn Thr Tyr Ile Tyr Tyr Asn Asp Glu Gln
    1175                 1180                 1185

Glu Thr Leu Cys Asp Ser Ile Ser Ser Glu Lys Arg Lys Lys Leu
    1190                 1195                 1200

Lys Asp Ile His Phe Phe Lys Gly Gly Lys His Asp Asp Lys Glu
    1205                 1210                 1215

Lys Lys Ser Thr Ile Ile Asp Gly Lys Gln Pro Thr Thr Ile Tyr
    1220                 1225                 1230

Gly Phe Asn Glu Asp Met Leu Asn Phe Gln Leu Ser Leu Ala Asp
    1235                 1240                 1245

Asp Asp Glu Gln Glu Glu Ile Gln Arg Asp Glu Met Leu Tyr Glu
    1250                 1255                 1260

Tyr Glu Val Asp Met Asn Thr Asp Asp Leu Pro Tyr Leu Arg Ala
    1265                 1270                 1275

Thr Ile Phe Arg Cys Thr Asp Ser Gly Val Pro Glu Ala Val Gly
    1280                 1285                 1290

Tyr Leu Lys Tyr Ile Cys Asn Val Tyr Asp Glu Lys Thr Met Tyr
    1295                 1300                 1305

Leu Lys Lys Glu Met Ile Lys Lys Cys Asp Asp Leu Val Arg Glu
    1310                 1315                 1320

Tyr Arg Leu Thr Arg Asn Leu Val Val Arg Ala Tyr Ile Ile Gln
    1325                 1330                 1335

Ala Arg Gly Leu Asn Pro Pro Ser Gly Ala Thr Asp Ile Thr Thr
    1340                 1345                 1350

Tyr Ile Trp Ile Lys Asn Ser Asn Asp Met Thr Asn Ile Pro Gly
    1355                 1360                 1365

Gly Leu Ser His Asn Ile Lys Asp Thr Gly His Thr Lys Lys Gln
    1370                 1375                 1380

Gly Tyr Lys Pro Glu Phe Asn Arg Cys Tyr Gln Leu Leu Cys Ser
    1385                 1390                 1395

Phe Pro Asp Glu Ser Ile Val Gln Val Cys Ile Met Asn Gln Gly
    1400                 1405                 1410

Ser Leu Ser Asp Glu Ile Ile Gly Tyr Thr Tyr Ile Asp Met Glu
    1415                 1420                 1425

Asp Arg Tyr Phe Asn Gln Lys Ile Arg Gln Leu Met Ile Asp Asp
    1430                 1435                 1440

Leu Met Pro Ile Glu Leu Arg Ser Leu Lys Leu Glu Asn Ser Thr
    1445                 1450                 1455

Ile Ser His Gly Ser Leu Arg Cys Trp Phe Glu Ile Phe Asn Glu
    1460                 1465                 1470

Glu Phe Ala Gln Leu Asn Pro Ile Lys Val Leu Cys Ser Asn Glu
    1475                 1480                 1485

Pro Asp Asp Tyr Gln Leu Arg Leu Val Ile Trp Lys Val Asn Asn
    1490                 1495                 1500

Ala Ala Met Asp Asp Asn Ser Thr Ile Ser Leu Phe Val Arg Cys
    1505                 1510                 1515

Ile Tyr Thr Asp Glu Asp Arg Glu Asp Ile Arg Asp Thr Asp Thr
    1520                 1525                 1530

His Tyr Asn Ser Lys Asp Gly Lys Gly Ile Phe Asn Trp Arg Phe
    1535                 1540                 1545

```
Val Tyr  Asn Ile Lys Ile Pro  Thr Asn Ala Thr Asn  Ile Lys Ile
    1550                 1555                 1560

Gln Ile  His Asn Tyr Ala Leu  Leu Ser Ser Asn Glu  Pro Ile Gly
    1565                 1570                 1575

Glu Ala  Thr Leu Asp Leu Ser  Ala His Phe Tyr Arg  Ala Arg Lys
    1580                 1585                 1590

Lys Lys  Gly Tyr Tyr Pro Ile  Pro Arg Phe Trp Leu  Ser Cys Lys
    1595                 1600                 1605

His Pro  Ala His Lys Asn Lys  Val Arg Gly Asn Val  Glu Ile Glu
    1610                 1615                 1620

Gly Ser  Ile Leu Ile Lys Ser  Glu Ala Glu Leu Asp  Pro Val Gly
    1625                 1630                 1635

Asn Gly  Arg Asp Glu Pro Asn  Lys Asp Pro Tyr Leu  Pro Pro Val
    1640                 1645                 1650

Thr Glu  Asn Arg Thr Tyr Val  Asp Trp Val Met Ile  Asn Glu Lys
    1655                 1660                 1665

Phe Gly  Ala Ala Thr Ala Ser  Ile Met His Gly Leu  Lys Trp Thr
    1670                 1675                 1680

Gly Val  Trp Ile Val Val Gly  Val Ile Val Ile Gly  Ile Phe Phe
    1685                 1690                 1695

Leu Ile  Phe Leu Phe Lys
    1700

<210> SEQ ID NO 32
<211> LENGTH: 1564
<212> TYPE: PRT
<213> ORGANISM: Plasmodium yoelii

<400> SEQUENCE: 32

Met Asp Leu Thr Asp Tyr Asp Phe Gln Arg Thr Ser Val Glu Val Cys
1               5                   10                  15

Val Leu His Lys Tyr Thr Ile Gln Ser Ala Leu Ile Gly Lys Cys Ser
            20                  25                  30

Phe Ser Leu Asn Tyr Val Tyr Ser Lys Val Gln His Trp Ile Tyr Arg
        35                  40                  45

Ile Trp Val Lys Leu Arg Asn Pro Asp Leu Pro Leu Asp Asp Val Gly
    50                  55                  60

Tyr Leu Leu Ile Ser Val Gly Val Tyr Gly Pro Gly Asp Ser Ile Pro
65                  70                  75                  80

Ile Ile Asn Asp Ser Ile Lys Thr Asn Met Asn Glu His Glu Ile Tyr
                85                  90                  95

Ala Asn Asn Lys Gly Ile Asp Met His Ile Thr His Tyr Asp Leu Cys
            100                 105                 110

Ile Asn Ile Phe Arg Gly Gln Asp Ile Glu Phe Ile Asn Asn Ala Asn
        115                 120                 125

Ser Leu Phe Gln Asn Asn Leu Glu Pro Tyr Val Arg Val Ile His Asn
    130                 135                 140

Gly Phe Glu Glu Lys Thr Lys Ile Ile Arg Asn Asp Pro Asn Pro Val
145                 150                 155                 160

Trp Asn Leu Ser Val His Leu Pro Thr Cys Thr Pro Cys Tyr Asp Lys
                165                 170                 175

Asn Ile Ile Ile Glu Leu Ile Asn Gly Glu Thr Asn Gly Val Val Ile
            180                 185                 190

Phe Ser Ile Leu Leu Asp Phe Phe Glu Ile Leu Lys Arg Glu Ile Val
```

-continued

```
            195                 200                 205
Pro Arg Trp Phe Asn Ile Tyr Tyr Asn Pro Gln Asn Tyr Ile Phe Pro
210                 215                 220
Arg Ser Ser Ile Tyr Ser Gln Asn Val Asn Gln Asn Ser Thr Asn Pro
225                 230                 235                 240
His Ala Phe Gly Asn Asn Gln Asn Ser Ser Asn Asn Gln Ser Val Ala
                245                 250                 255
Gly Ile Gly Asn Thr Ile Asn Asn Val Ser Thr Phe Gly Asn Tyr Leu
            260                 265                 270
Phe Ser Gly Thr Thr Ala Glu Lys Leu Phe Lys Asn Ala Ala Gln Gly
        275                 280                 285
Ile Asn Ile Asn Asp Ile Leu Gly Ile Thr Lys Val Gln Asn Ile Phe
290                 295                 300
Thr Asn Asp Ser Leu Lys Glu Phe Tyr Leu Tyr Gly Gly Arg Ile Phe
305                 310                 315                 320
Leu Gly Val Asn Ile Thr Lys Thr His Ala Pro Gly Pro Ile Cys Ile
                325                 330                 335
Lys Ser Ala Lys Ile Glu His Asp Pro Pro Asn Lys Glu Tyr Ile Phe
            340                 345                 350
Cys Ala Asp Ile Tyr Glu Ile Leu Gly Val Gly Asn Asn Lys Gln
        355                 360                 365
Val Glu Tyr Glu Thr Asn Asn Leu Asn Asn Ile Asn Asp Gly Asn Val
370                 375                 380
Leu Asn Asp Lys Gln Ser Phe Asn Ser Asn Gly Asp Ser Ile Ile Cys
385                 390                 395                 400
Val Cys Gly Leu Gly Pro His Lys Leu Lys Thr Pro Pro Leu Leu Pro
                405                 410                 415
Asn Glu Val Gly Ser Tyr Val Leu Asn Glu Ser Ala Gly Arg Ile Asn
            420                 425                 430
Glu Phe Arg Ile Phe Leu Pro Gln Asn Asn Glu Gln Ile Tyr Asp
        435                 440                 445
Ile Phe Leu Tyr Ile Tyr Val Lys Ser Asn Ile Ser Val Thr Asp Trp
450                 455                 460
Ile Thr Asn Arg Arg Asn Ile Tyr Asn Ser Ile Leu Asn Thr Glu Tyr
465                 470                 475                 480
Glu Asp Gly Asp Ile Asn Lys Ile Gln Lys Ile Asn Lys Met Ser Ser
                485                 490                 495
Ile Asn Lys Ile Ser Asp Asp Met Val Asn Thr Asn Ser Glu Ile Leu
            500                 505                 510
Asn Asn Tyr Arg Leu Lys Ser Phe Val Arg Ile Pro Phe Lys Tyr Leu
        515                 520                 525
Leu Leu Asn Glu Asn Lys Pro Lys Trp Phe Ser Met Lys Asn Val Glu
530                 535                 540
Thr Asp Ala His Asp Tyr Asn Ile Ser Phe Phe Ala Asn Leu Ile Pro
545                 550                 555                 560
Cys Asn Leu Tyr Lys Lys Arg Pro Lys Arg Leu Glu Tyr Lys Leu Ser
                565                 570                 575
Arg Tyr Phe Phe Arg Ala Leu Ile Tyr Glu Gly Leu His Phe Pro Ala
            580                 585                 590
Lys Gly Tyr Asn Ala Phe Pro Asp Pro Tyr Ile Lys Ile Glu Ile Ala
        595                 600                 605
Gly Gln Thr Ile Lys Thr Ser Thr Ile Leu His Thr Leu Asn Pro Asn
610                 615                 620
```

```
Tyr Tyr Glu Ala Tyr Glu Val Glu Val Ile Leu Pro Thr Asn Leu Asn
625                 630                 635                 640

Leu Ala Pro Asp Ile Ser Ile Glu Ala Phe Ser Val Asn Lys Ser Phe
            645                 650                 655

Leu Tyr Asn Asp Asp Ile Leu Leu Gly Ser Cys Thr Tyr Pro Ile Met
            660                 665                 670

Lys Val Pro Met Glu Trp Lys Arg Ser Pro Ile Trp Ile Asn Leu Lys
            675                 680                 685

Ser Ser Gln Tyr Lys Lys Cys Lys Ala Lys Leu Leu Val Ala Phe Glu
690                 695                 700

Leu Val Pro Tyr Glu Lys Val Ile Asn Asp Asp Gln Tyr Pro Phe Tyr
705                 710                 715                 720

Asp Asp Ile Arg Pro Ser Thr Leu Pro Gly His Val Ser Leu Phe Leu
            725                 730                 735

Val Gly Ile Arg Met Phe Lys Pro Leu Lys Asp Pro Ser Val Thr Val
            740                 745                 750

Cys Phe Gly Arg Asp Ile Asp Asp Thr Ser Gln Phe Leu Trp Tyr Glu
            755                 760                 765

Thr Thr Asn Lys Val Ile Ser Gly Lys Glu Gly Asn Trp Asn Phe Leu
770                 775                 780

Lys Tyr Phe Ser Leu Asp Val Ala Leu Pro Lys Arg Met Gln His His
785                 790                 795                 800

Ser Phe Leu Glu Val Arg Ile Glu Asp Lys Val Ser Asn Ser Gly Phe
            805                 810                 815

Ser Gly Gly Pro Ser Asn Gly Tyr Asn Ser Ile Asn Ala Ile Asn Asn
            820                 825                 830

Asp Asn Leu Val Gly Thr Ala Tyr Ile Thr Leu Asn Pro Leu Leu Pro
            835                 840                 845

Trp Leu Tyr Glu Tyr Glu Gln Arg Glu Cys Ile Glu Leu Phe Lys Leu
            850                 855                 860

His Leu Leu Glu Glu Val Leu Ile Glu Asp Ala Glu Lys Ala Arg Lys
865                 870                 875                 880

Thr Tyr Asn Ser Ala Leu Ile Tyr Lys Lys Ser Ser Ile Phe Ser Lys
            885                 890                 895

Lys Met Ser Asn Asp Ile Phe Glu Ile Gln Gly Thr Asp Glu Glu Arg
            900                 905                 910

Asp Glu Tyr Gly Asn Ser Asn Val Phe His Ala Leu Ser Leu Asn Met
            915                 920                 925

Leu Glu Glu Asn Pro Phe Leu Glu Tyr Gly Asp Glu Asp Ala Glu Glu
            930                 935                 940

Gln Asp Glu Gly Glu Asn Gly Phe Lys Asn Val Met His Lys Ile Lys
945                 950                 955                 960

Asp Asp Ile Asn Lys Glu Asp Glu Met Glu Thr Lys Asn Ser Val Asn
            965                 970                 975

Glu Leu Glu Asn Lys Ile Asn Ser Asn Asp Ile Leu Ser Pro Asn Gly
            980                 985                 990

Ile Arg Thr Gln Asn Gly Phe Glu  Lys Ile Gln Asp Gly  Asn His Leu
            995                1000                1005

Lys Lys  Asp Ile Lys Lys Lys  Lys Lys Asn Arg Lys  Asn Ile Asn
     1010                1015                1020

Asn Glu  Tyr Val Pro Tyr Asn  Asp Pro Asp Phe Ala  Asn Val Arg
     1025                1030                1035
```

-continued

```
Ile Glu Asp Pro Leu Glu His Val Cys Phe Thr Gln Lys Thr Gly
    1040                1045                1050

Asn Ile Asp Asn Asp Val Asp Val Ser Gly Tyr Leu Asn Asn Asn
    1055                1060                1065

Lys Ser Leu Ser Asn Ile Asn Glu Asn Asn Met Asn Lys Gln Tyr
    1070                1075                1080

Ala Ser Ala Asn Thr Leu Asp Asn Ala Glu Asn Cys Gly Lys Gly
    1085                1090                1095

Ile Tyr Gly Phe Ser Glu Asp Met Leu Asn Phe Gln Leu Ser Leu
    1100                1105                1110

Ala Tyr Asp Asp Asp His Asp Glu Leu Gln Arg Glu Glu Met Leu
    1115                1120                1125

Tyr Glu Tyr Glu Val Asp Met Asp Ile Asn Asp Leu Pro Tyr Leu
    1130                1135                1140

Arg Ala Thr Ile Phe Arg Cys Thr Asp Ser Gly Ile Pro Glu Ala
    1145                1150                1155

Val Gly Tyr Leu Lys Tyr Ile Cys Asn Val Tyr Asp Glu Lys Thr
    1160                1165                1170

Met His Lys Lys Lys Glu Met Val Lys Ala Cys Asp Asn Leu Val
    1175                1180                1185

Arg Glu Tyr Lys Leu Thr Arg Asn Leu Val Val Arg Ala Tyr Ile
    1190                1195                1200

Ile Gln Ala Arg Gly Leu Asn Pro Pro Ser Gly Ala Thr Asp Ile
    1205                1210                1215

Thr Thr Tyr Ile Trp Ile Lys Asn Ser Asp Glu Ile Thr Asn Ile
    1220                1225                1230

Pro Gly Gly Leu Ser His Asn Ile Lys Asp Thr Gly His Ile Lys
    1235                1240                1245

Arg Gln Gly Tyr Lys Pro Glu Phe Asn Arg Cys Tyr Gln Leu Leu
    1250                1255                1260

Cys Ser Phe Pro Asp Glu Ser Ile Ile Gln Val Cys Val Met Asn
    1265                1270                1275

Gln Gly Ser Ile Ser Asp Glu Ile Ile Gly Tyr Thr Tyr Ile Asp
    1280                1285                1290

Met Glu Asp Arg Tyr Phe Asn Lys Lys Ile Lys Gln Leu Met Leu
    1295                1300                1305

Asp Asp Ile Met Pro Ile Glu Leu Arg Ser Leu Lys Leu Glu Asn
    1310                1315                1320

Ser Thr Ile Ser His Gly Ser Leu Arg Cys Trp Phe Glu Ile Phe
    1325                1330                1335

Thr Glu Glu Phe Ala Gln Leu Asn Pro Val Lys Ile Leu Cys Ser
    1340                1345                1350

Asn Glu Pro Asp Asp Tyr Gln Leu Arg Leu Val Val Trp Lys Val
    1355                1360                1365

Ser Asn Val Ala Met Asp Asn Asn Ser Thr Val Ser Leu Phe Val
    1370                1375                1380

Arg Cys Ile Tyr Ala Asp Asp Ser Glu Asp Ile Arg Asp Thr
    1385                1390                1395

Asp Ile His Tyr Asn Ser Lys Asn Gly Lys Gly Ile Phe Asn Trp
    1400                1405                1410

Arg Phe Val Tyr Asn Val Lys Ile Pro Thr Asn Ser Thr Thr Ile
    1415                1420                1425

Lys Val Gln Ile His Asn Tyr Ala Leu Leu Ser Ser Asn Glu Pro
```

```
                    1430                1435                1440
Ile Gly Glu Ser Ser Leu Asp Leu Ser Ala His Phe Tyr Arg Ala
            1445                1450                1455
Arg Lys Lys Lys Gly Phe Tyr His Ile Pro Arg Phe Ser Ile Ser
            1460                1465                1470
Cys Lys His Pro Ala His Lys Asn Lys Ile Arg Gly Asn Ile Glu
            1475                1480                1485
Val Glu Ala Cys Ile Leu Pro Lys Asn Glu Ala Asp Val Asp Pro
            1490                1495                1500
Val Gly Asn Gly Arg Asp Glu Pro Asn Lys Asp Pro Phe Leu Pro
            1505                1510                1515
Ala Ile Thr Glu Asn Arg Thr Tyr Val Asp Trp Val Thr Ile Asn
            1520                1525                1530
Glu Lys Leu Gly Asp Ala Thr Ala Ser Ile Met Gln Gly Leu Lys
            1535                1540                1545
Trp Thr Gly Ile Phe Ile Met Phe Val Tyr Ile Cys Val Glu Ser
            1550                1555                1560
Lys
```

<210> SEQ ID NO 33
<211> LENGTH: 1425
<212> TYPE: PRT
<213> ORGANISM: Toxoplasma gondii

<400> SEQUENCE: 33

```
Met Ala Ala Lys Ala Ile Gln Tyr Asn Ile Lys Val Asp Leu His Glu
1               5                   10                  15
Val Lys Asp Leu Ser Phe Arg Glu Ala Ala Gly Glu Lys Glu Ile Val
                20                  25                  30
Pro Asn Pro Tyr Ile Glu Val Thr Val Asn Gly Val Thr Lys Thr Thr
            35                  40                  45
Ile Gln Lys Thr Gln Val Val Ser Ala Thr Phe Asn Thr Ser Phe Asn
        50                  55                  60
Phe Thr Ala Tyr Leu Thr Pro Asp Glu Phe Ala Arg Ser Tyr Val Glu
65                  70                  75                  80
Val Ala Val Leu His Lys Tyr Met Leu Ile Gly Gly Val Gly Leu Gln
                85                  90                  95
Ser Ala Val Ile Gly Lys Tyr Val Phe Ser Phe Ala Tyr Val Tyr Thr
            100                 105                 110
Lys Ser Gln His Trp Ile Tyr Arg Gln Trp Val Thr Leu Arg Asn Leu
        115                 120                 125
Asp Gln Pro Gln Asp Glu Thr Gly Leu Leu Leu Ile Thr Val Gly Val
    130                 135                 140
Phe Gly Pro Gly Asp Ala Met Pro Val Val Asp Glu Thr Val Cys Val
145                 150                 155                 160
Val Asn Glu Gly Glu Arg Thr Ser Thr Asp Val Asn Val Lys Leu Thr
                165                 170                 175
His Tyr Ser Leu Ser Val Asn Ile Phe Lys Gly Gln Asp Ile Pro Ser
            180                 185                 190
Val Ala Gly Gln Phe Ser Thr Leu Glu Pro Tyr Val Lys Val Lys
        195                 200                 205
His Gly Gly Ala Glu Leu Gln Thr Arg Pro Leu Pro Asp Ser Asn Pro
    210                 215                 220
Asp Trp Leu Ala Ser Ile Ser Ile Pro Ala Cys Val Pro Cys Phe Asp
```

-continued

```
                225                 230                 235                 240
        Gly Asn Val Leu Val Glu Leu Trp Asn Gly Gln Asp Ser Ser Thr Ala
                            245                 250                 255

Ala Gly Thr Leu Met Gly Thr Val Leu Asp Tyr Phe Gln Leu Ile
                            260                 265             270

Lys Asn Asp Leu Pro Pro Arg Trp Phe Asn Phe Tyr Trp Arg Pro Pro
                        275                 280                 285

Ala Glu Gly Leu Leu Gly Ala Val Thr Asp Met Met Ala Ser Ala Glu
                    290                 295                 300

Leu Arg Glu Pro Ile Ala Tyr Gly Gly Arg Ile Leu Leu Ser Ala Ser
        305                 310                 315                 320

Thr Ala Lys Val Gln Thr Pro Leu Pro Leu Gly Val Arg Ser Ala Arg
                            325                 330                 335

Pro Ile Pro Asp Pro Ala Thr Gln Glu Cys Val Trp Trp Leu Asp Leu
                        340                 345                 350

Tyr Glu Met Thr Ser Ala Thr Gly Tyr Thr Ser Glu Leu Arg Ile Glu
                    355                 360                 365

Ile Ala Phe Gly Pro His Val Ile Lys Thr Ala Ser Leu Glu Ala Asn
                370                 375                 380

Ala Leu Gly Thr Tyr Val Ile Gly Asp Asn Leu Gly Arg Leu Pro Glu
        385                 390                 395                 400

Met Lys Ile Phe Ala Pro Val Asp Glu Val Gln Val Trp Asp Val Met
                            405                 410                 415

Met Tyr Val Cys Ser Pro Pro Ala Thr Thr Val Ala Ala Gly Ile Ala
                        420                 425                 430

Asp Ile Ser Asn Trp Phe Ser Gly Trp Gly Ser Pro Thr Ala Thr
                    435                 440                 445

Gln Asn Thr Pro Glu Pro Ala Glu Thr Pro Trp Thr Arg Leu Ala Trp
        450                 455                 460

Val Arg Ile Pro Tyr Asp Ser Arg Gln Phe Gln Asn Gly Lys Pro Gln
        465                 470                 475                 480

Trp Tyr Ser Leu Arg Ser Leu Asp Gly Ser Gly Thr Asp Met Phe Ser
                            485                 490                 495

Val Leu Leu Gly Met Glu Met Phe Pro Thr Lys Ala Gly Lys Gln Arg
                        500                 505                 510

Ala Pro Arg Leu Glu Tyr Lys Leu Ala Arg Phe Tyr Phe Arg Ala Leu
                    515                 520                 525

Ile Tyr Glu Gly Leu His Leu Pro Ala Val Gly Tyr Asp Val Phe Pro
                530                 535                 540

Asp Pro Tyr Ile Gln Val Glu Leu Ala Ser Lys Thr Leu Arg Thr Ser
        545                 550                 555                 560

Thr Ile Arg Gln Thr Leu Asn Pro Ser Tyr Tyr Glu Ala Tyr Glu Ile
                            565                 570                 575

Glu Ile Arg Leu Pro Glu Asn Ile Ser Leu Ala Pro Asp Ile Asn Val
                        580                 585                 590

Glu Val Ile Ser Glu Ser Asn Ser Leu Leu Ser Ser Asp Val Val Leu
                    595                 600                 605

Gly Ser Val Gln Tyr Pro Ile Gln Lys Val Pro Lys Glu Trp Thr Lys
                610                 615                 620

Ala Pro Val Trp Leu Gln Leu His Ser Lys Tyr Pro Arg Cys Lys
        625                 630                 635                 640

Ala Arg Val Leu Val Ala Phe Glu Leu Val Pro Ala Glu Lys Ala Glu
                            645                 650                 655
```

```
Asp Asp Thr Tyr Pro Phe Tyr Asp Asp Ile Arg Pro Ser Thr Lys Glu
            660                 665                 670

Gly Asn Ile Arg Leu Phe Leu Val Gly Val Arg Leu Phe Lys Pro Ile
            675                 680                 685

Thr Gln Pro Phe Val Thr Val Cys Phe Gly Arg Asp Val Glu Asn Thr
    690                 695                 700

Ala Glu Pro Leu Trp Ser Gln Glu Ser Ser Ala Pro Arg Thr Gly Glu
705                 710                 715                 720

Gly Gly Asn Trp Asn Phe Leu Glu Glu Phe Thr Val Ser Val Ser Leu
                725                 730                 735

Pro Lys Arg Met Gln His His Ser Phe Leu Glu Val Lys Ile Gln Asp
                740                 745                 750

Arg Thr Gln Gly Ile Gly Gly Glu Ser Asn Val Asp Val Gly Met Ala
            755                 760                 765

Tyr Ile Thr Leu Asn Pro Leu Leu Pro Trp Leu Asp Ser Arg Glu Arg
            770                 775                 780

Ala Glu Ser Leu Glu Thr Phe Arg Leu Gln Met Leu Glu Glu Val Leu
785                 790                 795                 800

Ile Glu Asp Ala Glu Asn Ala Arg Arg Ser Ala Asp Gly Gly Leu Ala
                805                 810                 815

Ala Arg Thr Gly Gly Gly Ser Phe Asp Glu Asp Ala Thr Lys Lys Lys
            820                 825                 830

Glu Met Leu Ala Ala Glu Arg Ser Arg Lys Met Ala Ile Pro Tyr Asn
            835                 840                 845

Asp Pro Asp Met Ala Asn Leu Lys Ile Glu Glu Val Asp Asp Tyr Val
            850                 855                 860

Ser Phe Lys Val Ala Pro Arg Pro Gln Ala Ser Arg Leu Ser Arg Glu
865                 870                 875                 880

Gly Thr Ser Arg Asp Glu Arg Gly Lys Ala Pro Gly Lys Ser Leu Ser
                885                 890                 895

Gly Met Pro Gly Pro Val Ala Arg Ala Ser Pro Gly Ala Gly Glu Glu
                900                 905                 910

Thr Glu Lys Lys Gly Asp Pro Val Ala Glu Lys Lys Glu Gly Ser Ala
            915                 920                 925

Gln Ala Ala Pro Pro Ala Ala Pro Ser Ala His Gln Arg Glu Ala Leu
            930                 935                 940

Ala Ala Ser Pro Glu Glu Glu Thr Tyr Gly Phe Thr Pro Glu Gln Leu
945                 950                 955                 960

Asn Phe Val Leu Ala Asp Leu Glu Glu Asp Ala Glu Glu Met Thr
                965                 970                 975

Arg Asp Glu Val Pro Tyr Glu Leu Glu Ala Asp Phe Thr Val Asp Asp
            980                 985                 990

Leu Pro Tyr Leu Arg Thr Pro Ile Phe Arg Pro Thr Asp Ala Gly Val
            995                 1000                1005

Pro Glu Thr Val Gly Tyr Leu Lys Tyr Val Cys Arg Val Phe Gln
    1010            1015                1020

Ser Thr Asp Glu Asp Glu Gly Ala Glu Met Asp Ala Val Cys Lys
    1025            1030                1035

Ser Leu Ile Glu Thr Tyr Asn Ser Thr Arg Asp Leu Val Val Arg
    1040            1045                1050

Ala Tyr Val Leu Ala Ala Arg Gly Leu Val Pro Pro Ser Gly Ala
    1055            1060                1065
```

```
Ser Asp Ile Gln Thr Tyr Val Trp Ile Gln Asp Ser Glu Asn Ala
    1070                1075                1080

Ala Thr Leu Pro Gly Gly Leu Ser Tyr Asn Ile Arg Asp Thr Gly
    1085                1090                1095

Tyr Thr Lys Lys Gln Gly Phe Lys Pro Glu Phe Asn Arg Cys Tyr
    1100                1105                1110

Thr Leu Ala Cys Ser Leu Pro Glu Asn Ser Ile Val Gln Ile Ala
    1115                1120                1125

Val Met Asn Met Gly Arg Leu Thr Asp Glu Cys Ile Gly Arg Thr
    1130                1135                1140

Tyr Leu Asp Val Glu Asp Arg Phe Phe Asn Lys Lys Val Glu Gln
    1145                1150                1155

Met Val Ile Glu Glu Ser Thr Pro Ile Glu Leu Arg Thr Leu Lys
    1160                1165                1170

Asn Glu Gly Ser Thr Val Ser His Gly Ser Leu Arg Gly Phe Phe
    1175                1180                1185

Glu Ile Met Arg Ala Asp Tyr Ala Gln Leu His Pro Pro Tyr Thr
    1190                1195                1200

Leu Ala Ser Ala Glu Pro Asp Glu Tyr Gln Leu Arg Val Val Ile
    1205                1210                1215

Trp Arg Val Lys Ala Val Pro Leu Asp Asp Asn Ser Ser Ile Ser
    1220                1225                1230

Leu Phe Val Arg Thr Ile Tyr Gln Leu Glu Asp Ser Ser Glu Ile
    1235                1240                1245

Val Lys Asp Thr Asp Thr His Tyr Asn Ser Thr Asp Gly Thr Ala
    1250                1255                1260

Val Tyr Asn Trp Arg Met Val Phe Asp Val Leu Ile Pro Ala Gln
    1265                1270                1275

Ile Pro Val Leu Lys Leu Gln Ile Trp Asn Tyr Ala Leu Leu Ser
    1280                1285                1290

Ser Thr Glu Pro Ile Gly Glu Ala Asn Phe Asp Leu Thr Ala Asp
    1295                1300                1305

Phe Phe Arg Ala Arg Lys Arg Gln Gln His Tyr Arg Val Pro Arg
    1310                1315                1320

Met Trp Val Arg Cys Ser His Pro Ala His Lys Gly Lys Leu Arg
    1325                1330                1335

Gly Thr Ile Glu Ile Glu Ala Ser Ile Leu Pro Arg Glu Glu Ala
    1340                1345                1350

Glu Tyr Thr Pro Val Gly Asn Gly Arg Asp Glu Pro Asn Arg Asp
    1355                1360                1365

Pro Phe Leu Pro Ala Val Thr Thr Asn Arg Thr Tyr Ile Asp Trp
    1370                1375                1380

Gln Gln Ile Gly Glu Thr Val Gly Ala Ala Ser Ser Ala Ile Met
    1385                1390                1395

Ser Gly Leu Lys Trp Thr Gly Val Trp Met Thr Val Ala Gly Ile
    1400                1405                1410

Ile Ala Leu Val Ile Phe Val Met Phe Leu Leu Lys
    1415                1420                1425

<210> SEQ ID NO 34
<211> LENGTH: 1280
<212> TYPE: PRT
<213> ORGANISM: Plasmodium berghei

<400> SEQUENCE: 34
```

-continued

```
Met Pro Thr Leu Thr Thr Lys Ile Lys Gly Ser Asn Asn Tyr Phe Ser
1               5                   10                  15

Leu Ile Ser Leu Asn Ile Asn Gly Leu Asn Ser Pro Ile Lys Arg His
            20                  25                  30

Arg Leu Thr Asp Trp Leu His Lys Gln Asp Pro Thr Phe Cys Cys Leu
        35                  40                  45

Gln Glu Thr His Leu Arg Glu Lys Asp Arg His Tyr Leu Arg Val Lys
    50                  55                  60

Gly Trp Lys Thr Ile Phe Gln Ala Asn Gly Leu Lys Lys Gln Ala Gly
65              70                  75                  80

Val Ala Ile Leu Ile Ser Asp Lys Ile Asp Phe Gln Pro Lys Val Ile
                85                  90                  95

Lys Lys Asp Lys Glu Gly His Phe Ile Leu Ile Lys Gly Lys Ile Leu
            100                 105                 110

Gln Glu Glu Leu Ser Ile Leu Asn Ile Tyr Ala Pro Asn Ala Arg Ala
        115                 120                 125

Ala Thr Phe Ile Arg Asp Thr Leu Val Lys Leu Lys Ala Tyr Ile Ala
130                 135                 140

Pro His Thr Ile Ile Val Gly Asp Phe Asn Thr Pro Leu Ser Ser Lys
145                 150                 155                 160

Asp Arg Ser Trp Lys Gln Lys Leu Asn Arg Asp Thr Val Lys Leu Thr
                165                 170                 175

Glu Val Met Lys Gln Met Asp Leu Thr Asp Ile Tyr Arg Thr Phe Tyr
            180                 185                 190

Pro Lys Thr Lys Gly Tyr Thr Phe Phe Ser Ala Pro His Gly Thr Phe
        195                 200                 205

Ser Lys Ile Asp His Ile Ile Gly His Lys Thr Gly Leu Asn Arg Tyr
210                 215                 220

Lys Asn Ile Glu Ile Val Pro Cys Ile Leu Ser Asp His His Gly Leu
225                 230                 235                 240

Arg Leu Ile Phe Asn Asn Asn Ile Asn Asn Gly Lys Pro Thr Phe Thr
                245                 250                 255

Trp Lys Leu Asn Asn Thr Leu Leu Asn Asp Thr Leu Val Lys Glu Gly
            260                 265                 270

Ile Lys Lys Glu Ile Lys Asp Phe Leu Glu Phe Asn Glu Asn Glu Ala
        275                 280                 285

Thr Thr Tyr Pro Asn Leu Trp Asp Thr Met Lys Ala Phe Leu Arg Gly
290                 295                 300

Lys Leu Ile Ala Leu Ser Ala Ser Lys Lys Arg Glu Thr Ala His
305                 310                 315                 320

Thr Ser Ser Leu Thr Thr His Leu Lys Ala Leu Glu Lys Lys Glu Ala
                325                 330                 335

Asn Ser Pro Lys Arg Ser Arg Arg Gln Glu Ile Ile Lys Leu Arg Gly
            340                 345                 350

Glu Ile Asn Gln Val Glu Thr Arg Thr Ile Gln Arg Ile Asn Gln
        355                 360                 365

Thr Arg Ser Trp Phe Phe Glu Lys Ile Asn Lys Ile Asp Lys Pro Leu
370                 375                 380

Ala Arg Leu Thr Lys Gly His Arg Asp Lys Ile Leu Ile Asn Lys Ile
385                 390                 395                 400

Arg Asn Glu Lys Gly Asp Ile Thr Thr Asp Pro Glu Glu Ile Gln Asn
                405                 410                 415
```

```
Thr Ile Arg Ser Phe Tyr Lys Arg Leu Tyr Ser Thr Lys Leu Glu Asn
            420                 425                 430

Leu Asp Glu Met Asp Lys Phe Leu Asp Arg Tyr Gln Val Pro Lys Leu
        435                 440                 445

Asn Gln Asp Gln Val Asp His Leu Asn Ser Pro Ile Ser Pro Lys Glu
    450                 455                 460

Ile Glu Ala Val Ile Asn Ser Leu Pro Thr Lys Lys Ser Pro Gly Pro
465                 470                 475                 480

Asp Gly Phe Ser Ala Glu Phe Tyr Gln Thr Phe Lys Glu Asp Leu Ile
                485                 490                 495

Pro Ile Leu His Lys Leu Phe His Lys Ile Glu Val Glu Gly Thr Leu
            500                 505                 510

Pro Asn Ser Phe Tyr Glu Ala Thr Ile Thr Leu Ile Pro Lys Pro Gln
        515                 520                 525

Lys Asp Pro Thr Lys Ile Glu Asn Phe Arg Pro Ile Ser Leu Met Asn
    530                 535                 540

Ile Asp Ala Lys Ile Leu Asn Lys Ile Leu Ala Asn Arg Ile Gln Glu
545                 550                 555                 560

His Ile Lys Ala Ile Ile His Pro Asp Gln Val Gly Phe Ile Pro Gly
                565                 570                 575

Met Gln Gly Trp Phe Asn Ile Arg Lys Ser Ile Asn Val Ile His Tyr
            580                 585                 590

Ile Asn Lys Leu Lys Asp Lys Asn His Met Ile Ile Ser Leu Asp Ala
        595                 600                 605

Glu Lys Ala Phe Asp Lys Ile Gln His Pro Phe Met Ile Lys Val Leu
    610                 615                 620

Glu Arg Ser Gly Ile Gln Gly Pro Tyr Leu Asn Met Ile Lys Ala Ile
625                 630                 635                 640

Tyr Ser Lys Pro Val Ala Asn Ile Lys Val Asn Gly Glu Lys Leu Glu
                645                 650                 655

Ala Ile Pro Leu Lys Ser Gly Thr Arg Gln Gly Cys Pro Leu Ser Pro
            660                 665                 670

Tyr Leu Phe Asn Ile Val Leu Glu Val Leu Ala Arg Ala Ile Arg Gln
        675                 680                 685

Gln Lys Glu Ile Lys Gly Ile Gln Ile Gly Lys Glu Glu Val Lys Ile
    690                 695                 700

Ser Leu Phe Ala Asp Asp Met Ile Val Tyr Ile Ser Asp Pro Lys Asn
705                 710                 715                 720

Ser Thr Arg Glu Leu Leu Asn Leu Ile Asn Ser Phe Gly Glu Val Ala
                725                 730                 735

Gly Tyr Lys Ile Asn Ser Asn Lys Ser Met Ala Phe Leu Tyr Thr Lys
            740                 745                 750

Asn Lys Gln Ala Glu Lys Glu Ile Arg Glu Thr Thr Pro Phe Ser Ile
        755                 760                 765

Val Thr Asn Asn Ile Lys Tyr Leu Gly Met Thr Leu Thr Lys Glu Val
    770                 775                 780

Lys Asp Leu Tyr Asp Lys Asn Phe Lys Ser Leu Lys Lys Glu Ile Lys
785                 790                 795                 800

Asp Leu Arg Arg Trp Lys Asp Leu Pro Cys Ser Trp Ile Gly Arg Ile
                805                 810                 815

Asn Ile Val Lys Met Ala Ile Leu Pro Lys Ala Ile Tyr Arg Phe Asn
            820                 825                 830

Ala Ile Pro Ile Lys Ile Pro Thr Gln Phe Phe Asn Glu Leu Glu Arg
```

```
            835             840             845
Ala Ile Cys Lys Phe Ile Trp Asn Asn Lys Pro Arg Ile Ala Lys
    850             855             860

Thr Leu Leu Lys Asp Lys Arg Thr Ser Gly Gly Ile Thr Met Pro Asp
865             870             875             880

Leu Lys Leu Tyr Tyr Arg Ala Ile Val Ile Lys Thr Ala Trp Tyr Trp
                885             890             895

Tyr Ser Asp Arg Gln Val Asp Gln Trp Asn Arg Ile Glu Asp Pro Glu
            900             905             910

Met Asn Pro His Thr Tyr Gly His Leu Ile Phe Asp Lys Gly Ala Lys
            915             920             925

Thr Ile Gln Trp Lys Lys Asp Ser Ile Phe Asn Lys Trp Cys Trp His
930             935             940

Asn Trp Leu Leu Ser Cys Arg Arg Met Arg Ile Asp Pro Phe Leu Ser
945             950             955             960

Pro Cys Thr Lys Val Lys Ser Lys Trp Ile Lys Glu Leu His Ile Lys
            965             970             975

Pro Glu Thr Leu Lys Leu Ile Glu Glu Lys Val Gly Lys Ser Leu Glu
            980             985             990

Asp Met Gly Thr Gly Glu Lys Phe Leu Asn Arg Thr Ala Met Ala Cys
            995             1000            1005

Ala Val Arg Ser Arg Ile Asn Lys Trp Asp Leu Ile Lys Leu Gln
    1010            1015            1020

Ser Phe Cys Lys Ala Lys Asp Thr Val Asn Lys Thr Lys Arg Pro
    1025            1030            1035

Pro Thr Asp Trp Glu Arg Ile Phe Thr Asn Pro Lys Ser Asp Arg
    1040            1045            1050

Glu Leu Ile Ser Asn Ile Tyr Lys Glu Leu Lys Lys Leu Asp Ser
    1055            1060            1065

Arg Asn Ser Asn Asn Pro Ile Lys Lys Trp Gly Ile Glu Leu Asn
    1070            1075            1080

Lys Glu Phe Ser Pro Glu Glu Tyr Gln Met Ala Glu Lys His Leu
    1085            1090            1095

Lys Lys Cys Ser Thr Ser Leu Ile Ile Arg Glu Met Gln Ile Lys
    1100            1105            1110

Thr Thr Leu Arg Phe His Leu Thr Pro Val Arg Met Ala Lys Ile
    1115            1120            1125

Lys Asn Ser Gly Asp Ser Arg Cys Trp Arg Arg Gly Gly Glu Arg
    1130            1135            1140

Gly Thr Leu Phe His Cys Trp Trp Asp Tyr Lys Leu Val Gln Pro
    1145            1150            1155

Leu Trp Lys Ser Val Trp Arg Phe Leu Arg Lys Leu Asp Ile Val
    1160            1165            1170

Leu Leu Glu Asp Pro Ala Ile Pro Leu Leu Gly Ile Tyr Pro Glu
    1175            1180            1185

Asp Val Pro Thr Gly Lys Lys Asp Thr Cys Ser Thr Met Phe Ile
    1190            1195            1200

Ala Ala Leu Phe Ile Ile Ala Arg Ser Trp Lys Glu Pro Arg Cys
    1205            1210            1215

Pro Ser Thr Glu Glu Trp Ile Gln Lys Met Trp Tyr Ile Tyr Thr
    1220            1225            1230

Met Glu Tyr Tyr Ser Ala Ile Lys Lys Asn Glu Phe Met Lys Phe
    1235            1240            1245
```

```
Leu Gly Lys Trp Met Gly Val Glu Gly Ile Ile Leu Ser Glu Val
    1250                1255                1260

Thr Gln Ser Gln Lys Asn Ser His Asp Met Tyr Ser Leu Ile Ser
    1265                1270                1275

Gly Tyr
    1280

<210> SEQ ID NO 35
<211> LENGTH: 9
<212> TYPE: PRT
<213> ORGANISM: Plasmodium berghei

<400> SEQUENCE: 35

Ser Tyr Ile Pro Ser Ala Glu Lys Ile
1               5

<210> SEQ ID NO 36
<211> LENGTH: 9
<212> TYPE: PRT
<213> ORGANISM: Plasmodium yoelii

<400> SEQUENCE: 36

Ser Tyr Val Pro Ser Ala Glu Gln Ile
1               5
```